(12) United States Patent
Polakiewicz et al.

(10) Patent No.: US 7,888,480 B2
(45) Date of Patent: Feb. 15, 2011

(54) REAGENTS FOR THE DETECTION OF PROTEIN PHOSPHORYLATION IN LEUKEMIA SIGNALING PATHWAYS

(75) Inventors: Roberto Polakiewicz, Lexington, MA (US); Valerie Goss, Seabrook, NH (US); Albrecht Moritz, Salem, MA (US); Ting-Lei Gu, Woburn, MA (US); Kimberly Lee, Seattle, WA (US)

(73) Assignee: Cell Signaling Technology, Inc., Danvers, MA (US)

(*) Notice: Subject to any disclaimer, the term of this patent is extended or adjusted under 35 U.S.C. 154(b) by 62 days.

(21) Appl. No.: 12/074,224

(22) Filed: Feb. 29, 2008

(65) Prior Publication Data

US 2008/0248490 A1 Oct. 9, 2008

(51) Int. Cl.
*C07K 16/00* (2006.01)
(52) U.S. Cl. .................................................. 530/387.9
(58) Field of Classification Search ........................ None
See application file for complete search history.

(56) References Cited

U.S. PATENT DOCUMENTS

| | | | |
|---|---|---|---|
| 3,940,475 A | 2/1976 | Gross et al. | |
| 4,289,747 A | 9/1981 | Chu et al. | |
| 4,349,893 A | 9/1982 | Wiegman et al. | |
| 4,376,110 A | 3/1983 | David et al. | |
| 4,474,893 A | 10/1984 | Reading et al. | |
| 4,634,664 A | 1/1987 | Oestberg et al. | |
| 4,634,666 A | 1/1987 | Engleman et al. | |
| 4,659,678 A | 4/1987 | Forrest et al. | |
| 4,676,980 A | 6/1987 | Segal et al. | |
| 4,727,022 A | 2/1988 | Skold et al. | |
| 4,816,397 A | 3/1989 | Boss et al. | |
| 4,816,567 A | 3/1989 | Cabilly et al. | |
| 4,946,778 A | 8/1990 | Ladner et al. | |
| 5,004,692 A | 4/1991 | Tso et al. | |
| 5,092,885 A | 3/1992 | Yamada et al. | |
| 5,112,946 A | 5/1992 | Maione et al. | |
| 5,192,744 A | 3/1993 | Bouck et al. | |
| 5,202,352 A | 4/1993 | Okada et al. | |
| 5,225,539 A | 7/1993 | Winter et al. | |
| 5,260,203 A | 11/1993 | Ladner et al. | |
| 5,530,101 A | 6/1996 | Queen et al. | |
| 5,545,806 A | 8/1996 | Lonberg et al. | |
| 5,565,332 A | 10/1996 | Hoogenboom et al. | |
| 5,585,089 A | 12/1996 | Queen et al. | |
| 5,675,063 A | 10/1997 | Knight et al. | |
| 5,677,427 A | 10/1997 | Goldenberg et al. | |
| 5,693,761 A | 12/1997 | Queen et al. | |
| 5,693,762 A | 12/1997 | Queen et al. | |
| 5,789,208 A | 8/1998 | Sharon et al. | |
| 5,969,108 A | 10/1999 | McCafferty et al. | |
| 6,103,889 A | 8/2000 | Whitlow et al. | |
| 6,120,767 A | 9/2000 | Robinson et al. | |
| 6,150,584 A | 11/2000 | Kucherlapati et al. | |
| 6,180,370 B1 | 1/2001 | Queen et al. | |
| 6,329,508 B1 | 12/2001 | Friden et al. | |
| 6,331,415 B1 | 12/2001 | Cabilly et al. | |
| 6,335,163 B1 | 1/2002 | Sharon et al. | |
| 6,355,245 B1 | 3/2002 | Evans et al. | |
| 6,395,718 B1 | 5/2002 | Slusher et al. | |
| 6,407,213 B1 | 6/2002 | Carter et al. | |
| 6,441,140 B1 | 8/2002 | Comb et al. | |
| 6,462,075 B1 | 10/2002 | Bowen et al. | |
| 6,465,431 B1 | 10/2002 | Thorn et al. | |
| 6,475,784 B1 | 11/2002 | Papkoff et al. | |
| 6,482,802 B1 | 11/2002 | Hu et al. | |
| 6,482,810 B1 | 11/2002 | Brem et al. | |
| 6,500,431 B1 | 12/2002 | Gill et al. | |
| 6,500,924 B1 | 12/2002 | Brooks et al. | |
| 6,518,298 B2 | 2/2003 | Green et al. | |
| 6,521,439 B2 | 2/2003 | Folkman et al. | |
| 6,525,019 B2 | 2/2003 | D'Amato | |
| 6,538,103 B1 | 3/2003 | Ji et al. | |
| 6,544,758 B2 | 4/2003 | O'Reilly et al. | |
| 6,544,947 B2 | 4/2003 | Holaday et al. | |
| 6,548,477 B1 | 4/2003 | Olson et al. | |
| 6,548,640 B1 | 4/2003 | Winter et al. | |

(Continued)

FOREIGN PATENT DOCUMENTS

EP 0120694 3/1984

(Continued)

OTHER PUBLICATIONS

U.S. Appl. No. 10/408,486, filed Jul. 4, 2003, Crosby et al.
U.S. Appl. No. 10/781,047, filed Feb. 17, 2004, Gygi et al.
U.S. Appl. No. 10/634,581, filed May 8, 2003, Johnson et al.
U.S. Appl. No. 10/821,234, filed Jul. 4, 2004, Labat et al.
U.S. Appl. No. 11/077,717, filed Oct. 3, 2005, Lam et al.
U.S. Appl. No. 11/089,368, filed Mar. 25, 2005, Ledbetter et al.
U.S. Appl. No. 11/049,630, Feb. 2, 2005, McKinsey et al.
Abu-Duhier et al., "Identification of novel FLT-3 Asp835 mutations in adult acute myeloid leukemia," Br. J. Haematol. 113: 983-988 (2001).

(Continued)

*Primary Examiner*—Sean E Aeder
(74) *Attorney, Agent, or Firm*—Nancy Chiu Walker

(57) ABSTRACT

The invention discloses nearly 288 novel phosphorylation sites identified in signal transduction proteins and pathways underlying human Leukemia, and provides phosphorylation-site specific antibodies and heavy-isotope labeled peptides (AQUA peptides) for the selective detection and quantification of these phosphorylated sites/proteins, as well as methods of using the reagents for such purpose. Among the phosphorylation sites identified are sites occurring in the following protein types: Adaptor/Scaffold proteins, Cytoskeletal proteins, Cellular Metabolism enzymes, G Protein/GTPase Activating/Guanine Nucleotide Exchange Factor proteins, Immunoglobulin Superfamily proteins, Inhibitor proteins, Lipid Kinases, Nuclear DNA Repair/RNA Binding/Transcription proteins, Serine/Threonine Protein Kinases, Tyrosine Kinases, Protein Phosphatases, and Translation/Transporter proteins.

4 Claims, 18 Drawing Sheets

U.S. PATENT DOCUMENTS

| | | | |
|---|---|---|---|
| 6,559,126 | B2 | 5/2003 | Tournaire et al. |
| 6,569,845 | B1 | 5/2003 | Futamura et al. |
| 6,573,256 | B2 | 6/2003 | Bishop et al. |
| 6,783,961 | B1 | 8/2004 | Edwards et al. |
| 6,867,007 | B2 | 3/2005 | Kauvar et al. |
| 6,884,869 | B2 | 4/2005 | Senter et al. |
| 6,979,557 | B2 | 12/2005 | Isogai et al. |
| 7,060,268 | B2 | 6/2006 | Andya et al. |
| 7,109,000 | B2 | 9/2006 | Edinger et al. |
| 7,198,896 | B2 | 4/2007 | Rush et al. |
| 7,300,753 | B2 | 11/2007 | Rush et al. |

FOREIGN PATENT DOCUMENTS

| | | |
|---|---|---|
| EP | 1184665 | 9/1986 |
| EP | 0239400 | 9/1987 |
| EP | 0404097 | 12/1990 |
| WO | WO 84/03508 | 9/1984 |
| WO | WO 85/03508 | 8/1985 |
| WO | WO 86/01533 | 3/1986 |
| WO | WO 91/10741 | 7/1991 |
| WO | WO 91/17271 | 11/1991 |
| WO | WO 92/01047 | 1/1992 |
| WO | WO 93/11161 | 6/1993 |
| WO | WO 93/12227 | 6/1993 |
| WO | WO 95/20401 | 8/1995 |
| WO | WO 96/27011 | 6/1996 |
| WO | WO 02/00729 | 3/2002 |
| WO | WO 03/016861 | 2/2003 |
| WO | WO 03/089474 | 10/2003 |
| WO | WO 03/106644 | 12/2003 |
| WO | WO 2004/009618 | 1/2004 |
| WO | WO 2004/039963 | 5/2004 |
| WO | WO 2004/066957 | 8/2004 |
| WO | WO 2004/091658 | 10/2004 |
| WO | WO 2005/056825 | 6/2005 |
| WO | WO 2005/083444 | 9/2005 |

OTHER PUBLICATIONS

Hardy, et al., "Clinical and Molecular Genetic Analysis of 19 Wolfram Syndrome Kindreds Demonstrating a Wide Spectrum of Mutations in WFS1," Am. J. Hum. Genet. 65:1279-1290 (1999).

Dessein, et al., "Severe Hepatic Fibrosis in Schistoma mansoni Infection Is Controlled by a Major Locust That Is Closely Linked to the Interferon-y Receptor Gene," Am. J. Hum. Genet. 65: 709-721 (1999).

Di Barletta, et al., "Different Mutations in the LMNA Gene Cause Autosomal Dominant and Autosomal Recessive Emery-Dreifuss Muscular Dystrophy," Am. J. Hum. Genet. 66:1407-1412 (2000).

Ebrahimi, et al., "Murine Gammaherpesvirus-68 Infection Causes Multi-Organ Fibrosis and Alters Leukocyte Trafficking in Interferon-y Receptor Knockout Mice," American Journal of Pathology, 158(6): 2117-2125 (Jun. 2001).

Jemal, et al., "Cancer Statistics 2005," CA: A Cancer Journal for Clinicians, 55(1): 10-30 (Jan./Feb. 2005).

Pollard, et al., "Using Single-Gene Deletions to Identify Checkpoints in the Progression of Systemic Autoimmunity," Annals of the New York Academy of Sciences 987: 236-239 (Apr. 2003).

Jaskiewicz, et al., "Expression of p53 Tumor Suppressor Gene, Oncoprotein c-erbB-2, Cellular Proliferation and Differentiation n Malignant and Benign Pancreatic Lesions," Anticancer Research 14: 1919-1922 (1994).

Agarwal, et al., "Inositol Hexaphosphate Inhibits Constitutive Activation of NF-xB in Androgen-independent Human Prostrate Carcinoma DU145 Cells," Anticancer Research 23: 3855-3862 (2003).

Arias-Romero, et al., "A tale of two Paks," Biol. Cell 100: 97-108 (2008).

Bache, et al., "Phosphorylation of Hrs downstream of the epidermal growth factor receptor," Eur. J. Biochem 269: 3881-3881 (2002).

Belsches, et al., "Role of c-Src Tyrosine Kinase in EEGF-Induced Mitogenesis," Frontiers in Bioscience 269: 3881-3887 (Oct. 15, 1997).

G-Amlak, et al., "Reguation of myeloma cell growth through Akt/Gsk3/forkhead signaling pathway," Biochemical and Biophysical Research Sommunications 297: 760-764 (2002).

Radaeva, et al., "Interferon-y inhibits interferon-a signalling in hepatic cells: evidence for the involvement of STAT1 induction and hyperexpression of STAT1 in chronic hepatitis C," Biochem J. 379: 199-208 (2004).

Awasthi, et al., "Novel Function of Human RLIP76: ATP-Dependent Transport of Glutathione Conjugates and Doxorubicin", Biochemistry 39: 9327-9334 (2000).

Jagani, et al., "Foxe tumor suppressors and BCR-ABL-induced leukemia: A matter of evasion of apoptosis," Biochimica et Biophysica Acta 1785: 63-84 (2008).

Hashimoto, et al., "The Breakpoint Cluster Region Gene on Chromosome 22q11 Is Associated with Bipolar Disorder," Biol Psychiatry 57(10): 1097-1102 (May 15, 2005).

Bird, et al., "Single-Chain Antigen-Binding Proteins," Science 242: 423-426 (Oct. 21, 1988).

Blood, et al., "Tumor interactions with the vasculature: angiogenesis and tumor metastasis," Biochemica et Biophysica Acta 1032: 89-118 (1990).

Awasthi, et al., "RLIP76, a non-ABC transporter, and drug resistance in epilepsy," BMC Neuroscience 6(61): 1-11 (2005).

Boder, et al., "Yeast surface display for screening combinatorial polypeptide libraries", Nature Biotechnology 15: 553-557 (Jun. 1997).

Bordin, et al., "Band 3 is an anchor protein and a target for SHP-2 tyrosine phosphatase in human erythrocytes," Blood 100(1): 276-282 (Jul. 1, 2002).

Brand, et al., "Fluorescence Probes for Structure1," Annu.Rev. Biochem. 41:843-868 (1972).

Brennan, et al., "Preparation of Bispecific Antibodies by Chemical Recombination of Monoclonal Immunoglobulin G1 Fragments," Science 229: 81-83 (Jul. 5, 1985).

Byers et al., "Rationale for clinical use of immunotoxins in cancer and autoimmune disease," Seminars in Cell Biology 2:59-70 (1991).

Calalb, et al.," Tyrosine Phosphorylation of Focal Adhesion Kinase at Sites in the Catalytic Domain Regulates Kinase Activity: a Role for Src Family Kinases," Molecular and Cellular Biology 15(2): 954-963 (Feb. 1995).

Grand, et al., "p53-Binding Protein 1 Is Fused to the Platelet-Derived Growth Factor Receptor B in a Patient with a t(5;15)(q33;q22) and a Imagine-Responsive Eosinophilic Myeloproliferative Disorder," Cancer Research 64: 7216-7219 (Oct. 15, 2004).

Carr, et al., "The Need for Guidelines in Publication of Peptide and Protein Identification Data," Molecular & Cellular Proteomics 3(6): 531-533 (2004).

Cell Signaling Technology, "Phospho-PLCgammal (Tyr783) Antibody," 2007 Cell Signaling Technology, Inc., Jul. 2000,1-3.

Accili et al., "FoxOs at the Crossroads of Cellular Metabolism, Differentiation, and Transformation," Cell 117: 421-426 (May 14, 2004).

Chow et al., "Measurement of Map Kinase Activation by Flow Cytometry Using Phospho-Specific Antibodies to MEK and ERK: Potential for Pharmacodynamic Monitoring of Signal Transduction Inhibitors", Cytometry (Communications in Clinical Cytometry) 46: 72-78 (2001).

Coia, et al., "Panning and selection of proteins using ribosome display", Journal of Immunological Methods 254: 191-197 (2001).

Crook, et al.,"Repressed by a NuRD", Nature Cel Biology 8(3): 212-214 (Mar. 2006).

Cross, et al., "Serine/Threonine Protein Kinases and Apoptosis", Experimental Cell Research 256: 34-41 (2000).

Czernik, et al., "Production of Phosphorylation State-Specific Antibodies", Methods in Enzymology 201: 264-283 (1991).

Daley, et al, "Induction of Chronic Myelogenous Leukemia in Mice by the P210bcr/ab1 Gene of the Philadelphia Chromosome," Science 247: 824-830 (1990).

Denslow, et al., "The human Mi-2/NuRD complex and gene regulation", Oncogene 26: 5433-5438 (2007).

Dorahy, et al., "Capture by chemical crosslinkers provides evidence that integrin allbfl3 forms complex with protein tyrosine kinases in intact platelets" Biochem J. 389: 481-490 (1995).

Druker, et al., "Imatinib as a Paradigm of Targeted Therapies," Adv. Cancer Res. 91: 1-30 (2004).

Edgar, et al., "Flotillin-1: gene structure c DNA cloning from human lung and the identification of alternative polyadenylation signals," The international Journal of Biochemisty & Cell Biology 33: 53-64 (2001).

Blanton, et al., "Schistosomal hepatic fibrosis and the interferon gamma receptor: a linkage analysis using single-nucleotide polymorphic markers", European Journal of Human Genetics 13: 660-668 (2005).

Song, et at., " Lamin A/C mutations associated with familial and sporadic cases of dilated cardiomyopathy in Koreans", Experimental and Molecular Medicine 39( 1): 114-120 (Feb. 2007).

Fanger, et al., "Bispecific antibodies and targeted cellular cytotoxicity", Immunol Today 12(2): 51-4 (Feb. 1991).

Vadlamudi, et al., "Heregulin and HER2 signaling selectively activates c-Src phosphorylation at tyrosine 215" FEBS Letters 543:76-80 (2003).

Yang, et al "ERK promotes tumorigenesis by inhibiting FOXO3a via MDM2-mediated degradation." Nat Cell Biol. 10(2):138-48 (Feb. 2008).

Fujita N. et al., "MTA3 and the Mi-2/NuRD complex regulate cell fate during B lymphocyte differentiation." Cell 119: 75-86 (2004).

Fujita N. et al., "MTA3; a Mi-2/NuRD Complex Subunit, Regulates an Invasive Growth Pathway in Breast Cancer." Cell 113: 207-19 (Apr. 18, 2003).

Meinhart, et al "A Structural Perspective of CTD Function." Genes and Development 19: 1401-1415 (2005).

Gerber et al., "Absolute quantification of proteins and phosphoproteins from cell lysates by tandem MS," PNAS 100(12): 6940-6945 (Jun. 10, 2003).

Graves et al. "Protein phosphorylation and signal transduction," Pharmacol. Ther. 82(2-3): 111-121 (1999).

Griffiths et al. "Human anti-self antibodies with high specificity from phage display libraries." EMBO Journal. 129(2): 725-734 (1993).

Griffiths et al. "Isolation of high affinity human antibodies directly from large synthetic repertoires," EMBO J. 13(14): 3245-3260 (1994).

Gruber et al. "Efficient tumor cell lysis mediated by a bispecific single chain antibody expressed in *Escherichia coli*." J. Immunol., 152: 5368-5374 (1994).

Gu et al. "Phosphotyrosine profiling identifies the KG-1 cell line as a model for the study of FGFR1 fusions in acute myeloid leukemia." Blood, 108(13): 4202-4204, supplemental table 1 (Dec. 15, 2006).

Hanes J. et al. "Picomolar affinity antibodies from a fully synthetic naive library selected and evolved by ribosome display." Nat. Biotechnol. 18:1287-92 (Dec. 2000).

Heessen S., Fornerod M., "The inner nuclear envelope as a transcription factor resting place," EMBO Rep. 8(10): 914-918 (2007).

Kakumu, et al "Interferon-gamma receptors on T cells in patients with chronic liver disease." Hepatogastroenterology 35: 158-61 (Aug. 1988).

Hollinger et al., "Diabodies: small bivalent and bispecific antibody fragments." Proc. Natl. Acaf. Sci. USA, 90: 6444-6448 (1993).

Burwinkel et al "Phosphorylase-kinase-deficient liver glycogenosis with an unusual biochemical phenotype in blood cells associated with a missense mutation in the beta subunit gene (PHKB)." Hum Genet. 101: 170-174 (Dec. 1997).

Blume-Jensen et al., "Oncogenic kinase signalling." Nature 411: 355-65 (May 2001).

Huse w. "Generation of a Large Combinatorial Library of the Immunoglobulin Repertoire in Phage Lambda." Science 246: 1275-1281 (1989).

Ingber et al., "Inhibition of Angiogenesis Through Modulation of Collagen Metabolism," Lab. Invest. 59: 44-51 (1988).

Htun Van Der Horst, et al "Tyrosine phosphorylation of PYK2 mediates heregulin-induced glioma invasion: novel heregulin/HER3-stimulated signaling pathway in glioma." Int. J Cancer 113(5): 689-98 (Feb. 20, 2005).

Irby et al., "Role of Src expression and activation in human cancer." Oncogene 16: 5636-642 (2000).

Jullien-Flores "Bridging Ral GTPase to Rho pathways RLIP76, a Ral effector with CDC42/Rac GTPase-activating protein activity." J Cell Chem 270(38): 22473-22477 (Sep. 22, 1995).

Hu, et al "HSF-1 interacts with Ral-binding protein 1 in a stress-responsive, multiprotein complex with HSP90 in vivo" J Cell Chem. 278(19): 17299-17306 (May 9, 2003).

Birkenkamp, et al "FOXO3a induces differentiation of Bcr-Ab1-transformed cells through transcriptional down-regulation of Id1." J Biol. Chem. 282(4): 2211-2220 (Jan. 26, 2007).

Goldfinger, et al "RLIP76 (RaIBP1) is an R-Ras effector that mediates adhesion-dependent Rac activation and cell migration." J Cell Biol. 174(6):877-88 (Sep 11, 2006).

Dorman, et al "Viral infections in interferon-gamma receptor deficiency." The Journal of Pediatrics 135(5):640-643 (Nov. 2006).

Kim H. et al., "Epidermal growth factor-dependent association of phosphatidylinositol 3-kinase with the erbB3 gene product" J Biol. Chem. 269(40): 24747-24755 (1994).

Kohler, et al "Derivation of specific antibody-producing tissue culture and tumor lines by cell fusion." Eur. J. Immunol. 6(7): 511-519 (1976).

Kostelny et al., "Formation of a Bispecific Antibody by the Use of Leucine Zippers." J. Immunol., 148(5): 1547-1557 (1992).

Dorman, et al "Clinical features of dominant and recessive interferon gamma receptor 1 deficiencies." Lancet 364(9451): 2113-2121 (Dec. 2004).

Merrifield "Solid Phase Peptide Synthesis I, The Synthesis of a Tetrapeptide." J. Am. Chem. Soc. 85:21-49 (1962).

Milstein and Cuello "Hybrid hybridomas and their use in immunohistochemistry." Nature, 305:537-540 (1983).

Radziwill, et al "The Bcr kinase downregulates Ras signaling by phosphorylating AF-6 and binding to its PDZ domain." Mol. Cell Biol. (13): 4663-4642 (Jul. 23, 2003).

Morrison et al., "Chimeric human antibody molecules: Mouse antigen-binding domains with human constant region domains." Proc. Nat'l Acad. Sci. 81: 6851-6855 (1984).

Moses et al., "Identification of an Inhibitor of Neovascularization from cartilage." Science, 248:1408-1410 (1990).

Mullinax et al., "Identification of human antibody fragment clones specific for tetanus toxoid in a bacteriophage gamma immunoexpression library." Proc. Nat'l Acad. Sci. 87: 8095-8099 (Oct. 1990).

Nakamura, Y., "Codon usage tabulated from international DNA sequence databases: status for the year 2000." Nucleic Acids Res. 28(1): 292 (Jan. 2000).

Nardi, et al., "Mechanisms and implications of imatinib resistance mutations in BCR-ABL." Curr. Opin. Hematol. 11: 35-43 (2003).

Shackleton, et al "LMNA, encoding lamin A/C, is mutated in partial lipodystrophy." Nat. Genet. (2):153-156 (Feb. 24, 2000).

Shankaran, et al "IFN gamma and lymphocytes prevent primary tumour development and shape tumour immunogenicity." Nature 410: 1107-1111 (Apr. 26, 2001).

Feske, et al "A mutation in Orail causes immune deficiency by abrogating CRAC channel function." Nature 441: 179-85 (May 11, 2006).

Neuberger, et al "Recombinant antibodies possessing novel effector functions." Nature. 312(5995): 604-608 (Dec. 1984).

Newman et al., "Primatization of Recombinant Antibodies for Immunotherapy of human Diseases: A Macaque/Human Chimeric Antibody Against Human CD4." BioTechnology 10: 1455-1460 (1992).

Nissim et al., "Antibody fragments from a 'single pot' phage display library as immunochemical reagents." EMBO J. 13(3):692-698 (Feb. 1994).

Ostberg, et al.,"Human x (Mouse x Human) Hybridomas Stably Producing Human Antibodies", Hybridoma 2(4): 361-367 (1983).

Olayioye, et al., "The ErbB signaling network: receptor heterodimerization in development and cancer", The EMBO Journal 19(13): 3159-3167 (2000).

Liu, et al., "Induction of prosurvival molecules by apoptotic stimuli: involvement of FOXO3a and ROS", Oncogene 24: 2020-2031 (2005).

Order, et al., "Analysis, Results, and Future Prospective of the Therapeutic Use of Radiolabeled Antibody in Cancer Therapy", Monoclonal Antibodies for Cancer Detection and Therapy, Baldwin et al. (eds.), pp. 303-316 (Academic Press 1985).

Paweletz, et al., "Reverse phase protein microarrays which capture disease progression show activation of pro-survival pathways at the cancer invasion front", Oncogene 20: 1981-1989 (2001).

Pluckthun et al., "Antibodies from *Escherichia coli*" The Pharmacology of Monoclonal Antibodies, vol. 113, Rosenburg and Moore, eds. (Springer-Verlag: New York, 1994), pp. 269-315.

Prigent, et al., "Identification of c-erbB-3 binding sites for phosphatidylinositol 3'-kinase and SHC using an EGF receptor/c-erbB-3 chimera" The EMBO Journal 13(12): 2831-2841 (1994).

Cao, Kan "A lamin a protein isoform over expressed in Hutchinson-Gilford progeria syndrome interferes with mitosis in progeria and normal cells" Proc. Natl. Acad. Sci U S A. 104(12): 4949-4954 (Mar. 2007).

Dechat, H. "Alterations in mitosis and cell cycle progression caused by a mutant lamin A known to accelerate human aging." Proc. Natl. Acad. Sci U S A. 104(12): 4955-60 (Mar. 20, 2007).

Hanes, J. "In vitro selection and evolution of functional proteins by using ribosome display" Proc. Natl. Acad. Sci. U. S. A. 94(10): 4937-4342 (1997).

Hanes, J. "Ribosome display efficiently selects and evolves high-affinity antibodies in vitro from immune libraries." Proc. Natl. Acad. Sci. U. S. A. 95(24): 14130-14135 (1998).

Masui, et al., "A possible association between missense polymorphism of the breakpoint cluser region gene and lithium prophylaxis in bipolar disorder", Progress in Neuro-Psychopharmacogy & Biological Psychiatry 32: 204-208 (2008).

Reddy, et al., "Transcriptional repression mediated by repositioning of genes to the nuclear lamina," Nature 452: 243-247 (Mar. 13, 2008).

Rosnet, et al.,"Hematopoietic Receptors of Class III Receptor-type Tyrosine Kinases", Critical Reviews in Ontogenesis, 4(6): 595-613 (1993).

Rush, et al., "Immunoaffinity Profiling of Tyrosine Phosphorylation in Cancer Cells," Nature Biotechnology, 23(1): 94-101 (2005).

Schaller, et al.,"Autophosphorylation of the Focal Adhesion Kinase, pp125FAK Directs SH2-Dependent Binding of pp60src", Molecular and Cellular Biology, 14(3): 1680-1688 (Mar. 1994).

Schindler, et al., "Structural Mechanism for STI-571 Inhibition of Abelson Tyrosine Kinase", Science 289: 1938-1942 (2000).

Schreiber, et al., "Target-Oriented and Diversity-Oriented Organic Synthesis in Drug Discovery", Science 287, 1964-1969 (2000).

Castrillon, et al., "Suppression of Ovarian Follicle Activation in Mice by the Transcription Factor Foxo3a", Science 301: 215-218 (2003).

Shalaby, et al., "Development of Humanized Bispecitic Antibodies Reactive with Cytotoxic Lymphocytes and Tumor Cells Overexpressing the HER2 Protooncogene", J. Exp. Med., 175: 217-225 (Jan. 1992).

Shen, et al.,"Evidence for SH3 domain directed binding and phosphorylation of Sam68 by Src", Oncogene 18 4647-4653 (1999).

Spira, et al.,"The identification of monoclonal, class switch variants by Sib Selection and an ELISA Assay", Journal of Immunological Methods, 74 (1984) 307-315.

Steplewski, et al., "Isolation and characterization of anti-monosialoganglioside monoclonal antibody 19-9 class-switch variants", Proc. Nat'l. Acad. Sci., USA vol. 82 pp. 8653-8657, Dec. 1985.

Stryer, et al., "Fluorescence Spectroscopy of Proteins" Science, 162: 526-533 (1986).

Suresh, et al., "Bispecific monoclonal antibodies from hybrid hybridomas" Methods in Enzymology, vol. 121, 210-228 (1986).

Tutt, et al., " Trispecific F(ab'), Derivatives That Use Cooperative Signaling Via the TCR/CD3 Complex and CD2 to Activate and Redirect Resting Cytotoxic T Cells" The Jouhnal of Immunology 147(1):60-9 (1991).

Upstate, et al., "Antibodies for Phosphorylation & Beyond", Internet Article, Jun. 2004, 1-5.

Vijapurkar, et al.,"Roles of mitogen- activated protein kinase and phosphoinositide 3'kinase in ErbB2/ErbB3 coreceptor-mediated heregulin signaling" Experimental Cell Research 284, 291-302 (2003).

Walker. et al., "Interaction of Human IgG Chimeric Antibodies With the Human FcRII Receptors: Requirements for Antibody-Mediated Host Cell-Target Cell Interaction" Molecular Immunology , vol. 26 No. 4, pp. 403-411 (1989).

Wetzel, et al., Evaluation of CML model cell lines ad imatinib mesylate response: Determinants of signaling profiles. Journal of Immunological Methods, 305: 59-66 (2005).

Yamamoto, et al., "Activating mutation of D835 within the activation loop of FLT3 in human hematologic malignancies" Blood, vol. 97, No. 8 2434-2439 (Apr. 15, 2001).

Yang, et al., "Lysine acetylation and the bromodomian: a new partnership for signaling", BioEssays, vol. 26, Iss 10, 1076-1087 (2004).

Yeatman, et at, "A Renaissance for SRC", Nature Rev. Cancer 4(6):470-480 (Jun. 2004).

Yeung, et al., "Quantitative Screening of Yeast Surface-Displayed Polypeptide Libraries by Magnetic Bead Capture" Biotechnol. Prog. 18(2):212-20 (2002).

Yokota, et al., "Internal tandem duplication of the FLT3 gene is preferentially seen in acute myeloid leukemia and myelodysplastic syndrome among various hematological malignancies. A study on a large series of patients and cell lines", Leukemia 11: 1605-1609 (1997).

Zapata, et al., "Engineering linear F (ab')2 fragments for efficient production in *Escherichia coli* and enhanced antiproliferative activity" Protein Engineering vol. 8 No. 10 pp. 1057-1062, 1995.

Zhang, et al., "Phosphoprotein Analysis Using Antibodies Broadly Reactive against Phosphorylated Motifs" Journal of Biological Chemistry, vol. 227 (42) 39379-39387 (2002).

FIGURE 2

| | A | B | C | D | E | F | G | H |
|---|---|---|---|---|---|---|---|---|
| 1 | Protein Name | Accession No. | Protein Type | Phospho-Residue | Phosphorylation Site Sequence | Disease | Cell Line / Tissue / Patient | SEQ ID NO |
| 2 | CAS1 | NP_075051 | Acetyltransferase | Y184 | IHNGSSEALSQyKMNITSIAPLLEK | CML | K562 | SEQ ID NO: 1 |
| 3 | CPT1B | NP_004368 | Acetyltransferase | Y644 | NMyRLAMTGAGIDRHLFC | AML | CMK | SEQ ID NO: 2 |
| 4 | FLJ10774 | NP_078938 | Acetyltransferase | Y820 | EELEALFLPyDLK | CML | K562 | SEQ ID NO: 3 |
| 5 | Pstpip2 | Q9H939 | Actin binding protein | Y323 | RIPDDPDySVVEDYSLLYQ | CML | Baf3/Flt3 | SEQ ID NO: 4 |
| 6 | Pstpip2 | Q9H939 | Actin binding protein | Y333 | RIPDDPDYSVVEDYSLLyQ | CML | Baf3/Flt3 | SEQ ID NO: 5 |
| 7 | SHRM | NP_065910 | Actin binding protein | Y1833 | PNEFDKyRMFIGDLDK | AML | MV4-11 | SEQ ID NO: 6 |
| 8 | AP4E1 | NP_031373 | Adaptor/scaffold | Y830 | DDyYSNTLHDTGDKE | T cell leukemia | Jurkat | SEQ ID NO: 7 |
| 9 | AP4E1 | NP_031373 | Adaptor/scaffold | Y831 | DDYySNTLHDTGDKE | T cell leukemia | Jurkat | SEQ ID NO: 8 |
| 10 | BANK1 | NP_060405 | Adaptor/scaffold | Y630 | PTSIPPKEETTPyIAQVFQQK | B cell ALL | SEM | SEQ ID NO: 9 |
| 11 | FCRL2 | NP_110391 | Adaptor/scaffold | Y502 | TLLENKDSQVIySSVK | CLL | CLL-10 | SEQ ID NO: 10 |
| 12 | FCRL3 | NP_443171 | Adaptor/scaffold | Y722 | GRAHEEDDEENyENVPR | DLBCL | OCI-ly1 | SEQ ID NO: 11 |
| 13 | FGF14 | NP_004106 | Adaptor/scaffold | Y81 | QGyYLQMHPDGALDGTKDDSTNSTLFNLIPVGLR | T cell leukemia | Jurkat | SEQ ID NO: 12 |
| 14 | FGF14 | NP_004106 | Adaptor/scaffold | Y82 | QGYyLQMHPDGALDGTKDDSTNSTLFNLIPVGLR | T cell leukemia | Jurkat | SEQ ID NO: 13 |
| 15 | LAX1 | NP_060243 | Adaptor/scaffold | Y373 | HREEMSNEDSSDyENVLTAK | DLBCL, T cell leukemia | Jurkat, OCI-ly1, OCI-ly4, OCI-ly8 | SEQ ID NO: 14 |
| 16 | LRRFIP2 | NP_006300 | Adaptor/scaffold | Y304 | SDKQYAENyTRPSSR | T cell leukemia | Jurkat | SEQ ID NO: 15 |
| 17 | LRRFIP2 | NP_006300 | Adaptor/scaffold | Y348 | DIyDLKDQIQDVEGR | CLL | CLL23LB4 | SEQ ID NO: 16 |
| 18 | MAP3K7IP2 | NP_055908 | Adaptor/scaffold | Y632 | GPHFNPSAIHNFyDNIGFVGPVPPKPK | B cell ALL | SEM | SEQ ID NO: 17 |
| 19 | PIK3AP1 | NP_689522 | Adaptor/scaffold | Y163 | AISEDSGCDSVTDTEPEDEKVVSySK | B cell ALL | SEM | SEQ ID NO: 18 |
| 20 | PRKCABP | NP_036539 | Adaptor/scaffold | Y275 | EMDDEEySCIALGEPLYR | CML | K562 | SEQ ID NO: 19 |
| 21 | PRKCABP | NP_036539 | Adaptor/scaffold | Y285 | EMDDEEYSCIALGEPLyR | CML | K562 | SEQ ID NO: 20 |
| 22 | SPG20 | NP_055902 | Adaptor/scaffold | Y45 | GLNTDELGQKEEAKNyK | AML | MV4-11 | SEQ ID NO: 21 |
| 23 | FAT | NP_005236 | Adhesion | Y400 | DVYRAEISEFAPPNTPVVMVKAIPAYSHLRyVFK | B cell ALL | SEM | SEQ ID NO: 22 |
| 24 | FAT2 | NP_001438 | Adhesion | Y2139 | yHLKVIARDGGTPSLQSEEEVLVTVR | CML | K562 | SEQ ID NO: 23 |
| 25 | ITGBL1 | NP_004782 | Adhesion | Y280 | DCRAVyDRYSDDFCSGHGQCNCGR | CML | K562 | SEQ ID NO: 24 |
| 26 | ITGBL1 | NP_004782 | Adhesion | Y283 | DCRAVYDRySDDFCSGHGQCNCGR | CML | K562 | SEQ ID NO: 25 |
| 27 | NRXN1 | NP_004792 | Adhesion | Y1027 | ITTQITAGARNLDLKSDLyIGGVAKETYKSLPK | CML | K562 | SEQ ID NO: 26 |
| 28 | NRXN1 | NP_004792 | Adhesion | Y1036 | ITTQITAGARNLDLKSDLYIGGVAKETyKSLPK | CML | K562 | SEQ ID NO: 27 |
| 29 | PARVG | NP_071424 | Adhesion | Y7 | FLyDLLQLPKGVEPPAEEE | T cell leukemia | Jurkat | SEQ ID NO: 28 |
| 30 | PCDHB5 | NP_056484 | Adhesion | Y191 | DGRKyPELVLDK | DLBCL, NSCLC | H1975, H526, OCI-ly3 | SEQ ID NO: 29 |
| 31 | PCDHGB6 | NP_061749 | Adhesion | Y418 | EQTPEyNVTIVATDRGKPPLSSSR | CML | K562 | SEQ ID NO: 30 |
| 32 | PVRL1 | NP_976030 | Adhesion | Y370 | LLAGTVAVFLILVAVLTVFFLyNR | CML | K562 | SEQ ID NO: 31 |
| 33 | PVRL2 | NP_002847 | Adhesion | Y408 | KSPGGAGGGASGDGGFyDPK | AML, NSCLC, colon cancer | H1703, HCT116, M-07e | SEQ ID NO: 32 |
| 34 | SIGLEC9 | NP_055256 | Adhesion | Y456 | GQEATDTEySEIK | AML | CMK | SEQ ID NO: 33 |
| 35 | TES | NP_056456 | Adhesion | Y251 | EGDPAIyAER | AML, CML, NSCLC, T cell ALL, acute promyelocytic | CTV-1, DU-528, HL60, HL61a, K562, MOLT15 | SEQ ID NO: 34 |
| 36 | VEZATIN | NP_060069 | Adhesion | Y514 | KDDFyYLSQEDKERQKREHEESK | T cell leukemia | Jurkat | SEQ ID NO: 35 |
| 37 | VEZATIN | NP_060069 | Adhesion | Y515 | KDDFYyLSQEDKERQKREHEESK | T cell leukemia | Jurkat | SEQ ID NO: 36 |
| 38 | BIRC4BP | NP_059993 | Apoptosis | Y261 | GDKAAyDILR | B cell ALL | SEM | SEQ ID NO: 37 |
| 39 | PAWR | NP_002574 | Apoptosis | Y177 | STGVVNIPAAECLDEyEDDEAGQKER | DLBCL, T cell leukemia | Jurkat, SU-DHL4 | SEQ ID NO: 38 |
| 40 | PAWR | NP_002574 | Apoptosis | Y241 | YKSTTSVSEEDVSSRySR | T cell leukemia | Jurkat | SEQ ID NO: 39 |
| 41 | PDCD1 | NP_005009 | Apoptosis | 121 | NDSGTyLCGAISLAPKAQIK | CLL | CLL-9 | SEQ ID NO: 40 |
| 42 | SCOTIN | NP_057563 | Apoptosis | 232 | PASQPPYNPAyMDAPKAAL | T cell leukemia | Jurkat | SEQ ID NO: 41 |
| 43 | POLS | NP_008930 | Cell cycle regulation | 339 | IATCNGEQTQNREPESPyGQR | B cell ALL, T cell leukemia | Jurkat, SEM | SEQ ID NO: 42 |
| 44 | CD300A | NP_009192 | Cell surface | 267 | EELHyASVVFOSNTNR | AML, B cell ALL | M-07e, SEM | SEQ ID NO: 43 |
| 45 | CD300A | NP_009192 | Cell surface | Y293 | IAAQRPREEEPDSDySVIR | AML, B cell ALL | M-07e, SEM | SEQ ID NO: 44 |
| 46 | MUC13 | NP_149038 | Cell surface | Y500 | DSQMQNPySR | CML | BaF3-TDII, BaF3-Tel/FGFR3, Baf3/Jak2 | SEQ ID NO: 45 |

FIGURE 2

|  | A | B | C | D | E | F | G | H |
|---|---|---|---|---|---|---|---|---|
| 1 | Protein Name | Accession No. | Protein Type | Phospho-Residue | Phosphorylation Site Sequence | Disease | Cell Line / Tissue / Patient | SEQ ID NO |
| 47 | ITPR2 | NP_002214 | Channel, calcium | Y2109 | DVGHNIyILAHQLAR | CML | K562 | SEQ ID NO: 46 |
| 48 | TRPM3 | NP_001007472 | Channel, calcium | Y712 | DFGQLAVELLDQSyKQDEQLAMK | CLL | CLL-19 | SEQ ID NO: 47 |
| 49 | C21orf55 | NP_060303 | Chaperone | Y31 | SHLIKATVIPNRVKMLPyFGIIRNR | CML | K562 | SEQ ID NO: 48 |
| 50 | TOMM34 | NP_006800 | Chaperone | Y54 | VLQAQGSSDPEEESVLySNR | AML, T cell ALL | CTV-1, MOLT15 | SEQ ID NO: 49 |
| 51 | IL12A | NP_000873 | Cytokine | Y162 | KTSFMMALCLSSIyEDLK | CML | K562 | SEQ ID NO: 50 |
| 52 | CKAP2 | NP_060674 | Cytoskeletal protein | Y598 | YNVSTTPyLQSVK | B cell ALL | SEM | SEQ ID NO: 51 |
| 53 | CKAP2 | NP_060674 | Cytoskeletal protein | Y676 | ETDAFVCRPNAALCRVyYEADTT | B cell ALL | SEM | SEQ ID NO: 52 |
| 54 | GAS2L2 | NP_644814 | Cytoskeletal protein | Y801 | RDHRPEKQPSRIPRPLAyVFLGPARQPPKDR | T cell leukemia | Jurkat | SEQ ID NO: 53 |
| 55 | GAS2L3 | NP_777602 | Cytoskeletal protein | Y683 | KKEDDDHyFVMTGSK | B cell ALL | SEM | SEQ ID NO: 54 |
| 56 | HOOK3 | NP_115786 | Cytoskeletal protein | Y347 | NTMyMQNTVSLEEELRK | AML | MKPL-1 | SEQ ID NO: 55 |
| 57 | KA35 | NP_998821 | Cytoskeletal protein | Y379 | QNQEyEILLDVKSR | CLL, T cell leukemia | CLL23LB4, Jurkat | SEQ ID NO: 56 |
| 58 | C17orf31 | NP_060045 | DNA binding protein | Y52 | RPDLEIyKPGLSR | B cell ALL | SEM | SEQ ID NO: 57 |
| 59 | C17orf31 | NP_060045 | DNA binding protein | Y508 | FQNSDNPyYYPR | B cell ALL | SEM | SEQ ID NO: 58 |
| 60 | HIST1H2BG | NP_003509 | DNA binding protein | Y43 | KESYSVYVyK | AML, B cell ALL, CML, NSCLC, T cell ALL, T cell leukemia, breast cancer | BaF3-Tel/FGFR3, BaF3-V617F-jak2, Baf3/Flt3, CMK, H1993, Jurkat, M-07e, MCF-10A (Y561F), MCF-10A(Y969F), MKPL-1, MOLT15, SEM, SUPT-13, UT-7 | SEQ ID NO: 59 |
| 61 | HIST1H2BO | NP_003518 | DNA binding protein | Y43 | KESYSIYVyK | AML, T cell ALL, breast | DU-528, MCF-10A (Y561F), MKPL-1 | SEQ ID NO: 60 |
| 62 | PCM1 | NP_006188 | DNA binding protein | Y1176 | TEyMAFPKPFESSSSIGAEKPR | CML | Baf3/TpoR, Baf3/TpoR-Y98F, Baf3/cc-TpoR-IV | SEQ ID NO: 61 |
| 63 | SMARCE1 | NP_003070 | DNA binding protein | Y170 | GEPyMSIQPAEDPDDYDDGFSMK | AML | MKPL-1 | SEQ ID NO: 62 |
| 64 | HNRPU | NP_004492 | DNA binding protein; RNA binding protein | Y247 | GYFEYIEENKySR | AML, colon | CMK, HCT116, M-07e | SEQ ID NO: 63 |
| 65 | RTN4 | NP_065393 | Endoplasmic reticulum | Y659 | SIKHEPENPPPyEE | T cell leukemia | Jurkat | SEQ ID NO: 64 |
| 66 | RTN4 | NP_065393 | Endoplasmic reticulum | Y718 | TKLSAEPAPDFSDySE | T cell leukemia | Jurkat | SEQ ID NO: 65 |
| 67 | TRAPPC1 | NP_067033 | Endoplasmic reticulum | Y39 | LMyGMLFSIRSFVSKMSPLDMK | CLL | CLL-10 | SEQ ID NO: 66 |
| 68 | RARS | NP_002878 | Enzym, misc. | Y384 | SDGGYTyDTSDLAAIK | AML, T cell ALL | CTV-1, MOLT15 | SEQ ID NO: 67 |
| 69 | ALDH2 | NP_000681 | Enzyme, cellular metabolism | Y396 | GyFIQPTVFGDVQDGMTIAK | CML | K562 | SEQ ID NO: 68 |
| 70 | GLUD1 | NP_005262 | Enzyme, cellular metabolism | Y464 | DSNyHLLMSVQESLERK | CML | K562 | SEQ ID NO: 69 |
| 71 | LDHA | NP_005557 | Enzyme, cellular metabolism | Y127 | NVNIFKFIIPNVVKySPNCK | T cell leukemia | Jurkat | SEQ ID NO: 70 |
| 72 | ACACA | AAC50139 | Enzyme, cellular metabolism; | Y306 | GYVKDVDDGLKAAEKVGyPVMIK | CLL | CLL-7 | SEQ ID NO: 71 |
| 73 | AARS | NP_001596 | Enzyme, misc. | Y543 | TCFYAEQGGQIyDEGYLVK | T cell leukemia | Jurkat | SEQ ID NO: 72 |
| 74 | ALDOA | NP_000025 | Enzyme, misc. | Y3 | PyQYPALTPEQK | AML, NSCLC, SCLC, T cell ALL, T cell leukemia, breast cancer, lymphoma | BV173, CMK, DMS 79, DU-528, HCC827, Jurkat, MCF-10A (Y561F), MCF-10A(Y969F), MOLT15, SUPT-13 | SEQ ID NO: 73 |
| 75 | BG1 | NP_055977 | Enzyme, misc. | Y719 | LTVLEKYKGIIDSFyQEQK | AML | MKPL-1 | SEQ ID NO: 74 |
| 76 | CAD | NP_004332 | Enzyme, misc. | Y1890 | KVAEPELMGTPDGTCyPPPPVPR | T cell leukemia | Jurkat | SEQ ID NO: 75 |
| 77 | CSAD | NP_057073 | Enzyme, misc. | Y158 | LRALVGWSSGDGIFCPGGSISNMyAVNLAR | T cell leukemia | Jurkat | SEQ ID NO: 76 |
| 78 | FA2H | NP_077282 | Enzyme, misc. | Y311 | CMQLILPEAVGGTVFAGGLLGYVLyDMTH | B cell ALL | SEM | SEQ ID NO: 77 |
| 79 | FASN | NP_004095 | Enzyme, misc. | Y289 | SLYQSAGVAPESFEyIEAHGTGTK | T cell leukemia | Jurkat | SEQ ID NO: 78 |
| 80 | FASN | AAC50259 | Enzyme, misc. | Y2433 | AKySGNVMLLR | CML | K562 | SEQ ID NO: 79 |
| 81 | FUCA1 | NP_000138 | Enzyme, misc. | Y301 | FKPQSLPDHKWEMCTSIDKFSWGyRR | T cell leukemia | Jurkat | SEQ ID NO: 80 |
| 82 | GALE | NP_000394 | Enzyme, misc. | Y267 | IyNLGTGTGYSVLQMVQAMEKASGKKIPYK | CML | K562 | SEQ ID NO: 81 |
| 83 | GALE | NP_000394 | Enzyme, misc. | Y275 | IYNLGTGTGySVLQMVQAMEKASGKKIPYK | CML | K562 | SEQ ID NO: 82 |
| 84 | GLA | NP_000160 | Enzyme, misc. | Y134 | LGIyADVGNK | T cell leukemia | Jurkat | SEQ ID NO: 83 |

FIGURE 2

| | A | B | C | D | E | F | G | H |
|---|---|---|---|---|---|---|---|---|
| 1 | Protein Name | Accession No. | Protein Type | Phospho-Residue | Phosphorylation Site Sequence | Disease | Cell Line / Tissue / Patient | SEQ ID NO |
| 85 | GLA | NP_000160 | Enzyme, misc. | Y329 | ALLQDKDVIAINQDPLGKQGyQLRQGDNFEVWER | CML | K562 | SEQ ID NO: 84 |
| 86 | MOGAT2 | NP_079374 | Enzyme, misc. | Y154 | DyIMSAGLVTSEKESAAHILNRK | AML, B cell ALL, T cell | CMK, ELF-153, HU-3, Jurkat, MKPL-1, SEM, UT-7 | SEQ ID NO: 85 |
| 87 | TARS | NP_689508 | Enzyme, misc. | Y298 | IyGISFPDPK | AML, T cell ALL, T cell leukemia, anaplastic | CMK, DU-528, HU-3, JB, Jurkat, M-07e, MKPL-1, MOLT15, UT-7 | SEQ ID NO: 86 |
| 88 | UROC1 | NP_653240 | Enzyme, misc. | Y185 | LVITNGMVIPNySSRTEYEK | B cell ALL | EHEB | SEQ ID NO: 87 |
| 89 | VARS2 | NP_006286 | Enzyme, misc. | Y280 | DPGVITyDLPTPPGEK | CML | K562 | SEQ ID NO: 88 |
| 90 | WARS | NP_004175 | Enzyme, misc. | Y316 | DRTDIQCLIPCAIDQDPyFR | AML, CML, T | Baf3-V617F -jak2, CTV-1, MKPL-1, | SEQ ID NO: 89 |
| 91 | USH2A | NP_996816 | Extracelluar matrix | Y3701 | HIIINSTTVELyWSLPEK | CML | K562 | SEQ ID NO: 90 |
| 92 | SYTL4 | NP_542775 | G protein regulator, misc. | Y554 | EAKNLTAAKAGGTSDSFVKGyLLPMRNK | T cell leukemia | Jurkat | SEQ ID NO: 91 |
| 93 | SPG3A | NP_056999 | G protein, monomeric (non-Rab) | Y538 | HLyHQAFPTPKSESTEQSEKKK | T cell leukemia | Jurkat | SEQ ID NO: 92 |
| 94 | RAB11B | NP_004209 | G protein, Rab | Y73 | AQIWDTAGQERyR | T cell leukemia | Jurkat | SEQ ID NO: 93 |
| 95 | ARFGAP3 | NP_055385 | GTPase activating protein, ARF | Y349 | KKYNDDSDDSyFTSSSR | AML, B cell ALL, T cell leukemia, acute promyelocytic leukemia, breast | HL60, Jurkat, MDA-MB-468, MKPL-1, MV4-11, SEM, UT-7 | SEQ ID NO: 94 |
| 96 | GPSM1 | NP_056412 | GTPase activating protein, misc. | Y376 | LTSPAASEKPDLAGyEAQGARPK | AML | MKPL-1 | SEQ ID NO: 95 |
| 97 | TBC1D15 | NP_073608 | GTPase activating protein, misc. | Y215 | NCQNKSLSQSFENLLDEPAyGLIQAG | AML | CTV-1 | SEQ ID NO: 96 |
| 98 | DLC1 | NP_006085 | GTPase activating protein, Rac/Rho | Y919 | EKFKGWVSYSTSEQAELSyK | CML | K562 | SEQ ID NO: 97 |
| 99 | RICS | NP_055530 | GTPase activating protein, Rac/Rho | Y1283 | SDyHVTQLQPYFENGR | B cell ALL | SEM, rat brain | SEQ ID NO: 98 |
| 100 | RICS | NP_055530 | GTPase activating protein, Rac/Rho | Y1353 | SLySYAGLAPRPR | T cell leukemia | Jurkat | SEQ ID NO: 99 |
| 101 | RICS | NP_055530 | GTPase activating protein, Rac/Rho | Y1369 | ANVTGyFSPNDHNVVSMPPAADVK | B cell ALL | SEM | SEQ ID NO: 100 |
| 102 | DOCK8 | NP_982272 | Guanine nucleotide exchange factor, misc. | Y869 | MSyYCSGSSDAPSSPAAPRPASK | B cell ALL | SEM | SEQ ID NO: 101 |
| 103 | ARHGEF18 | NP_056133 | Guanine nucleotide exchange factor, | Y845 | VSMLPSGVGPEyAERPEVAR | B cell ALL | SEM | SEQ ID NO: 102 |
| 104 | MCF2L2 | NP_055893 | Guanine nucleotide exchange factor, | Y751 | yLKGPSQRLIK | CML | K562 | SEQ ID NO: 103 |
| 105 | RASGRP2 | NP_005816 | Guanine nucleotide exchange factor, Ras | Y189 | HSSLIDIDSVPTyK | B cell ALL | SEM | SEQ ID NO: 104 |
| 106 | DDX17 | NP_006377 | Helicase | Y580 | TTSSANNPNLMyQDECDRR | AML, T cell | Jurkat, MKPL-1 | SEQ ID NO: 105 |
| 107 | DDX23 | NP_004809 | Helicase | Y599 | MLANFESGKHKyR | AML | MKPL-1 | SEQ ID NO: 106 |
| 108 | ASPA | NP_000040 | Hydrolase | Y64 | yIDCDLNRIFDLENLGKK | CML | K562 | SEQ ID NO: 107 |
| 109 | HAGH | NP_005317 | Hydrolase, esterase | Y145 | FyEGTADEMCKALLEVLGR | T cell leukemia | Jurkat | SEQ ID NO: 108 |
| 110 | HINT1 | NP_005331 | Hydrolase, esterase | Y109 | MVVNEGSDGGQSVyHVHLHVLGGR | breast cancer | MCF-10A(Y969F) | SEQ ID NO: 109 |
| 111 | MPG | NP_001015052 | Hydrolase, non- | Y66 | CLGPPTTPGPyR | B cell ALL | SEM | SEQ ID NO: 110 |
| 112 | RENT1 | NP_002902 | Hydrolase, non-esterase | Y114 | TSQLLAELNFEEDEEDTYyTK | T cell leukemia | Jurkat | SEQ ID NO: 111 |
| 113 | UNG | NP_550433 | Hydrolase, non-esterase | Y8 | MIGQKTLySFFSPSPAR | AML, T cell | Jurkat, MKPL-1 | SEQ ID NO: 112 |
| 114 | NCDN | NP_001014839 | Inhibitor protein | Y378 | EAIGAVIHyLLQVGSEKQK | T cell leukemia | Jurkat | SEQ ID NO: 113 |
| 115 | SPRED1 | NP_689807 | Inhibitor protein | Y187 | RVyMQSQANQITFGQPGLDIQSRSMEYVQR | CML | K562 | SEQ ID NO: 114 |
| 116 | SUFU | NP_057253 | Inhibitor protein | Y60 | yWLGGPDPLDYVSMYR | CLL | CLL-16 | SEQ ID NO: 115 |
| 117 | PIN4 | NP_006214 | Isomerase | Y147 | FGyHIIMVEGR | NSCLC, breast cancer, myeloproliferative diseases | 293T-FGFR, 293T-FGFR+bFGF, H1703, MCF-10A (Y561F), MCF-10A (Y969F) | SEQ ID NO: 116 |
| 118 | IPMK | NP_689416 | Kinase (non-protein) | Y127 | YLPKYYGIWSPPTAPNDLyLKLEDVTHK | T cell leukemia | Jurkat | SEQ ID NO: 117 |

FIGURE 2

| | A | B | C | D | E | F | G | H |
|---|---|---|---|---|---|---|---|---|
| 1 | Protein Name | Accession No. | Protein Type | Phospho-Residue | Phosphorylation Site Sequence | Disease | Cell Line / Tissue / Patient | SEQ ID NO |
| 119 | TAOK3 | NP_057365 | KINASE; Protein kinase, Ser/Thr (non- | Y429 | PTQSVQSQALHyR | B cell ALL | SEM | SEQ ID NO: 118 |
| 120 | TLK1 | NP_036422 | KINASE; Protein kinase, Ser/Thr (non- | Y669 | EPPKISNKVDVWSVGVIFFQCLyGR | T cell leukemia | Jurkat | SEQ ID NO: 119 |
| 121 | ACAS2L | NP_115890 | Ligase | Y623 | IAKyAVPDEILVVKRLPKTR | DLBCL | OCI-ly1 | SEQ ID NO: 120 |
| 122 | SCLY | NP_057594 | Lyase | Y33 | VyMDYNATTPLEPEVIQAMTK | CML | K562 | SEQ ID NO: 121 |
| 123 | SCLY | NP_057594 | Lyase | Y36 | VYMDyNATTPLEPEVIQAMTK | CML | K562 | SEQ ID NO: 122 |
| 124 | NSD1 | NP_071900 | Methyltransferase | Y1400 | TPGNyESKRQRKPTKKLLESNDLDPGFMPK | T cell leukemia | Jurkat | SEQ ID NO: 123 |
| 125 | MRPL38 | NP_115867 | Mitochondrial | Y154 | MPVyCGNEVTPTEAAQAPEV | T cell leukemia | Jurkat | SEQ ID NO: 124 |
| 126 | RTN4IP1 | NP_116119 | Mitochondrial | Y94 | MRSGyGATALNMK | CML | K562 | SEQ ID NO: 125 |
| 127 | DNAH11 | NP_003768 | Motor protein | Y437 | VQVAVNILKTFKNSFFNyRK | acute promyelocytic leukemia | HL60 | SEQ ID NO: 126 |
| 128 | DNAH11 | NP_003768 | Motor protein | Y759 | yIGNLDLLVQGYNKLK | T cell leukemia | Jurkat | SEQ ID NO: 127 |
| 129 | DNAH3 | NP_060009 | Motor protein | Y1559 | FRTVAMMVPDyALIGEISL | B cell ALL | SEM | SEQ ID NO: 128 |
| 130 | DNAH8 | NP_001362 | Motor protein | Y1010 | DISKLVLLLSSSVNSLRKAAHEALQDFQKyK | T cell leukemia | Jurkat | SEQ ID NO: 129 |
| 131 | MYH14 | NP_079005 | Motor protein | Y1045 | RRRRSRASISyGSNMRPQSQTWRDRLR | T cell leukemia | Jurkat | SEQ ID NO: 130 |
| 132 | MYH15 | XP_036988 | Motor protein | Y362 | YGCyKLTGAIMHFGNMK | T cell leukemia | Jurkat | SEQ ID NO: 131 |
| 133 | MYO1G | NP_149043 | Motor protein | Y548 | LLyNSTDPTLR | AML, T cell ALL, T cell leukemia, | DU-528, HU-3, Jurkat, MOLT15, SUPT-13 | SEQ ID NO: 132 |
| 134 | MYBPC3 | NP_000247 | Myosin binding protein | Y1119 | KTMEWFTVLEHyRR | CLL | CLL-6 | SEQ ID NO: 133 |
| 135 | COX11 | NP_004366 | Oxidoreductase | Y117 | QNKTTLTYVAAVAVGMLGASYAAVPLyR | B cell ALL | SEM | SEQ ID NO: 134 |
| 136 | NUDT11 | NP_060629 | Phosphatase (non-protein) | Y11 | MKCKPNQTRTyDPEGFKK | T cell leukemia | Jurkat | SEQ ID NO: 135 |
| 137 | PPP2R5B | NP_006235 | Phosphatase, regulatory subunit | Y244 | FlyEFEHFNGVAELLEILGSIINGFALPLK | DLBCL | OCI-ly12 | SEQ ID NO: 136 |
| 138 | PTPN22 | NP_036543 | Phosphatase; Protein phosphatase, tyrosine (non-receptor) | Y526 | HHDSSALGVySYIPLVENPYFSSWPPSGTSSK | acute promyelocytic leukemia | HL60 | SEQ ID NO: 137 |
| 139 | PTPN22 | NP_036543 | Phosphatase; Protein phosphatase, tyrosine (non-receptor) | Y528 | HHDSSALGVYSyIPLVENPYFSSWPPSGTSSK | acute promyelocytic leukemia | HL60 | SEQ ID NO: 138 |
| 140 | PTPN22 | NP_036543 | Phosphatase; Protein phosphatase, tyrosine (non-receptor) | Y536 | HHDSSALGVYSYIPLVENPyFSSWPPSGTSSK | acute promyelocytic leukemia | HL60 | SEQ ID NO: 139 |
| 141 | PTPRCAP | NP_005599 | Phosphatase; Receptor protein phosphatase, tyrosine | Y64 | DSGGyYHPAR | B cell ALL | SEM | SEQ ID NO: 140 |
| 142 | PUM1 | NP_055491 | Phosphatase; Receptor protein phosphatase, tyrosine | Y83 | SQDDAMVDyFFQR | T cell leukemia | Jurkat | SEQ ID NO: 141 |
| 143 | ADAMTS14 | NP_542453 | Protease (non-proteasomal) | Y38 | LSDyGVTVPCSTDFR | CLL | CLL-16 | SEQ ID NO: 142 |
| 144 | SENP2 | NP_067640 | Protease (non-proteasomal) | Y239 | LKESGHGNSVCPVTSNyHSSQR | B cell ALL | SEM | SEQ ID NO: 143 |
| 145 | TRHDE | NP_037513 | Protease (non-proteasomal) | Y179 | NATRyVVLHASR | CML | K562 | SEQ ID NO: 144 |
| 146 | TRHDE | NP_037513 | Protease (non-proteasomal) | Y672 | ITyLDKGSWLLGNINQTGYFR | breast cancer, colon cancer, pre-B ALL | CLL-7, HT29, MCF-10A(Y969F), SD1 | SEQ ID NO: 145 |
| 147 | AVO3 | NP_689969 | Protein kinase, regulatory subunit | Y1269 | TSHyLTPQSNHLSLSK | B cell ALL | SEM | SEQ ID NO: 146 |
| 148 | BCCIP | NP_057651 | Protein kinase, regulatory subunit | Y257 | AALMFANAEEEFFyEEQGKPEVLGGPDTR | T cell leukemia | Jurkat | SEQ ID NO: 147 |
| 149 | CELSR2 | NP_001399 | Receptor, GPCR | Y1459 | yYNKPLLGQTGLPQGPSEQK | CML | K562 | SEQ ID NO: 148 |
| 150 | CELSR2 | NP_001399 | Receptor, GPCR | Y1460 | YyNKPLLGQTGLPQGPSEQK | CML | K562 | SEQ ID NO: 149 |
| 151 | GPR172A | NP_078807 | Receptor, GPCR | Y430 | PALLAAGVAIQVGSLLGAVAMFPPTSIyHVFHSR | CLL | CLL-7 | SEQ ID NO: 150 |
| 152 | OR10A6 | NP_001004461 | Receptor, GPCR | Y259 | AFSTCAAHLTSVTLFYGTASMTyLQPK | T cell leukemia | Jurkat | SEQ ID NO: 151 |

FIGURE 2

| | A | B | C | D | E | F | G | H |
|---|---|---|---|---|---|---|---|---|
| 1 | Protein Name | Accession No. | Protein Type | Phospho-Residue | Phosphorylation Site Sequence | Disease | Cell Line / Tissue / Patient | SEQ ID NO |
| 153 | OR2A7 | NP_001005328 | Receptor, GPCR | Y258 | AFCTCFSHLCVIGLFYGTAIIMyVGPR | T cell leukemia | Jurkat | SEQ ID NO: 152 |
| 154 | OR2B2 | NP_149046 | Receptor, GPCR | Y290 | GKMVSLFCGIIAPMLNPLIyTLR | CML | K562 | SEQ ID NO: 153 |
| 155 | OR2G3 | NP_001001914 | Receptor, GPCR | Y102 | TITYGGCVAQLyISLALGSTECILLADMALDR | CLL | CLL-7 | SEQ ID NO: 154 |
| 156 | OR2T27 | NP_001001824 | Receptor, GPCR | Y290 | AVSAFYTILTPMLNPLIySLR | B cell ALL | SEM | SEQ ID NO: 155 |
| 157 | OR2T29 | NP_001004694 | Receptor, GPCR | Y276 | DMMVSVFyTILTPVLNPLIYSLRNKDVMGALK | AML | MV4-11 | SEQ ID NO: 156 |
| 158 | OR2T29 | NP_001004694 | Receptor, GPCR | Y288 | DMMVSVFYTILTPVLNPLIySLRNKDVMGALK | AML | MV4-11 | SEQ ID NO: 157 |
| 159 | OR5P3 | NP_703146 | Receptor, GPCR | Y290 | SSYSTDQNKVVSVFYTVVIPMLNPLIySLR | CLL, T cell leukemia | Jurkat, MEC-1 | SEQ ID NO: 158 |
| 160 | OR7G1 | NP_001005192 | Receptor, GPCR | Y235 | MPSARGKyK | AML | CTV-1 | SEQ ID NO: 159 |
| 161 | OR9A4 | NP_001001656 | Receptor, GPCR | Y34 | yLVTLMGNTVIIMIVCVDKRL | B cell ALL | SEM | SEQ ID NO: 160 |
| 162 | JMJD1C | NP_004232 | Receptor, misc. | Y377 | yVSYISPLSAVSVMEDK | acute eosinophilic leukemia | EOL-1 | SEQ ID NO: 161 |
| 163 | JMJD1C | NP_004232 | Receptor, misc. | Y380 | YVSyISPLSAVSVMEDK | acute eosinophilic leukemia | EOL-1 | SEQ ID NO: 162 |
| 164 | LILRB4 | NP_006838 | Receptor, misc. | Y360 | QSPHDEDPQAVTyAK | AML | MV4-11 | SEQ ID NO: 163 |
| 165 | LILRB4 | NP_006838 | Receptor, misc. | Y442 | QKATEPPPSQEGASPAEPSVyATLAIH | AML | MV4-11 | SEQ ID NO: 164 |
| 166 | NRBF2 | NP_110386 | Receptor, misc. | Y143 | CLPEIQGIFDRDPDTLLyLLQQK | AML, T cell | Jurkat, MV4-11 | SEQ ID NO: 165 |
| 167 | ROBO1 | NP_002932 | Receptor, misc. | Y328 | VTAGDMGSyTCVAENMVGK | CLL | CLL-16 | SEQ ID NO: 166 |
| 168 | ROBO1 | NP_002932 | Receptor, misc. | Y932 | NGLTSTyAGIR | B cell ALL | SEM | SEQ ID NO: 167 |
| 169 | SCARB1 | NP_005496 | Receptor, misc. | Y490 | DKEAIQAySESLMTSAPK | AML, colon | HCT116, M-07e | SEQ ID NO: 168 |
| 170 | TREM1 | NP_061113 | Receptor, misc. | Y116 | MVNLQVEDSGLYQCVIyQPPK | acute eosinophilic leukemia | EOL-1 | SEQ ID NO: 169 |
| 171 | ARPP-19 | NP_006619 | RNA binding protein | Y36 | ARyPHLGQKPGGSDFLR | B cell ALL, CML | BaF3-Tel/FGFR3, SEM | SEQ ID NO: 170 |
| 172 | CASC3 | NP_031385 | RNA binding protein | Y181 | HLDDDEDRKNPAyIPR | B cell ALL | SEM | SEQ ID NO: 171 |
| 173 | CPSF6 | NP_008938 | RNA binding protein | Y76 | GAAPNVVYTyTGK | CML | K562 | SEQ ID NO: 172 |
| 174 | CPSF6 | NP_008938 | RNA binding protein | Y390 | GPPPTDPYGRPPPyDRGDYGPPGR | CLL | CLL23LB4 | SEQ ID NO: 173 |
| 175 | CPSF6 | NP_008938 | RNA binding protein | Y395 | GPPPTDPYGRPPPYDRGDyGPPGR | CLL | CLL23LB4 | SEQ ID NO: 174 |
| 176 | ELAVL1 | NP_001410 | RNA binding protein | Y200 | NVALLSQLyHSPAR | AML, B cell ALL, T cell | Jurkat, MKPL-1, SEM | SEQ ID NO: 175 |
| 177 | GEMIN4 | NP_056536 | RNA binding protein | Y343 | EWGEELQAVLRSSQGTSyDSYR | AML | MKPL-1 | SEQ ID NO: 176 |
| 178 | GRSF1 | NP_002083 | RNA binding protein | Y79 | SQESKTTYLEDLPPPPEyELAPSKLEEEVDDVF | T cell leukemia | Jurkat | SEQ ID NO: 177 |
| 179 | HNRPA0 | NP_006796 | RNA binding protein | Y145 | GFGFVyFQNHDAADKAAVVK | AML | MKPL-1 | SEQ ID NO: 178 |
| 180 | HNRPA1 | NP_002127 | RNA binding protein | Y167 | yHTVNGHNCEVR | AML | MKPL-1 | SEQ ID NO: 179 |
| 181 | HNRPA2B1 | NP_002128 | RNA binding protein | Y162 | yHTINGHNAEVR | AML, lymphoma | MKPL-1, SUPT-13 | SEQ ID NO: 180 |
| 182 | HNRPC | NP_004491 | RNA binding protein | Y124 | DYYDRMySYPAR | AML | CMK, MKPL-1 | SEQ ID NO: 181 |
| 183 | HNRPH2 | NP_062543 | RNA binding protein | Y240 | GAYGGGyGGYDDYGGYNDGYGFGSDR | T cell leukemia | Jurkat | SEQ ID NO: 182 |
| 184 | HNRPH2 | NP_062543 | RNA binding protein | Y249 | GAYGGGYGGYDDYGGyNDGYGFGSDR | T cell leukemia | Jurkat | SEQ ID NO: 183 |
| 185 | HNRPK | NP_002131 | RNA binding protein | Y380 | GSyGDLGGPIITTQVTIPK | AML, colon | HCT116, MKPL-1 | SEQ ID NO: 184 |
| 186 | HNRPUL1 | NP_008971 | RNA binding protein | Y124 | QNQFYDTQVIKQENESGyER | AML | MKPL-1 | SEQ ID NO: 185 |
| 187 | KHDRBS1 | NP_006550 | RNA binding protein | Y396 | SQSQGDSEyYDYGHGEVQDSY | T cell leukemia | Jurkat | SEQ ID NO: 186 |
| 188 | KHDRBS1 | NP_006550 | RNA binding protein | Y397 | GYYSQSQGDSEYyDYGHGE | T cell leukemia | Jurkat | SEQ ID NO: 187 |
| 189 | KHDRBS1 | NP_006550 | RNA binding protein | Y435 | GAyREHPYGRY | AML, B cell ALL | MKPL-1, SEM | SEQ ID NO: 188 |
| 190 | MATR3 | NP_061322 | RNA binding protein | Y171 | SATREPPyRVPR | AML | MKPL-1 | SEQ ID NO: 189 |
| 191 | MATR3 | NP_061322 | RNA binding protein | Y243 | CRDDSFFGETSHNyHKFDSEYER | AML | MKPL-1 | SEQ ID NO: 190 |
| 192 | MATR3 | NP_061322 | RNA binding protein | Y250 | CRDDSFFGETSHNYHKFDSEyER | AML | MKPL-1 | SEQ ID NO: 191 |
| 193 | NOB1P | NP_054781 | RNA binding protein | Y366 | QKTNVFAPDyIAGVSPFVENDISSR | B cell ALL | SEM | SEQ ID NO: 192 |
| 194 | NOLA1 | NP_061856 | RNA binding protein | Y149 | FYIDPyKLLPLQR | AML | MKPL-1 | SEQ ID NO: 193 |
| 195 | NXF1 | NP_006353 | RNA binding protein | Y75 | YNPyTTRPNR | B cell ALL | SEM | SEQ ID NO: 194 |
| 196 | PABPC3 | NP_112241 | RNA binding protein | Y54 | ICRDLITSGSSNyAYVNFQHTK | CML | K562 | SEQ ID NO: 195 |
| 197 | PABPC3 | NP_112241 | RNA binding protein | Y56 | ICRDLITSGSSNYAyVNFQHTK | CML | K562 | SEQ ID NO: 196 |
| 198 | PAI-RBP1 | AAH02488 | RNA binding protein | Y231 | GGSGSHNWGTVKDELTESPKyIQK | B cell ALL | SEM | SEQ ID NO: 197 |
| 199 | PCBP2 | NP_005007 | RNA binding protein | Y230 | GPPLEAyTIQGQYAIPQPD | T cell leukemia | Jurkat | SEQ ID NO: 198 |
| 200 | PRPF31 | NP_056444 | RNA binding protein | Y207 | HRIYEyVESR | AML | CMK | SEQ ID NO: 199 |
| 201 | PTBP2 | NP_067013 | RNA binding protein | Y127 | NQPIyIQYSNHK | AML | MKPL-1 | SEQ ID NO: 200 |
| 202 | RBM14 | NP_006319 | RNA binding protein | Y614 | LAELSDyR | AML | MKPL-1 | SEQ ID NO: 201 |
| 203 | RBM15 | NP_073605 | RNA binding protein | Y251 | IEAVyVSR | AML | MKPL-1 | SEQ ID NO: 202 |

FIGURE 2

| | A | B | C | D | E | F | G | H |
|---|---|---|---|---|---|---|---|---|
| 1 | Protein Name | Accession No. | Protein Type | Phospho-Residue | Phosphorylation Site Sequence | Disease | Cell Line / Tissue / Patient | SEQ ID NO |
| 204 | RBM22 | NP_060517 | RNA binding protein | Y116 | SDVNKEyYTQNMER | AML, B cell ALL | MKPL-1, SEM | SEQ ID NO: 203 |
| 205 | RBM3 | NP_006734 | RNA binding protein | Y143 | NQGGyDRYSGGNYRDNYDN | B cell ALL | SEM | SEQ ID NO: 204 |
| 206 | RBM3 | NP_006734 | RNA binding protein | Y151 | DYNGRNQGGYDRYSGGNyR | AML, B cell ALL, breast | MCF-10A(Y969F), PL21, SEM | SEQ ID NO: 205 |
| 207 | RBMX | NP_002130 | RNA binding protein | Y134 | GGHMDDGGySMNFNMSSSR | AML, B cell ALL, DLBCL, T cell leukemia | Jurkat, MKPL-1, OCI-ly12, SEM | SEQ ID NO: 206 |
| 208 | RBMX | NP_002130 | RNA binding protein | Y220 | DSySSRDYPSSR | B cell ALL | SEM | SEQ ID NO: 207 |
| 209 | RBMX | NP_002130 | RNA binding protein | Y255 | DYGHSSSRDDyPSR | AML, B cell ALL | MKPL-1, SEM | SEQ ID NO: 208 |
| 210 | RNASEH1 | NP_002927 | RNA binding protein | Y114 | EPLDGDGHESAEPyAKHMKPSVEPAPPVSR | T cell leukemia | Jurkat | SEQ ID NO: 209 |
| 211 | ROD1 | NP_005147 | RNA binding protein | Y127 | SQPVyIQYSNHR | AML, B cell ALL, CML, T | BaF3-Tel/FGFR3, MKPL-1, MOLT15, SEM | SEQ ID NO: 210 |
| 212 | RPL23A | NP_000975 | RNA binding protein | Y74 | LDHyAIIKFPLTTESAMK | anaplastic lymphoma, breast cancer | Karpas 299, MCF-10A(Y969F) | SEQ ID NO: 211 |
| 213 | RPL4 | NP_000959 | RNA binding protein | Y264 | KLDELyGTWR | T cell ALL, T cell leukemia | Jurkat, MOLT15 | SEQ ID NO: 212 |
| 214 | SF1 | NP_004621 | RNA binding protein | Y52 | EQERAyIVQLQIEDLTR | B cell ALL | SEM | SEQ ID NO: 213 |
| 215 | SF3A2 | NP_009096 | RNA binding protein | Y45 | QLALETIDINKDPyFMK | B cell ALL | SEM | SEQ ID NO: 214 |
| 216 | SFPQ | NP_005057 | RNA binding protein | Y527 | DAKDKLESEMEDAyHEHQANLLR | AML | MKPL-1 | SEQ ID NO: 215 |
| 217 | SFPQ | NP_005057 | RNA binding protein | Y698 | GREEyEGPNKKPR | AML, CML, T cell | Baf3-V617F-jak2, Jurkat, MKPL-1 | SEQ ID NO: 216 |
| 218 | SFRS10 | NP_004584 | RNA binding protein | Y128 | HVGNRANPDPNCCLGVFGLSLyTTER | CML, NSCLC | H1975, KCL22 | SEQ ID NO: 217 |
| 219 | SFRS2 | NP_003007 | RNA binding protein | Y44 | VGDVyIPR | AML | MKPL-1 | SEQ ID NO: 218 |
| 220 | SFRS3 | NP_003008 | RNA binding protein | Y32 | AFGyYGPLR | AML, T cell ALL, lymphoma | M-07e, MKPL-1, MOLT15, SUPT-13 | SEQ ID NO: 219 |
| 221 | SFRS6 | NP_006266 | RNA binding protein | Y191 | PRTSHRRSySGSRSR | AML | CMK | SEQ ID NO: 220 |
| 222 | SFRS9 | NP_003760 | RNA binding protein | Y214 | GSPHyFSPFRPY | AML, CLL, T cell ALL | CLL-10, CMK, DU-528, M-07e | SEQ ID NO: 221 |
| 223 | SR140 | XP_031553 | RNA binding protein | Y173 | AAAEIyEEFLAAFEGSDGNK | T cell leukemia | Jurkat | SEQ ID NO: 222 |
| 224 | XRN1 | NP_061874 | RNA binding protein | Y1248 | MQyFQPTIQEK | B cell ALL | SEM | SEQ ID NO: 223 |
| 225 | HNRPM | NP_005959 | RNA binding proteins | Y64 | GGNRFEPyANPTK | AML | CMK, M-07e, MKPL-1 | SEQ ID NO: 224 |
| 226 | HNRPM | NP_005959 | RNA binding proteins | Y681 | DKFNECGHVLyADIK | AML, lymphoma | MKPL-1, SUPT-13 | SEQ ID NO: 225 |
| 227 | AZGP1 | NP_001176 | Secreted protein | Y107 | DIVEyYNDSNGSHVLQGR | AML | PL21 | SEQ ID NO: 226 |
| 228 | FGF10 | NP_004456 | Secreted protein | Y70 | GQDMVSPEATNSSSSSFSSPSSAGRHVRSy | B cell ALL | SEM | SEQ ID NO: 227 |
| 229 | FRZB | NP_001454 | Secreted protein | Y197 | CKPIRATQKTYFRNNYNyVIR | CLL, NSCLC | CLL-9, H1975 | SEQ ID NO: 228 |
| 230 | MAML2 | NP_115803 | Transcription, coactivator/corepressor | Y513 | IPSPSFGQQTFSPQSSPMPGVAGGSGQSKVMANyMYK | myeloproliferative diseases | 293T-FGFR | SEQ ID NO: 229 |
| 231 | MAML2 | NP_115803 | Transcription, coactivator/corepressor | Y515 | IPSPSFGQQTFSPQSSPMPGVAGGSGQSKVMANYMyK | myeloproliferative diseases | 293T-FGFR | SEQ ID NO: 230 |
| 232 | SLB | NP_056477 | Transcription, coactivator/corepressor | Y222 | KIVAyGKEGHMLQTFDYSRDPQER | AML | CMK | SEQ ID NO: 231 |
| 233 | SUPT16H | NP_009123 | Transcription, coactivator/corepressor | Y1006 | KADRESRyEEEEEQSR | T cell leukemia | Jurkat | SEQ ID NO: 232 |
| 234 | UNC5CL | NP_775832 | Transcription, coactivator/corepressor | Y194 | PCTLTFKHCAEQPSHARTySSNTTLLDAKVWR | CML | K562 | SEQ ID NO: 233 |
| 235 | CNOT2 | NP_055330 | Transcription factor | Y37 | FVEGVDSDyHDENMYYSQSSMFPHR | T cell leukemia | Jurkat | SEQ ID NO: 234 |
| 236 | CNOT2 | NP_055330 | Transcription factor | Y43 | FVEGVDSDYHDENMyYSQSSMFPHR | T cell leukemia | Jurkat | SEQ ID NO: 235 |
| 237 | CNOT2 | NP_055330 | Transcription factor | Y44 | FVEGVDSDYHDENMyySQSSMFPHR | T cell leukemia | Jurkat | SEQ ID NO: 236 |
| 238 | FOXJ1 | NP_001445 | Transcription factor | Y148 | ITLSAIyKWITDNFCYFR | T cell leukemia | Jurkat | SEQ ID NO: 237 |
| 239 | FOXJ1 | NP_001445 | Transcription factor | Y157 | ITLSAIYKWITDNFCyFR | T cell leukemia | Jurkat | SEQ ID NO: 238 |
| 240 | IRF2BP1 | NP_056464 | Transcription factor | Y268 | VFAFDATARPPGyEFELK | AML | MKPL-1 | SEQ ID NO: 239 |

FIGURE 2

| | A | B | C | D | E | F | G | H |
|---|---|---|---|---|---|---|---|---|
| 1 | Protein Name | Accession No. | Protein Type | Phospho-Residue | Phosphorylation Site Sequence | Disease | Cell Line / Tissue / Patient | SEQ ID NO |
| 241 | LITAF | NP_004853 | Transcription factor | Y32 | NSyYPTPPAPMPGPT | AML | HT-93 | SEQ ID NO: 240 |
| 242 | LITAF | NP_004853 | Transcription factor | Y62 | TGLVTGPDGKGMNPPSYyTQPAPIPNNNPIT | AML | HT-93 | SEQ ID NO: 241 |
| 243 | SNAPC3 | NP_003075 | Transcription factor | Y157 | QETFVyEMESHAIGKK | CML | K562 | SEQ ID NO: 242 |
| 244 | SPDEF | NP_036523 | Transcription factor | Y312 | LSRSIRQyYKKGIIRKPDISQRLVYQFVHPI | T cell leukemia | Jurkat | SEQ ID NO: 243 |
| 245 | SPDEF | NP_036523 | Transcription factor | Y313 | LSRSIRQYyKKGIIRKPDISQRLVYQFVHPI | T cell leukemia | Jurkat | SEQ ID NO: 244 |
| 246 | ZHX2 | NP_055758 | Transcription factor | Y731 | KATKPMAESPKNGGDVVPQYyKDPK | T cell leukemia | Jurkat | SEQ ID NO: 245 |
| 247 | POLR3B | NP_060552 | Transcription initiation complex | Y714 | IDTLMYLLAyPQKPMVK | CLL | CLL-16 | SEQ ID NO: 246 |
| 248 | CSS3 | NP_787052 | Transferase | Y677 | GyQNKYPKAEMTLIPMKGEFSR | T cell leukemia | Jurkat | SEQ ID NO: 247 |
| 249 | GALNT4 | NP_003765 | Transferase | Y181 | TIHSVLETSPAVLLKEIILVDDLSDRVyLK | CML | K562 | SEQ ID NO: 248 |
| 250 | PARP3 | NP_001003931 | Transferase | Y420 | VGKGIyFASENSKSAGYVIGMK | CML | K562 | SEQ ID NO: 249 |
| 251 | PARP3 | NP_001003931 | Transferase | Y431 | VGKGIYFASENSKSAGyVIGMK | CML | K562 | SEQ ID NO: 250 |
| 252 | SLC27A1 | NP_940982 | Transporter, active | Y488 | GDSAyLSGDVLVMDELGYMYFR | T cell leukemia | Jurkat | SEQ ID NO: 251 |
| 253 | SLC27A1 | NP_940982 | Transporter, active | Y501 | GDSAYLSGDVLVMDELGyMYFR | CLL | CLL23LB4 | SEQ ID NO: 252 |
| 254 | SLC27A1 | NP_940982 | Transporter, active | Y503 | GDSAYLSGDVLVMDELGYMyFR | T cell leukemia | Jurkat | SEQ ID NO: 253 |
| 255 | SLC29A4 | NP_694979 | Transporter, active | Y198 | RyTQGVMTGESTAGVMISLSRILTK | CML | K562 | SEQ ID NO: 254 |
| 256 | SLC7A6 | AAH28216 | Transporter, active | Y13 | EPGRPTPTyHLVPNTSQSQVEEDVSSPPQR | B cell ALL | SEM | SEQ ID NO: 255 |
| 257 | SLC12A7 | NP_006589 | Transporter, facilitator | Y991 | LIAEKyR | T cell leukemia | Jurkat | SEQ ID NO: 256 |
| 258 | SLC26A1 | NP_602297 | Transporter, facilitator | Y191 | VATALTLMTGLyQTSWGR | CLL | CLL-16 | SEQ ID NO: 257 |
| 259 | SLC35B2 | NP_835361 | Transporter, facilitator | Y54 | MVPGyLLVQYF | B cell ALL | SEM | SEQ ID NO: 258 |
| 260 | SLC6A5 | NP_004202 | Transporter, facilitator | Y710 | yPNWSMVLGWLMLACSVIWIPIMFVIKMHLAPGR | AML | CMK | SEQ ID NO: 259 |
| 261 | RNF139 | NP_009149 | Ubiquitin conjugating pathway | Y450 | VIVSLTVYTLFMIDGYyNVLWEKLDDYVYYVR | DLBCL | OCI-ly12 | SEQ ID NO: 260 |
| 262 | UBE3B | NP_569733 | Ubiquitin conjugating pathway | Y695 | MLEDGyEQLRQLSQHAMK | AML | CMK | SEQ ID NO: 261 |
| 263 | USP15 | NP_006304 | Ubiquitin conjugating pathway | Y234 | NSNyCLPSYTAYKNYDYSEPGR | T cell leukemia | Jurkat | SEQ ID NO: 262 |
| 264 | USP15 | NP_006304 | Ubiquitin conjugating pathway | Y245 | NSNYCLPSYTAYKNyDYSEPGR | T cell leukemia | Jurkat | SEQ ID NO: 263 |
| 265 | USP15 | NP_006304 | Ubiquitin conjugating pathway | Y247 | NSNYCLPSYTAYKNYDySEPGR | T cell leukemia | Jurkat | SEQ ID NO: 264 |
| 266 | USP25 | NP_037528 | Ubiquitin conjugating pathway | Y740 | ESETSVTTAQAAGDPEyLEQPSRSDFSK | DLBCL, T cell leukemia | Jurkat, SU-DHL4 | SEQ ID NO: 265 |
| 267 | USP3 | NP_006528 | Ubiquitin conjugating pathway | Y383 | SFTDLEELDETELyMCHKCKK | T cell leukemia | Jurkat | SEQ ID NO: 266 |
| 268 | USP38 | NP_115946 | Ubiquitin conjugating pathway | Y987 | LyLQEQELNARAR | DLBCL | OCI-ly1 | SEQ ID NO: 267 |
| 269 | USP48 | NP_115612 | Ubiquitin conjugating pathway | Y575 | ILRLKNQLNEDyKTVNNLLK | AML | CMK | SEQ ID NO: 268 |
| 270 | CACYBP | NP_001007215 | Ubiquitin conjugating system | Y28 | KAELLDNEKPAAVVAPITTGyTVK | B cell ALL, SCLC | H69, SEM | SEQ ID NO: 269 |
| 271 | CUL7 | NP_055595 | Ubiquitin conjugating system | Y786 | CEKHAHLyRKLITNILGGCIQMVLGQIEDHR | T cell leukemia | Jurkat | SEQ ID NO: 270 |
| 272 | HACE1 | NP_065822 | Ubiquitin conjugating system | Y677 | HILGIPVNyQDVASIDPEYAK | CLL | M01043 | SEQ ID NO: 271 |
| 273 | HACE1 | NP_065822 | Ubiquitin conjugating system | Y687 | HILGIPVNYQDVASIDPEyAK | CLL | M01043 | SEQ ID NO: 272 |
| 274 | RNF25 | NP_071898 | Ubiquitin conjugating system | Y432 | TPGSSyPR | B cell ALL | SEM | SEQ ID NO: 273 |
| 275 | CLTA | NP_001824 | Vesicle protein | Y83 | DGGAPGPQPHGEPPGGPDAVDGVMNGEyYQESNGPTD | T cell leukemia | Jurkat | SEQ ID NO: 274 |
| 276 | CLTA | NP_001824 | Vesicle protein | Y84 | GGAPGPQPHGEPPGGPDAVDGVMNGEYyQE | T cell leukemia | Jurkat | SEQ ID NO: 275 |
| 277 | COPB2 | NP_004757 | Vesicle protein | Y354 | DMGSCEIyPQTIQHNPNGR | AML, T cell ALL | CTV-1, MOLT15 | SEQ ID NO: 276 |
| 278 | HPS3 | NP_115759 | Vesicle protein | Y922 | CPEAVIPyANHELKEENR | AML | CMK | SEQ ID NO: 277 |
| 279 | NSF | NP_006169 | Vesicle protein | Y45 | yTFTLKTHPSVVPGSIAFSLPQRK | T cell leukemia | Jurkat | SEQ ID NO: 278 |
| 280 | SCAMP3 | NP_005689 | Vesicle protein | Y41 | QYATLDVyNPFETR | T cell leukemia | Jurkat | SEQ ID NO: 279 |
| 281 | SNAP23 | NP_003816 | Vesicle protein | Y139 | QPGPVTNGQLQQPTTGAASGGyIK | AML, B cell ALL, T cell leukemia, breast | Jurkat, M-07e, MCF-10A (Y561F), SEM | SEQ ID NO: 280 |
| 282 | SNAP29 | NP_004773 | Vesicle protein | Y122 | SVFGGLVNyFK | B cell ALL | SEM | SEQ ID NO: 281 |

FIGURE 2

|   | A | B | C | D | E | F | G | H |
|---|---|---|---|---|---|---|---|---|
| 1 | Protein Name | Accession No. | Protein Type | Phospho-Residue | Phosphorylation Site Sequence | Disease | Cell Line / Tissue / Patient | SEQ ID NO |
| 283 | SNAP29 | NP_004773 | Vesicle protein | Y189 | GAGSAMSTDAyPKNPHLR | B cell ALL | SEM | SEQ ID NO: 282 |
| 284 | STX1A | NP_004594 | Vesicle protein | Y141 | FVEVMSEYNATQSDyRER | T cell leukemia | Jurkat | SEQ ID NO: 283 |
| 285 | SV2A | NP_055664 | Vesicle protein | Y41 | GLDRVQDEySR | T cell leukemia | Jurkat | SEQ ID NO: 284 |
| 286 | VPS13B | NP_060360 | Vesicle protein | Y1453 | LLDGTHQQHGFLSLTyTK | CLL | CLL-9 | SEQ ID NO: 285 |
| 287 | VPS41 | NP_055211 | Vesicle protein | Y518 | KDSQNKTLLKTLAELyTYDK | CLL | CLL-19 | SEQ ID NO: 286 |
| 288 | VPS41 | NP_055211 | Vesicle protein | Y520 | KDSQNKTLLKTLAELYTyDK | CLL | CLL-19 | SEQ ID NO: 287 |
| 289 | VTI1B | NP_006361 | Vesicle protein | Y115 | YGIyAVENEHMNR | NSCLC, T cell ALL | H3255, MOLT15 | SEQ ID NO: 288 |
| 290 | | | | | | | | |

FIGURE 3B.

PTSIPPKEETPpYIAQVFQQK

| Seq | # | b | y | (+1) |
|---|---|---|---|---|
| P | 1 | 98.1 | 2483.7 | 21 |
| T | 2 | 199.2 | 2386.6 | 20 |
| S | 3 | 286.3 | 2285.5 | 19 |
| I | 4 | 399.5 | 2198.4 | 18 |
| P | 5 | 496.6 | 2085.3 | 17 |
| P | 6 | 593.7 | 1988.2 | 16 |
| K | 7 | 721.9 | 1891.0 | 15 |
| E | 8 | 851.0 | 1762.9 | 14 |
| E | 9 | 980.1 | 1633.8 | 13 |
| T | 10 | 1081.2 | 1504.6 | 12 |
| T | 11 | 1182.3 | 1403.5 | 11 |
| P | 12 | 1279.4 | 1302.4 | 10 |
| Y* | 13 | 1522.6 | 1205.3 | 9 |
| I | 14 | 1635.8 | 962.1 | 8 |
| A | 15 | 1706.8 | 849.0 | 7 |
| Q | 16 | 1835.0 | 777.9 | 6 |
| V | 17 | 1934.1 | 649.8 | 5 |
| F | 18 | 2081.3 | 550.6 | 4 |
| Q | 19 | 2209.4 | 403.5 | 3 |
| Q | 20 | 2337.5 | 275.3 | 2 |
| K | 21 | 2465.7 | 147.2 | 1 |

| Seq | # | b | y | (+2) |
|---|---|---|---|---|
| P | 1 | 49.6 | 1242.4 | 21 |
| T | 2 | 100.1 | 1193.8 | 20 |
| S | 3 | 143.7 | 1143.3 | 19 |
| I | 4 | 200.2 | 1099.7 | 18 |
| P | 5 | 248.8 | 1043.1 | 17 |
| P | 6 | 297.4 | 994.6 | 16 |
| K | 7 | 361.4 | 946.0 | 15 |
| E | 8 | 426.0 | 881.9 | 14 |
| E | 9 | 490.6 | 817.4 | 13 |
| T | 10 | 541.1 | 752.8 | 12 |
| T | 11 | 591.7 | 702.3 | 11 |
| P | 12 | 640.2 | 651.7 | 10 |
| Y* | 13 | 761.8 | 603.2 | 9 |
| I | 14 | 818.4 | 481.6 | 8 |
| A | 15 | 853.9 | 425.0 | 7 |
| Q | 16 | 918.0 | 389.5 | 6 |
| V | 17 | 967.6 | 325.4 | 5 |
| F | 18 | 1041.1 | 275.8 | 4 |
| Q | 19 | 1105.2 | 202.2 | 3 |
| Q | 20 | 1169.3 | 138.2 | 2 |
| K | 21 | 1233.4 | 74.1 | 1 |

SLYQSAGVAPESFEpYIEAHGTGTK

| Seq # | | b | y | (+2) |
|---|---|---|---|---|
| 1 | S | 44.5 | 1312.4 | 24 |
| 2 | L | 101.1 | 1268.8 | 23 |
| 3 | Y | 182.7 | 1212.3 | 22 |
| 4 | Q | 246.8 | 1130.7 | 21 |
| 5 | S | 290.3 | 1066.6 | 20 |
| 6 | A | 325.4 | 1023.1 | 19 |
| 7 | G | 354.4 | 987.5 | 18 |
| 8 | V | 404.0 | 959.0 | 17 |
| 9 | A | 439.5 | 909.4 | 16 |
| 10 | P | 488.0 | 873.9 | 15 |
| 11 | E | 552.6 | 825.3 | 14 |
| 12 | S | 596.1 | 760.8 | 13 |
| 13 | F | 669.7 | 717.2 | 12 |
| 14 | E | 734.3 | 643.7 | 11 |
| 15 | Y* | 855.9 | 579.1 | 10 |
| 16 | I | 912.5 | 457.5 | 9 |
| 17 | E | 977.0 | 400.9 | 8 |
| 18 | A | 1012.6 | 336.4 | 7 |
| 19 | H | 1081.1 | 300.8 | 6 |
| 20 | G | 1109.7 | 232.3 | 5 |
| 21 | T | 1160.2 | 203.7 | 4 |
| 22 | G | 1188.7 | 153.2 | 3 |
| 23 | T | 1239.3 | 124.7 | 2 |
| 24 | K | 1303.4 | 74.1 | 1 |

FIGURE 4B.

| seq # | | b | y | (+1) |
|---|---|---|---|---|
| 1 | S | 88.1 | 2623.7 | 24 |
| 2 | L | 201.2 | 2536.7 | 23 |
| 3 | Y | 364.4 | 2423.5 | 22 |
| 4 | Q | 492.6 | 2260.3 | 21 |
| 5 | S | 579.6 | 2132.2 | 20 |
| 6 | A | 650.7 | 2045.1 | 19 |
| 7 | G | 707.8 | 1974.0 | 18 |
| 8 | V | 806.9 | 1917.0 | 17 |
| 9 | A | 878.0 | 1817.9 | 16 |
| 10 | P | 975.1 | 1746.8 | 15 |
| 11 | E | 1104.2 | 1649.7 | 14 |
| 12 | S | 1191.3 | 1520.6 | 13 |
| 13 | F | 1338.5 | 1433.5 | 12 |
| 14 | E | 1467.6 | 1286.6 | 11 |
| 15 | Y* | 1710.8 | 1157.2 | 10 |
| 16 | I | 1823.9 | 914.0 | 9 |
| 17 | E | 1953.0 | 800.8 | 8 |
| 18 | A | 2024.1 | 671.7 | 7 |
| 19 | H | 2161.2 | 600.7 | 6 |
| 20 | G | 2218.3 | 463.5 | 5 |
| 21 | T | 2319.4 | 406.4 | 4 |
| 22 | G | 2376.5 | 305.4 | 3 |
| 23 | T | 2477.6 | 248.3 | 2 |
| 24 | K | 2605.7 | 147.2 | 1 |

FIGURE 7B.

HSSLIDIDSVPTpYKWK

| Seq # | | b | y | (+2) |
|---|---|---|---|---|
| H | 1 | 69.6 | 985.6 | 16 |
| S | 2 | 113.1 | 917.0 | 15 |
| S | 3 | 156.7 | 873.5 | 14 |
| L | 4 | 213.2 | 829.9 | 13 |
| I | 5 | 269.8 | 773.3 | 12 |
| D | 6 | 327.4 | 716.8 | 11 |
| I | 7 | 383.9 | 659.2 | 10 |
| D | 8 | 441.5 | 602.6 | 9 |
| S | 9 | 485.0 | 545.1 | 8 |
| V | 10 | 534.6 | 501.6 | 7 |
| P | 11 | 583.1 | 452.0 | 6 |
| T | 12 | 633.7 | 403.4 | 5 |
| Y* | 13 | 755.3 | 352.9 | 4 |
| K | 14 | 819.4 | 231.3 | 3 |
| W | 15 | 912.5 | 167.2 | 2 |
| K | 16 | 976.6 | 74.1 | 1 |

| Seq | # | b | y | (+1) |
|---|---|---|---|---|
| H | 1 | 138.1 | 1970.1 | 16 |
| S | 2 | 225.2 | 1833.0 | 15 |
| S | 3 | 312.3 | 1745.9 | 14 |
| L | 4 | 425.5 | 1658.8 | 13 |
| I | 5 | 538.6 | 1545.7 | 12 |
| D | 6 | 653.7 | 1432.5 | 11 |
| I | 7 | 766.9 | 1317.4 | 10 |
| D | 8 | 882.0 | 1204.3 | 9 |
| S | 9 | 969.0 | 1089.2 | 8 |
| V | 10 | 1068.2 | 1002.1 | 7 |
| P | 11 | 1165.3 | 903.0 | 6 |
| T | 12 | 1266.4 | 805.9 | 5 |
| Y* | 13 | 1509.6 | 704.8 | 4 |
| K | 14 | 1637.7 | 461.6 | 3 |
| W | 15 | 1824.0 | 333.4 | 2 |
| K | 16 | 1952.1 | 147.2 | 1 |

IEAVpYVSR

| Seq | # | b | y | (+1) |
|---|---|---|---|---|
| I | 1 | 114.2 | 1017.1 | 8 |
| E | 2 | 243.3 | 903.9 | 7 |
| A | 3 | 314.4 | 774.8 | 6 |
| V | 4 | 413.5 | 703.7 | 5 |
| Y* | 5 | 656.7 | 604.6 | 4 |
| V | 6 | 755.8 | 361.4 | 3 |
| S | 7 | 842.9 | 262.3 | 2 |
| R | 8 | 999.1 | 175.2 | 1 |

US 7,888,480 B2

SEQUENCE LISTING

<160> NUMBER OF SEQ ID NOS: 288

<210> SEQ ID NO 1
<211> LENGTH: 25
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION: tyrosine at position 12 is
      phosphorylated

<400> SEQUENCE: 1

Ile His Asn Gly Ser Ser Glu Ala Leu Ser Gln Tyr Lys Met Asn Ile
1               5                   10                  15

Thr Ser Ile Ala Pro Leu Leu Glu Lys
            20                  25

<210> SEQ ID NO 2
<211> LENGTH: 18
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION: tyrosine at position 3 is
      phosphorylated

<400> SEQUENCE: 2

Asn Met Tyr Arg Leu Ala Met Thr Gly Ala Gly Ile Asp Arg His Leu
1               5                   10                  15

Phe Cys

<210> SEQ ID NO 3
<211> LENGTH: 13
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION; tyrosine at position 10 is
      phosphorylated

<400> SEQUENCE: 3

Glu Glu Leu Glu Ala Leu Phe Leu Pro Tyr Asp Leu Lys
1               5                   10

<210> SEQ ID NO 4
<211> LENGTH: 19
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 4

```
Arg Ile Pro Asp Asp Pro Asp Tyr Ser Val Val Glu Asp Tyr Ser Leu
1               5                   10                  15

Leu Tyr Gln

<210> SEQ ID NO 5
<211> LENGTH: 19
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: PHOSPHORYLATION; tyrosine at position 18 is
      phosphorylated

<400> SEQUENCE: 5

Arg Ile Pro Asp Asp Pro Asp Tyr Ser Val Val Glu Asp Tyr Ser Leu
1               5                   10                  15

Leu Tyr Gln

<210> SEQ ID NO 6
<211> LENGTH: 16
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 6

Pro Asn Glu Phe Asp Lys Tyr Arg Met Phe Ile Gly Asp Leu Asp Lys
1               5                   10                  15

<210> SEQ ID NO 7
<211> LENGTH: 15
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; tyrosine at position 3 is
      phosphorylated

<400> SEQUENCE: 7

Asp Asp Tyr Tyr Ser Asn Thr Leu His Asp Thr Gly Asp Lys Glu
1               5                   10                  15

<210> SEQ ID NO 8
<211> LENGTH: 15
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; tyrosine at position 4 is
      phosphorylated

<400> SEQUENCE: 8

Asp Asp Tyr Tyr Ser Asn Thr Leu His Asp Thr Gly Asp Lys Glu
1               5                   10                  15

<210> SEQ ID NO 9
<211> LENGTH: 21
<212> TYPE: PRT
<213> ORGANISM: Homo sapiens
<220> FEATURE:
<221> NAME/KEY: MOD_RES
<222> LOCATION: (13)..(13)
```

```
<223> OTHER INFORMATION: PHOSPHORYLATION; tyrosine at position 13 is
      phosphorylated

<400> SEQUENCE: 9

Pro Thr Ser Ile Pro Pro Lys Glu Glu Thr Thr Pro Tyr Ile Ala Gln
1               5                  10                  15

Val Phe Gln Gln Lys
            20

<210> SEQ ID NO 10
<211> LENGTH: 16
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION; tyrosine at position 12 is
      phosphorylated

<400> SEQUENCE: 10

Thr Leu Leu Glu Asn Lys Asp Ser Gln Val Ile Tyr Ser Ser Val Lys
1               5                  10                  15

<210> SEQ ID NO 11
<211> LENGTH: 17
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION; tyrosine at position 12 is
      phosphorylated

<400> SEQUENCE: 11

Gly Arg Ala His Glu Glu Asp Asp Glu Glu Asn Tyr Glu Asn Val Pro
1               5                  10                  15

Arg

<210> SEQ ID NO 12
<211> LENGTH: 34
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; tyrosine at position 3 is
      phosphorylated

<400> SEQUENCE: 12

Gln Gly Tyr Tyr Leu Gln Met His Pro Asp Gly Ala Leu Asp Gly Thr
1               5                  10                  15

Lys Asp Asp Ser Thr Asn Ser Thr Leu Phe Asn Leu Ile Pro Val Gly
            20                  25                  30

Leu Arg

<210> SEQ ID NO 13
<211> LENGTH: 34
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; tyrosine at position 4 is
      phosphorylated

<400> SEQUENCE: 13
```

Gln Gly Tyr Tyr Leu Gln Met His Pro Asp Gly Ala Leu Asp Gly Thr
1               5                   10                  15

Lys Asp Asp Ser Thr Asn Ser Thr Leu Phe Asn Leu Ile Pro Val Gly
                20                  25                  30

Leu Arg

<210> SEQ ID NO 14
<211> LENGTH: 20
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: PHOSPHORYLATION; tyrosine at position 13 is
      phosphorylated

<400> SEQUENCE: 14

His Arg Glu Glu Met Ser Asn Glu Asp Ser Ser Asp Tyr Glu Asn Val
1               5                   10                  15

Leu Thr Ala Lys
            20

<210> SEQ ID NO 15
<211> LENGTH: 15
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at position 9 is
      phosphorylated

<400> SEQUENCE: 15

Ser Asp Lys Gln Tyr Ala Glu Asn Tyr Thr Arg Pro Ser Ser Arg
1               5                   10                  15

<210> SEQ ID NO 16
<211> LENGTH: 15
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; tyrosine at position 3 is
      phosphorylated

<400> SEQUENCE: 16

Asp Ile Tyr Asp Leu Lys Asp Gln Ile Gln Asp Val Glu Gly Arg
1               5                   10                  15

<210> SEQ ID NO 17
<211> LENGTH: 27
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: PHOSPHORYLATION; tyrosine at position 13 is
      phosphorylated

<400> SEQUENCE: 17

Gly Pro His Phe Asn Pro Ser Ala Ile His Asn Phe Tyr Asp Asn Ile
1               5                   10                  15

Gly Phe Val Gly Pro Val Pro Pro Lys Pro Lys
                20                  25

```
<210> SEQ ID NO 18
<211> LENGTH: 26
<212> TYPE: PRT
<213> ORGANISM: Homo sapiens
<220> FEATURE:
<221> NAME/KEY: MOD_RES
<222> LOCATION: (24)..(24)
<223> OTHER INFORMATION: PHOSPHORYLATION; tyrosine at position 24 is
      phosphorylated

<400> SEQUENCE: 18

Ala Ile Ser Glu Asp Ser Gly Cys Asp Ser Val Thr Asp Thr Glu Pro
1               5                   10                  15

Glu Asp Glu Lys Val Val Ser Tyr Ser Lys
            20                  25

<210> SEQ ID NO 19
<211> LENGTH: 18
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 19

Glu Met Asp Asp Glu Glu Tyr Ser Cys Ile Ala Leu Gly Glu Pro Leu
1               5                   10                  15

Tyr Arg

<210> SEQ ID NO 20
<211> LENGTH: 18
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: PHOSPHORYLATION; tyrosine at position 17 is
      phosphorylated

<400> SEQUENCE: 20

Glu Met Asp Asp Glu Glu Tyr Ser Cys Ile Ala Leu Gly Glu Pro Leu
1               5                   10                  15

Tyr Arg

<210> SEQ ID NO 21
<211> LENGTH: 18
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: PHOSPHORYLATION; tyrosiine at position 16 is
      phosphorylated

<400> SEQUENCE: 21

Gly Leu Asn Thr Asp Glu Leu Gly Gln Lys Glu Glu Ala Lys Asn Tyr
1               5                   10                  15

Tyr Lys

<210> SEQ ID NO 22
<211> LENGTH: 34
<212> TYPE: PRT
<213> ORGANISM: Homo sapiens
<220> FEATURE:
<221> NAME/KEY: MOD_RES
```

```
<222> LOCATION: (31)..(31)
<223> OTHER INFORMATION: PHOSPHORYLATION; tyrosine at position 31 is
      phosphorylated

<400> SEQUENCE: 22

Asp Val Tyr Arg Ala Glu Ile Ser Glu Phe Ala Pro Pro Asn Thr Pro
1               5                   10                  15

Val Val Met Val Lys Ala Ile Pro Ala Tyr Ser His Leu Arg Tyr Val
            20                  25                  30

Phe Lys

<210> SEQ ID NO 23
<211> LENGTH: 26
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PHOSPHORYLATION; tyrosine at position 1 is
      phosphorylated

<400> SEQUENCE: 23

Tyr His Leu Lys Val Ile Ala Arg Asp Gly Gly Thr Pro Ser Leu Gln
1               5                   10                  15

Ser Glu Glu Glu Val Leu Val Thr Val Arg
            20                  25

<210> SEQ ID NO 24
<211> LENGTH: 24
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated

<400> SEQUENCE: 24

Asp Cys Arg Ala Val Tyr Asp Arg Tyr Ser Asp Asp Phe Cys Ser Gly
1               5                   10                  15

His Gly Gln Cys Asn Cys Gly Arg
            20

<210> SEQ ID NO 25
<211> LENGTH: 24
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at position 9 is
      phosphorylated

<400> SEQUENCE: 25

Asp Cys Arg Ala Val Tyr Asp Arg Tyr Ser Asp Asp Phe Cys Ser Gly
1               5                   10                  15

His Gly Gln Cys Asn Cys Gly Arg
            20

<210> SEQ ID NO 26
<211> LENGTH: 33
<212> TYPE: PRT
<213> ORGANISM: Homo sapiens
<220> FEATURE:
<221> NAME/KEY: MOD_RES
<222> LOCATION: (19)..(19)
```

```
<223> OTHER INFORMATION: PHOSPHORYLATION; tyrosine at position 19 is
      phosphorylated

<400> SEQUENCE: 26

Ile Thr Thr Gln Ile Thr Ala Gly Ala Arg Asn Leu Asp Leu Lys Ser
1               5                   10                  15

Asp Leu Tyr Ile Gly Gly Val Ala Lys Glu Thr Tyr Lys Ser Leu Pro
            20                  25                  30

Lys

<210> SEQ ID NO 27
<211> LENGTH: 33
<212> TYPE: PRT
<213> ORGANISM: Homo sapiens
<220> FEATURE:
<221> NAME/KEY: MOD_RES
<222> LOCATION: (28)..(28)
<223> OTHER INFORMATION: PHOSPHORYLATION; tyrosine at position 28 is
      phosphorylated

<400> SEQUENCE: 27

Ile Thr Thr Gln Ile Thr Ala Gly Ala Arg Asn Leu Asp Leu Lys Ser
1               5                   10                  15

Asp Leu Tyr Ile Gly Gly Val Ala Lys Glu Thr Tyr Lys Ser Leu Pro
            20                  25                  30

Lys

<210> SEQ ID NO 28
<211> LENGTH: 19
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; tyrosine at position 3 is
      phosphorylated

<400> SEQUENCE: 28

Phe Leu Tyr Asp Leu Leu Gln Leu Pro Lys Gly Val Glu Pro Pro Ala
1               5                   10                  15

Glu Glu Glu

<210> SEQ ID NO 29
<211> LENGTH: 12
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION; tyrosine at position 5 is
      phosphorylated

<400> SEQUENCE: 29

Asp Gly Arg Lys Tyr Pro Glu Leu Val Leu Asp Lys
1               5                   10

<210> SEQ ID NO 30
<211> LENGTH: 24
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated
```

```
<400> SEQUENCE: 30

Glu Gln Thr Pro Glu Tyr Asn Val Thr Ile Val Ala Thr Asp Arg Gly
1               5                   10                  15

Lys Pro Pro Leu Ser Ser Ser Arg
            20

<210> SEQ ID NO 31
<211> LENGTH: 24
<212> TYPE: PRT
<213> ORGANISM: Homo sapiens
<220> FEATURE:
<221> NAME/KEY: MOD_RES
<222> LOCATION: (22)..(22)
<223> OTHER INFORMATION: PHOSPHORYLATION; tyrosine at position 22 is
      phosphorylated

<400> SEQUENCE: 31

Leu Leu Ala Gly Thr Val Ala Val Phe Leu Ile Leu Val Ala Val Leu
1               5                   10                  15

Thr Val Phe Phe Leu Tyr Asn Arg
            20

<210> SEQ ID NO 32
<211> LENGTH: 20
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: PHOSPHORYLATION; tyrosine at position 17 is
      phosphorylated

<400> SEQUENCE: 32

Lys Ser Pro Gly Gly Ala Gly Gly Gly Ala Ser Gly Asp Gly Gly Phe
1               5                   10                  15

Tyr Asp Pro Lys
            20

<210> SEQ ID NO 33
<211> LENGTH: 13
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at position 9 is
      phosphorylated

<400> SEQUENCE: 33

Gly Gln Glu Ala Thr Asp Thr Glu Tyr Ser Glu Ile Lys
1               5                   10

<210> SEQ ID NO 34
<211> LENGTH: 10
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 34

Glu Gly Asp Pro Ala Ile Tyr Ala Glu Arg
1               5                   10
```

```
<210> SEQ ID NO 35
<211> LENGTH: 23
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION; tyrosine at position 5 is
      phosphorylated

<400> SEQUENCE: 35

Lys Asp Asp Phe Tyr Tyr Leu Ser Gln Glu Asp Lys Glu Arg Gln Lys
1               5                   10                  15

Arg Glu His Glu Glu Ser Lys
            20

<210> SEQ ID NO 36
<211> LENGTH: 23
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated

<400> SEQUENCE: 36

Lys Asp Asp Phe Tyr Tyr Leu Ser Gln Glu Asp Lys Glu Arg Gln Lys
1               5                   10                  15

Arg Glu His Glu Glu Ser Lys
            20

<210> SEQ ID NO 37
<211> LENGTH: 10
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated

<400> SEQUENCE: 37

Gly Asp Lys Ala Ala Tyr Asp Ile Leu Arg
1               5                   10

<210> SEQ ID NO 38
<211> LENGTH: 26
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: PHOSPHORYLATION; tyrosine at position 16 is
      phosphorylated

<400> SEQUENCE: 38

Ser Thr Gly Val Val Asn Ile Pro Ala Ala Glu Cys Leu Asp Glu Tyr
1               5                   10                  15

Glu Asp Asp Glu Ala Gly Gln Lys Glu Arg
            20                  25

<210> SEQ ID NO 39
<211> LENGTH: 18
<212> TYPE: PRT
<213> ORGANISM: Homo sapiens
<220> FEATURE:
<221> NAME/KEY: MOD_RES
```

```
<222> LOCATION: (16)..(16)
<223> OTHER INFORMATION: PHOSPHORYLATION; tyrosine at position 16 is
      phosphorylated

<400> SEQUENCE: 39

Tyr Lys Ser Thr Thr Ser Val Ser Glu Glu Asp Val Ser Arg Tyr
1               5                   10                  15

Ser Arg

<210> SEQ ID NO 40
<211> LENGTH: 20
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION tyrosine at position 6 is
      phosphorylated

<400> SEQUENCE: 40

Asn Asp Ser Gly Thr Tyr Leu Cys Gly Ala Ile Ser Leu Ala Pro Lys
1               5                   10                  15

Ala Gln Ile Lys
            20

<210> SEQ ID NO 41
<211> LENGTH: 19
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION; tyrosine at position 11 is
      phosphorylated

<400> SEQUENCE: 41

Pro Ala Ser Gln Pro Pro Tyr Asn Pro Ala Tyr Met Asp Ala Pro Lys
1               5                   10                  15

Ala Ala Leu

<210> SEQ ID NO 42
<211> LENGTH: 21
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: PHOSPHORYLATION; tyrosine at position 18 is
      phosphorylated

<400> SEQUENCE: 42

Ile Ala Thr Cys Asn Gly Glu Gln Thr Gln Asn Arg Glu Pro Glu Ser
1               5                   10                  15

Pro Tyr Gly Gln Arg
            20

<210> SEQ ID NO 43
<211> LENGTH: 16
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION: tyrosine at position 5 is
      phosphorylated
<220> FEATURE:
<221> NAME/KEY: MOD_RES
```

```
<222> LOCATION: (5)..(5)
<223> OTHER INFORMATION: PHOSPHORYLATION; tyrosine at position 5 is
      phosphorylated

<400> SEQUENCE: 43

Glu Glu Leu His Tyr Ala Ser Val Val Phe Asp Ser Asn Thr Asn Arg
1               5                   10                  15

<210> SEQ ID NO 44
<211> LENGTH: 19
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: PHOSPHORYLATION; tyrosine at position 15 is
      phosphorylated

<400> SEQUENCE: 44

Ile Ala Ala Gln Arg Pro Arg Glu Glu Glu Pro Asp Ser Asp Tyr Ser
1               5                   10                  15

Val Ile Arg

<210> SEQ ID NO 45
<211> LENGTH: 10
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 45

Asp Ser Gln Met Gln Asn Pro Tyr Ser Arg
1               5                   10

<210> SEQ ID NO 46
<211> LENGTH: 15
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 46

Asp Val Gly His Asn Ile Tyr Ile Leu Ala His Gln Leu Ala Arg
1               5                   10                  15

<210> SEQ ID NO 47
<211> LENGTH: 23
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: PHOSPHORYLATION; tyrosine at position 14 is
      phosphorylated

<400> SEQUENCE: 47

Asp Phe Gly Gln Leu Ala Val Glu Leu Leu Asp Gln Ser Tyr Lys Gln
1               5                   10                  15

Asp Glu Gln Leu Ala Met Lys
            20
```

```
<210> SEQ ID NO 48
<211> LENGTH: 25
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: PHOSPHORYLATION; tyrosine at position 18 is
      phosphorylated

<400> SEQUENCE: 48

Ser His Leu Ile Lys Ala Thr Val Ile Pro Asn Arg Val Lys Met Leu
1               5                   10                  15

Pro Tyr Phe Gly Ile Ile Arg Asn Arg
            20                  25

<210> SEQ ID NO 49
<211> LENGTH: 20
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: PHOSPHORYLATION; tyrosine at position 17 is
      phosphorylated

<400> SEQUENCE: 49

Val Leu Gln Ala Gln Gly Ser Ser Asp Pro Glu Glu Glu Ser Val Leu
1               5                   10                  15

Tyr Ser Asn Arg
            20

<210> SEQ ID NO 50
<211> LENGTH: 18
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: PHOSPHORYLATION; tyrosine at position 14 is
      phosphorylated

<400> SEQUENCE: 50

Lys Thr Ser Phe Met Met Ala Leu Cys Leu Ser Ser Ile Tyr Glu Asp
1               5                   10                  15

Leu Lys

<210> SEQ ID NO 51
<211> LENGTH: 13
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 51

Tyr Asn Val Ser Thr Thr Pro Tyr Leu Gln Ser Val Lys
1               5                   10

<210> SEQ ID NO 52
<211> LENGTH: 23
<212> TYPE: PRT
<213> ORGANISM: Homo sapiens
<220> FEATURE:
<221> NAME/KEY: MOD_RES
<222> LOCATION: (17)..(17)
```

```
<223> OTHER INFORMATION: PHOSPHORYLATION; tyrosine at position 17 is
      phosphorylated

<400> SEQUENCE: 52

Glu Thr Asp Ala Phe Val Cys Arg Pro Asn Ala Ala Leu Cys Arg Val
1               5                   10                  15

Tyr Tyr Glu Ala Asp Thr Thr
            20

<210> SEQ ID NO 53
<211> LENGTH: 31
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: PHOSPHORYLATION; tyrosine at position 18 is
      phosphorylated

<400> SEQUENCE: 53

Arg Asp His Arg Pro Glu Lys Gln Pro Ser Arg Ile Pro Arg Pro Leu
1               5                   10                  15

Ala Tyr Val Phe Leu Gly Pro Ala Arg Gln Pro Pro Lys Asp Arg
            20                  25                  30

<210> SEQ ID NO 54
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 54

Lys Lys Glu Asp Asp Asp His Tyr Phe Val Met Thr Gly Ser Lys
1               5                   10                  15

<210> SEQ ID NO 55
<211> LENGTH: 17
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; tyrosine at position 4 is
      phosphorylated

<400> SEQUENCE: 55

Asn Thr Met Tyr Met Gln Asn Thr Val Ser Leu Glu Glu Glu Leu Arg
1               5                   10                  15

Lys

<210> SEQ ID NO 56
<211> LENGTH: 14
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION; tyrosine at position 5 is
      phosphorylated

<400> SEQUENCE: 56

Gln Asn Gln Glu Tyr Glu Ile Leu Leu Asp Val Lys Ser Arg
1               5                   10
```

```
<210> SEQ ID NO 57
<211> LENGTH: 13
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 57

Arg Pro Asp Leu Glu Ile Tyr Lys Pro Gly Leu Ser Arg
1               5                   10

<210> SEQ ID NO 58
<211> LENGTH: 12
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 58

Phe Gln Asn Ser Asp Asn Pro Tyr Tyr Tyr Pro Arg
1               5                   10

<210> SEQ ID NO 59
<211> LENGTH: 10
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at position 9 is
      phosphorylated

<400> SEQUENCE: 59

Lys Glu Ser Tyr Ser Val Tyr Val Tyr Lys
1               5                   10

<210> SEQ ID NO 60
<211> LENGTH: 10
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at position 9 is
      phosphorylated

<400> SEQUENCE: 60

Lys Glu Ser Tyr Ser Ile Tyr Val Tyr Lys
1               5                   10

<210> SEQ ID NO 61
<211> LENGTH: 22
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; tyrosine at position 3 is
      phosphorylated

<400> SEQUENCE: 61

Thr Glu Tyr Met Ala Phe Pro Lys Pro Phe Glu Ser Ser Ser Ser Ile
```

```
1               5                  10                 15

Gly Ala Glu Lys Pro Arg
            20

<210> SEQ ID NO 62
<211> LENGTH: 23
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; tyrosine at position 4 is
      phosphorylated

<400> SEQUENCE: 62

Gly Glu Pro Tyr Met Ser Ile Gln Pro Ala Glu Asp Pro Asp Asp Tyr
1               5                  10                 15

Asp Asp Gly Phe Ser Met Lys
            20

<210> SEQ ID NO 63
<211> LENGTH: 13
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION; tyrosine at position 11 is
      phosphorylated

<400> SEQUENCE: 63

Gly Tyr Phe Glu Tyr Ile Glu Glu Asn Lys Tyr Ser Arg
1               5                  10

<210> SEQ ID NO 64
<211> LENGTH: 14
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION; tyrosine at position 12 is
      phosphorylated

<400> SEQUENCE: 64

Ser Ile Lys His Glu Pro Glu Asn Pro Pro Pro Tyr Glu Glu
1               5                  10

<210> SEQ ID NO 65
<211> LENGTH: 16
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: PHOSPHORYLATION; tyrosine at position 14 is
      phosphorylated

<400> SEQUENCE: 65

Thr Lys Leu Ser Ala Glu Pro Ala Pro Asp Phe Ser Asp Tyr Ser Glu
1               5                  10                 15

<210> SEQ ID NO 66
<211> LENGTH: 22
<212> TYPE: PRT
<213> ORGANISM: Homo sapiens
<220> FEATURE:
<221> NAME/KEY: MOD_RES
```

```
<222> LOCATION: (3)..(3)
<223> OTHER INFORMATION: PHOSPHORYLATION; tyrosine at position 3 is
      phosphorylated

<400> SEQUENCE: 66

Leu Met Tyr Gly Met Leu Phe Ser Ile Arg Ser Phe Val Ser Lys Met
1               5                   10                  15

Ser Pro Leu Asp Met Lys
            20

<210> SEQ ID NO 67
<211> LENGTH: 16
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 67

Ser Asp Gly Gly Tyr Thr Tyr Asp Thr Ser Asp Leu Ala Ala Ile Lys
1               5                   10                  15

<210> SEQ ID NO 68
<211> LENGTH: 20
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION; tyrosine at position 2 is
      phosphorylated

<400> SEQUENCE: 68

Gly Tyr Phe Ile Gln Pro Thr Val Phe Gly Asp Val Gln Asp Gly Met
1               5                   10                  15

Thr Ile Ala Lys
            20

<210> SEQ ID NO 69
<211> LENGTH: 17
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; tyrosine at position 4 is
      phosphorylated

<400> SEQUENCE: 69

Asp Ser Asn Tyr His Leu Leu Met Ser Val Gln Glu Ser Leu Glu Arg
1               5                   10                  15

Lys

<210> SEQ ID NO 70
<211> LENGTH: 20
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: PHOSPHORYLATION; tyrosine at position 15 is
      phosphorylated

<400> SEQUENCE: 70

Asn Val Asn Ile Phe Lys Phe Ile Ile Pro Asn Val Val Lys Tyr Ser
```

```
                1               5                  10                  15

Pro Asn Cys Lys
            20

<210> SEQ ID NO 71
<211> LENGTH: 23
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: PHOSPHORYLATION; tyrosine at position 18 is
      phosphorylated

<400> SEQUENCE: 71

Gly Tyr Val Lys Asp Val Asp Asp Gly Leu Lys Ala Ala Glu Lys Val
1               5                  10                  15

Gly Tyr Pro Val Met Ile Lys
            20

<210> SEQ ID NO 72
<211> LENGTH: 19
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION; tyrosine at position 12 is
      phosphorylated

<400> SEQUENCE: 72

Thr Cys Phe Tyr Ala Glu Gln Gly Gly Gln Ile Tyr Asp Glu Gly Tyr
1               5                  10                  15

Leu Val Lys

<210> SEQ ID NO 73
<211> LENGTH: 12
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION; tyrosine at position 2 is
      phosphorylated

<400> SEQUENCE: 73

Pro Tyr Gln Tyr Pro Ala Leu Thr Pro Glu Gln Lys
1               5                  10

<210> SEQ ID NO 74
<211> LENGTH: 19
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: PHOSPHORYLATION; tyrosine at position 15 is
      phosphorylated

<400> SEQUENCE: 74

Leu Thr Val Leu Glu Lys Tyr Lys Gly Ile Ile Asp Ser Phe Tyr Gln
1               5                  10                  15

Glu Gln Lys

<210> SEQ ID NO 75
<211> LENGTH: 23
```

<212> TYPE: PRT
<213> ORGANISM: Homo sapiens
<220> FEATURE:
<221> NAME/KEY: MOD_RES
<222> LOCATION: (16)..(16)
<223> OTHER INFORMATION: PHOSPHORYLATION; tyrosine at position 16 is
      phosphorylated

<400> SEQUENCE: 75

Lys Val Ala Glu Pro Glu Leu Met Gly Thr Pro Asp Gly Thr Cys Tyr
1               5                   10                  15

Pro Pro Pro Pro Val Pro Arg
            20

<210> SEQ ID NO 76
<211> LENGTH: 30
<212> TYPE: PRT
<213> ORGANISM: Homo sapiens
<220> FEATURE:
<221> NAME/KEY: MOD_RES
<222> LOCATION: (24)..(24)
<223> OTHER INFORMATION: PHOSPHORYLATION; tyrosine at position 24 is
      phosphorylated

<400> SEQUENCE: 76

Leu Arg Ala Leu Val Gly Trp Ser Ser Gly Asp Gly Ile Phe Cys Pro
1               5                   10                  15

Gly Gly Ser Ile Ser Asn Met Tyr Ala Val Asn Leu Ala Arg
            20                  25                  30

<210> SEQ ID NO 77
<211> LENGTH: 29
<212> TYPE: PRT
<213> ORGANISM: Homo sapiens
<220> FEATURE:
<221> NAME/KEY: MOD_RES
<222> LOCATION: (25)..(25)
<223> OTHER INFORMATION: PHOSPHORYLATION; tyrosine at position 25 is
      phosphorylated

<400> SEQUENCE: 77

Cys Met Gln Leu Ile Leu Pro Glu Ala Val Gly Gly Thr Val Phe Ala
1               5                   10                  15

Gly Gly Leu Leu Gly Tyr Val Leu Tyr Asp Met Thr His
            20                  25

<210> SEQ ID NO 78
<211> LENGTH: 24
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: PHOSPHORYLATION; tyrosine at position 15 is
      phosphorylated

<400> SEQUENCE: 78

Ser Leu Tyr Gln Ser Ala Gly Val Ala Pro Glu Ser Phe Glu Tyr Ile
1               5                   10                  15

Glu Ala His Gly Thr Gly Thr Lys
            20

<210> SEQ ID NO 79
<211> LENGTH: 11
<212> TYPE: PRT
<213> ORGANISM: Homo sapiens
<220> FEATURE:

```
<221> NAME/KEY: MOD_RES
<222> LOCATION: (3)..(3)
<223> OTHER INFORMATION: PHOSPHORYLATION; tyrosine at position 3 is
      phosphorylated
<220> FEATURE:
<221> NAME/KEY: MOD_RES
<222> LOCATION: (3)..(3)

<400> SEQUENCE: 79

Ala Lys Tyr Ser Gly Asn Val Met Leu Leu Arg
1               5                   10

<210> SEQ ID NO 80
<211> LENGTH: 26
<212> TYPE: PRT
<213> ORGANISM: Homo sapiens
<220> FEATURE:
<221> NAME/KEY: MOD_RES
<222> LOCATION: (24)..(24)
<223> OTHER INFORMATION: PHOSPHORYLATION; tyrosine at position 24 is
      phosphorylated

<400> SEQUENCE: 80

Phe Lys Pro Gln Ser Leu Pro Asp His Lys Trp Glu Met Cys Thr Ser
1               5                   10                  15

Ile Asp Lys Phe Ser Trp Gly Tyr Arg Arg
            20                  25

<210> SEQ ID NO 81
<211> LENGTH: 30
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION; tyrosine at position 2 is
      phosphorylated

<400> SEQUENCE: 81

Ile Tyr Asn Leu Gly Thr Gly Thr Gly Tyr Ser Val Leu Gln Met Val
1               5                   10                  15

Gln Ala Met Glu Lys Ala Ser Gly Lys Lys Ile Pro Tyr Lys
            20                  25                  30

<210> SEQ ID NO 82
<211> LENGTH: 30
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION; tyrosine at position 10 is
      phosphorylated

<400> SEQUENCE: 82

Ile Tyr Asn Leu Gly Thr Gly Thr Gly Tyr Ser Val Leu Gln Met Val
1               5                   10                  15

Gln Ala Met Glu Lys Ala Ser Gly Lys Lys Ile Pro Tyr Lys
            20                  25                  30

<210> SEQ ID NO 83
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; tyrosine at position 4 is
```

-continued

```
      phosphorylated

<400> SEQUENCE: 83

Leu Gly Ile Tyr Ala Asp Val Gly Asn Lys
1               5                   10

<210> SEQ ID NO 84
<211> LENGTH: 34
<212> TYPE: PRT
<213> ORGANISM: Homo sapiens
<220> FEATURE:
<221> NAME/KEY: MOD_RES
<222> LOCATION: (21)..(21)
<223> OTHER INFORMATION: PHOSPHORYLATION; tyrosine at position 21 is
      phosphorylated

<400> SEQUENCE: 84

Ala Leu Leu Gln Asp Lys Asp Val Ile Ala Ile Asn Gln Asp Pro Leu
1               5                   10                  15

Gly Lys Gln Gly Tyr Gln Leu Arg Gln Gly Asp Asn Phe Glu Val Trp
            20                  25                  30

Glu Arg

<210> SEQ ID NO 85
<211> LENGTH: 23
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION; tyrosine at position 2 is
      phosphorylated

<400> SEQUENCE: 85

Asp Tyr Ile Met Ser Ala Gly Leu Val Thr Ser Glu Lys Glu Ser Ala
1               5                   10                  15

Ala His Ile Leu Asn Arg Lys
            20

<210> SEQ ID NO 86
<211> LENGTH: 10
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION; tyrosine at position is
      phosphorylated

<400> SEQUENCE: 86

Ile Tyr Gly Ile Ser Phe Pro Asp Pro Lys
1               5                   10

<210> SEQ ID NO 87
<211> LENGTH: 20
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION; tyrosine at position 12 is
      phosphorylated

<400> SEQUENCE: 87

Leu Val Ile Thr Asn Gly Met Val Ile Pro Asn Tyr Ser Ser Arg Thr
1               5                   10                  15
```

```
Glu Tyr Glu Lys
            20

<210> SEQ ID NO 88
<211> LENGTH: 16
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 88

Asp Pro Gly Val Ile Thr Tyr Asp Leu Pro Thr Pro Pro Gly Glu Lys
1               5                   10                  15

<210> SEQ ID NO 89
<211> LENGTH: 20
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: PHOSPHORYLATION; tyrosine at position 18 is
      phosphorylated

<400> SEQUENCE: 89

Asp Arg Thr Asp Ile Gln Cys Leu Ile Pro Cys Ala Ile Asp Gln Asp
1               5                   10                  15

Pro Tyr Phe Arg
            20

<210> SEQ ID NO 90
<211> LENGTH: 18
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION; tyrosine at position 12 is
      phosphorylated

<400> SEQUENCE: 90

His Ile Ile Ile Asn Ser Thr Thr Val Glu Leu Tyr Trp Ser Leu Pro
1               5                   10                  15

Glu Lys

<210> SEQ ID NO 91
<211> LENGTH: 28
<212> TYPE: PRT
<213> ORGANISM: Homo sapiens
<220> FEATURE:
<221> NAME/KEY: MOD_RES
<222> LOCATION: (21)..(21)
<223> OTHER INFORMATION: PHOSPHORYLATION; tyrosine at position 21 is
      phosphorylated

<400> SEQUENCE: 91

Glu Ala Lys Asn Leu Thr Ala Ala Lys Ala Gly Gly Thr Ser Asp Ser
1               5                   10                  15

Phe Val Lys Gly Tyr Leu Leu Pro Met Arg Asn Lys
            20                  25

<210> SEQ ID NO 92
<211> LENGTH: 22
<212> TYPE: PRT
```

```
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; tyrosine at position 3 is
      phosphorylated

<400> SEQUENCE: 92

His Leu Tyr His Gln Ala Phe Pro Thr Pro Lys Ser Glu Ser Thr Glu
1               5                   10                  15

Gln Ser Glu Lys Lys Lys
            20

<210> SEQ ID NO 93
<211> LENGTH: 13
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION; tyrosine at position 12 is
      phosphorylated

<400> SEQUENCE: 93

Ala Gln Ile Trp Asp Thr Ala Gly Gln Glu Arg Tyr Arg
1               5                   10

<210> SEQ ID NO 94
<211> LENGTH: 17
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION; tyrosine at position 11 is
      phosphorylated

<400> SEQUENCE: 94

Lys Lys Tyr Asn Asp Asp Ser Asp Asp Ser Tyr Phe Thr Ser Ser Ser
1               5                   10                  15

Arg

<210> SEQ ID NO 95
<211> LENGTH: 23
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: PHOSPHORYLATION; tyrosine at position 15 is
      phosphorylated

<400> SEQUENCE: 95

Leu Thr Ser Pro Ala Ala Ser Glu Lys Pro Asp Leu Ala Gly Tyr Glu
1               5                   10                  15

Ala Gln Gly Ala Arg Pro Lys
            20

<210> SEQ ID NO 96
<211> LENGTH: 26
<212> TYPE: PRT
<213> ORGANISM: Homo sapiens
<220> FEATURE:
<221> NAME/KEY: MOD_RES
<222> LOCATION: (20)..(20)
<223> OTHER INFORMATION: PHOSPHORYLATION; tyrosine at position 20 is
      phosphorylated
```

```
<400> SEQUENCE: 96

Asn Cys Gln Asn Lys Ser Leu Ser Gln Ser Phe Glu Asn Leu Leu Asp
1               5                   10                  15

Glu Pro Ala Tyr Gly Leu Ile Gln Ala Gly
            20                  25

<210> SEQ ID NO 97
<211> LENGTH: 20
<212> TYPE: PRT
<213> ORGANISM: Homo sapiens
<220> FEATURE:
<221> NAME/KEY: MOD_RES
<222> LOCATION: (19)..(19)
<223> OTHER INFORMATION: PHOSPHORYLATION; tyrosine at position 19 is
      phosphorylated

<400> SEQUENCE: 97

Glu Lys Phe Lys Gly Trp Val Ser Tyr Ser Thr Ser Glu Gln Ala Glu
1               5                   10                  15

Leu Ser Tyr Lys
            20

<210> SEQ ID NO 98
<211> LENGTH: 16
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; tyrosine at position 3 is
      phosphorylated

<400> SEQUENCE: 98

Ser Asp Tyr His Val Thr Gln Leu Gln Pro Tyr Phe Glu Asn Gly Arg
1               5                   10                  15

<210> SEQ ID NO 99
<211> LENGTH: 13
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; tyrosine at position 3 is
      phosphorylated

<400> SEQUENCE: 99

Ser Leu Tyr Ser Tyr Ala Gly Leu Ala Pro Arg Pro Arg
1               5                   10

<210> SEQ ID NO 100
<211> LENGTH: 24
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated

<400> SEQUENCE: 100

Ala Asn Val Thr Gly Tyr Phe Ser Pro Asn Asp His Asn Val Val Ser
1               5                   10                  15

Met Pro Pro Ala Ala Asp Val Lys
            20
```

```
<210> SEQ ID NO 101
<211> LENGTH: 23
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; tyrosine at position 3 is
      phosphorylated

<400> SEQUENCE: 101

Met Ser Tyr Tyr Cys Ser Gly Ser Ser Asp Ala Pro Ser Ser Pro Ala
1               5                   10                  15

Ala Pro Arg Pro Ala Ser Lys
            20

<210> SEQ ID NO 102
<211> LENGTH: 20
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION; tyrosine at position 12 is
      phosphorylated

<400> SEQUENCE: 102

Val Ser Met Leu Pro Ser Gly Val Gly Pro Glu Tyr Ala Glu Arg Pro
1               5                   10                  15

Glu Val Ala Arg
            20

<210> SEQ ID NO 103
<211> LENGTH: 11
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PHOSPHORYLATION; tyrosine at position 1 is
      phosphorylated

<400> SEQUENCE: 103

Tyr Leu Lys Gly Pro Ser Gln Arg Leu Ile Lys
1               5                   10

<210> SEQ ID NO 104
<211> LENGTH: 14
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: PHOSPHORYLATION; tyrosine at position 13 is
      phosphorylated

<400> SEQUENCE: 104

His Ser Ser Leu Ile Asp Ile Asp Ser Val Pro Thr Tyr Lys
1               5                   10

<210> SEQ ID NO 105
<211> LENGTH: 19
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION; tyrosine at position 12 is
      phosphorylated
```

```
<400> SEQUENCE: 105

Thr Thr Ser Ser Ala Asn Asn Pro Asn Leu Met Tyr Gln Asp Glu Cys
1               5                   10                  15

Asp Arg Arg

<210> SEQ ID NO 106
<211> LENGTH: 13
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION; tyrosine at position 12 is
      phosphorylated

<400> SEQUENCE: 106

Met Leu Ala Asn Phe Glu Ser Gly Lys His Lys Tyr Arg
1               5                   10

<210> SEQ ID NO 107
<211> LENGTH: 18
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PHOSPHORYLATION; tyrosine at position 1 is
      phosphorylated

<400> SEQUENCE: 107

Tyr Ile Asp Cys Asp Leu Asn Arg Ile Phe Asp Leu Glu Asn Leu Gly
1               5                   10                  15

Lys Lys

<210> SEQ ID NO 108
<211> LENGTH: 19
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION; tyrosine at position 2 is
      phosphorylataed

<400> SEQUENCE: 108

Phe Tyr Glu Gly Thr Ala Asp Glu Met Cys Lys Ala Leu Leu Glu Val
1               5                   10                  15

Leu Gly Arg

<210> SEQ ID NO 109
<211> LENGTH: 24
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: PHOSPHORYLATION; tyrosine at position 14 is
      phosphorylated

<400> SEQUENCE: 109

Met Val Val Asn Glu Gly Ser Asp Gly Gly Gln Ser Val Tyr His Val
1               5                   10                  15

His Leu His Val Leu Gly Gly Arg
            20
```

```
<210> SEQ ID NO 110
<211> LENGTH: 12
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION; tyrosine at position 11 is
      phosphorylated

<400> SEQUENCE: 110

Cys Leu Gly Pro Pro Thr Thr Pro Gly Pro Tyr Arg
1               5                  10

<210> SEQ ID NO 111
<211> LENGTH: 21
<212> TYPE: PRT
<213> ORGANISM: Homo sapiens
<220> FEATURE:
<221> NAME/KEY: MOD_RES
<222> LOCATION: (19)..(19)
<223> OTHER INFORMATION: PHOSPHORYLATION; tyrosine at position 19 is
      phosphorylated

<400> SEQUENCE: 111

Thr Ser Gln Leu Leu Ala Glu Leu Asn Phe Glu Glu Asp Glu Glu Asp
1               5                  10                  15

Thr Tyr Tyr Thr Lys
            20

<210> SEQ ID NO 112
<211> LENGTH: 17
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 112

Met Ile Gly Gln Lys Thr Leu Tyr Ser Phe Phe Ser Pro Ser Pro Ala
1               5                  10                  15

Arg

<210> SEQ ID NO 113
<211> LENGTH: 19
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at position 9 is
      phosphorylated

<400> SEQUENCE: 113

Glu Ala Ile Gly Ala Val Ile His Tyr Leu Leu Gln Val Gly Ser Glu
1               5                  10                  15

Lys Gln Lys

<210> SEQ ID NO 114
<211> LENGTH: 30
<212> TYPE: PRT
<213> ORGANISM: Homo sapiens
<220> FEATURE:
<221> NAME/KEY: MOD_RES
<222> LOCATION: (3)..(3)
```

```
<223> OTHER INFORMATION: PHOSPHORYLATION; tyrosine at position 3 is
      phosphorylated

<400> SEQUENCE: 114

Arg Val Tyr Met Gln Ser Gln Ala Asn Gln Ile Thr Phe Gly Gln Pro
1               5                   10                  15
Gly Leu Asp Ile Gln Ser Arg Ser Met Glu Tyr Val Gln Arg
            20                  25                  30

<210> SEQ ID NO 115
<211> LENGTH: 16
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PHOSPHORYLATION; tyrosine at position 1 is
      phosphorylated

<400> SEQUENCE: 115

Tyr Trp Leu Gly Gly Pro Asp Pro Leu Asp Tyr Val Ser Met Tyr Arg
1               5                   10                  15

<210> SEQ ID NO 116
<211> LENGTH: 11
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; tyrosine at position 3 is
      phosphorylated

<400> SEQUENCE: 116

Phe Gly Tyr His Ile Ile Met Val Glu Gly Arg
1               5                   10

<210> SEQ ID NO 117
<211> LENGTH: 28
<212> TYPE: PRT
<213> ORGANISM: Homo sapiens
<220> FEATURE:
<221> NAME/KEY: MOD_RES
<222> LOCATION: (19)..(19)
<223> OTHER INFORMATION: PHOSPHORYLATION; tyrosine at position 19 is
      phosphorylated

<400> SEQUENCE: 117

Tyr Leu Pro Lys Tyr Tyr Gly Ile Trp Ser Pro Pro Thr Ala Pro Asn
1               5                   10                  15
Asp Leu Tyr Leu Lys Leu Glu Asp Val Thr His Lys
            20                  25

<210> SEQ ID NO 118
<211> LENGTH: 13
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION; tyrosine at position 12 is
      phosphorylated

<400> SEQUENCE: 118

Pro Thr Gln Ser Val Gln Ser Gln Ala Leu His Tyr Arg
1               5                   10
```

```
<210> SEQ ID NO 119
<211> LENGTH: 25
<212> TYPE: PRT
<213> ORGANISM: Homo sapiens
<220> FEATURE:
<221> NAME/KEY: MOD_RES
<222> LOCATION: (23)..(23)
<223> OTHER INFORMATION: PHOSPHORYLATION; tyrosine at position 23 is
      phosphorylated

<400> SEQUENCE: 119

Glu Pro Pro Lys Ile Ser Asn Lys Val Asp Val Trp Ser Val Gly Val
1               5                   10                  15

Ile Phe Phe Gln Cys Leu Tyr Gly Arg
            20                  25

<210> SEQ ID NO 120
<211> LENGTH: 20
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; tyrosine at position 4 is
      phosphorylated

<400> SEQUENCE: 120

Ile Ala Lys Tyr Ala Val Pro Asp Glu Ile Leu Val Val Lys Arg Leu
1               5                   10                  15

Pro Lys Thr Arg
            20

<210> SEQ ID NO 121
<211> LENGTH: 21
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION; tyrosine at position 2 is
      phosphorylated

<400> SEQUENCE: 121

Val Tyr Met Asp Tyr Asn Ala Thr Thr Pro Leu Glu Pro Glu Val Ile
1               5                   10                  15

Gln Ala Met Thr Lys
            20

<210> SEQ ID NO 122
<211> LENGTH: 21
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION; tyrosine at position 5 is
      phosphorylated

<400> SEQUENCE: 122

Val Tyr Met Asp Tyr Asn Ala Thr Thr Pro Leu Glu Pro Glu Val Ile
1               5                   10                  15

Gln Ala Met Thr Lys
            20

<210> SEQ ID NO 123
<211> LENGTH: 30
<212> TYPE: PRT
```

```
<213> ORGANISM: Homo sapiens
<220> FEATURE:
<221> NAME/KEY: MOD_RES
<222> LOCATION: (5)..(5)
<223> OTHER INFORMATION: PHOSPHORYLATION; tyrosine at position 5 is
      phosphorylated

<400> SEQUENCE: 123

Thr Pro Gly Asn Tyr Glu Ser Lys Arg Gln Arg Lys Pro Thr Lys Lys
1               5                   10                  15

Leu Leu Glu Ser Asn Asp Leu Asp Pro Gly Phe Met Pro Lys
            20                  25                  30

<210> SEQ ID NO 124
<211> LENGTH: 20
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; tyrosine at position 4 is
      phosphorylated

<400> SEQUENCE: 124

Met Pro Val Tyr Cys Gly Asn Glu Val Thr Pro Thr Glu Ala Ala Gln
1               5                   10                  15

Ala Pro Glu Val
            20

<210> SEQ ID NO 125
<211> LENGTH: 13
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION; tyrosine at position 5 is
      phosphorylated

<400> SEQUENCE: 125

Met Arg Ser Gly Tyr Gly Ala Thr Ala Leu Asn Met Lys
1               5                   10

<210> SEQ ID NO 126
<211> LENGTH: 20
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: PHOSPHORYLATION; tyrosine at position 18 is
      phosphorylated

<400> SEQUENCE: 126

Val Gln Val Ala Val Asn Ile Leu Lys Thr Phe Lys Asn Ser Phe Phe
1               5                   10                  15

Asn Tyr Arg Lys
            20

<210> SEQ ID NO 127
<211> LENGTH: 16
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PHOSPHORYLATION; tyrosine at position 1 is
      phosphorylated
```

<400> SEQUENCE: 127

Tyr Ile Gly Asn Leu Asp Leu Leu Val Gln Gly Tyr Asn Lys Leu Lys
1               5                   10                  15

<210> SEQ ID NO 128
<211> LENGTH: 19
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION; tyrosine at position 11 is
      phosphorylated

<400> SEQUENCE: 128

Phe Arg Thr Val Ala Met Met Val Pro Asp Tyr Ala Leu Ile Gly Glu
1               5                   10                  15

Ile Ser Leu

<210> SEQ ID NO 129
<211> LENGTH: 31
<212> TYPE: PRT
<213> ORGANISM: Homo sapiens
<220> FEATURE:
<221> NAME/KEY: MOD_RES
<222> LOCATION: (30)..(30)
<223> OTHER INFORMATION: PHOSPHORYLATION; tyrosine at position 30 is
      phosphorylated

<400> SEQUENCE: 129

Asp Ile Ser Lys Leu Val Leu Leu Ser Ser Ser Val Asn Ser Leu
1               5                   10                  15

Arg Lys Ala Ala His Glu Ala Leu Gln Asp Phe Gln Lys Tyr Lys
            20                  25                  30

<210> SEQ ID NO 130
<211> LENGTH: 27
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION; tyrosine at position 11 is
      phosphorylated

<400> SEQUENCE: 130

Arg Arg Arg Arg Ser Arg Ala Ser Ile Ser Tyr Gly Ser Asn Met Arg
1               5                   10                  15

Pro Gln Ser Gln Thr Trp Arg Asp Arg Leu Arg
            20                  25

<210> SEQ ID NO 131
<211> LENGTH: 17
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; tyrosine at position 4 is
      phosphorylated

<400> SEQUENCE: 131

Tyr Gly Cys Tyr Lys Leu Thr Gly Ala Ile Met His Phe Gly Asn Met
1               5                   10                  15

Lys

<210> SEQ ID NO 132
<211> LENGTH: 11
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; tyrosine at position 3 is
      phosphorylated

<400> SEQUENCE: 132

Leu Leu Tyr Asn Ser Thr Asp Pro Thr Leu Arg
1               5                   10

<210> SEQ ID NO 133
<211> LENGTH: 14
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION; tyrosine at position 12 is
      phosphorylated

<400> SEQUENCE: 133

Lys Thr Met Glu Trp Phe Thr Val Leu Glu His Tyr Arg Arg
1               5                   10

<210> SEQ ID NO 134
<211> LENGTH: 28
<212> TYPE: PRT
<213> ORGANISM: Homo sapiens
<220> FEATURE:
<221> NAME/KEY: MOD_RES
<222> LOCATION: (27)..(27)
<223> OTHER INFORMATION: PHOSPHORYLATION; tyrosine at position 27 is
      phosphorylated

<400> SEQUENCE: 134

Gln Asn Lys Thr Thr Leu Thr Tyr Val Ala Ala Val Ala Val Gly Met
1               5                   10                  15

Leu Gly Ala Ser Tyr Ala Ala Val Pro Leu Tyr Arg
            20                  25

<210> SEQ ID NO 135
<211> LENGTH: 18
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION; tyrosine at position 11 is
      phosphorylated

<400> SEQUENCE: 135

Met Lys Cys Lys Pro Asn Gln Thr Arg Thr Tyr Asp Pro Glu Gly Phe
1               5                   10                  15

Lys Lys

<210> SEQ ID NO 136
<211> LENGTH: 30
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; tyrosine at position 3 is phosphorylated

<400> SEQUENCE: 136

Phe Ile Tyr Glu Phe Glu His Phe Asn Gly Val Ala Glu Leu Leu Glu
1               5                   10                  15

Ile Leu Gly Ser Ile Ile Asn Gly Phe Ala Leu Pro Leu Lys
            20                  25                  30

<210> SEQ ID NO 137
<211> LENGTH: 32
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION; tyrosine at position 10 is
      phosphorylated

<400> SEQUENCE: 137

His His Asp Ser Ser Ala Leu Gly Val Tyr Ser Tyr Ile Pro Leu Val
1               5                   10                  15

Glu Asn Pro Tyr Phe Ser Ser Trp Pro Pro Ser Gly Thr Ser Ser Lys
            20                  25                  30

<210> SEQ ID NO 138
<211> LENGTH: 32
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION; tyrosine at position 12 is
      phosphorylated

<400> SEQUENCE: 138

His His Asp Ser Ser Ala Leu Gly Val Tyr Ser Tyr Ile Pro Leu Val
1               5                   10                  15

Glu Asn Pro Tyr Phe Ser Ser Trp Pro Pro Ser Gly Thr Ser Ser Lys
            20                  25                  30

<210> SEQ ID NO 139
<211> LENGTH: 32
<212> TYPE: PRT
<213> ORGANISM: Homo sapiens
<220> FEATURE:
<221> NAME/KEY: MOD_RES
<222> LOCATION: (20)..(20)
<223> OTHER INFORMATION: PHOSPHORYLATION; tyrosine at position 20 is
      phosphorylated

<400> SEQUENCE: 139

His His Asp Ser Ser Ala Leu Gly Val Tyr Ser Tyr Ile Pro Leu Val
1               5                   10                  15

Glu Asn Pro Tyr Phe Ser Ser Trp Pro Pro Ser Gly Thr Ser Ser Lys
            20                  25                  30

<210> SEQ ID NO 140
<211> LENGTH: 10
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION; tyrosine at position 5 is
      phosphorylated

<400> SEQUENCE: 140

```
Asp Ser Gly Gly Tyr Tyr His Pro Ala Arg
1               5                   10

<210> SEQ ID NO 141
<211> LENGTH: 13
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at position 9 is
      phosphorylated

<400> SEQUENCE: 141

Ser Gln Asp Asp Ala Met Val Asp Tyr Phe Phe Gln Arg
1               5                   10

<210> SEQ ID NO 142
<211> LENGTH: 15
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; tyrosine at position 4 is
      phosphorylated

<400> SEQUENCE: 142

Leu Ser Asp Tyr Gly Val Thr Val Pro Cys Ser Thr Asp Phe Arg
1               5                   10                  15

<210> SEQ ID NO 143
<211> LENGTH: 22
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: PHOSPHORYLATION; tyrosine at position 17 is
      phosphorylated

<400> SEQUENCE: 143

Leu Lys Glu Ser Gly His Gly Asn Ser Val Cys Pro Val Thr Ser Asn
1               5                   10                  15

Tyr His Ser Ser Gln Arg
            20

<210> SEQ ID NO 144
<211> LENGTH: 12
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION; tyrosine at position 5 is
      phosphorylated

<400> SEQUENCE: 144

Asn Ala Thr Arg Tyr Val Val Leu His Ala Ser Arg
1               5                   10

<210> SEQ ID NO 145
<211> LENGTH: 21
<212> TYPE: PRT
<213> ORGANISM: Homo sapiens
<220> FEATURE:
<221> NAME/KEY: MOD_RES
<222> LOCATION: (3)..(3)
```

-continued

<223> OTHER INFORMATION: PHOSPHORYLATION; tyrosine at position 3 is
      phosphorylated

<400> SEQUENCE: 145

Ile Thr Tyr Leu Asp Lys Gly Ser Trp Leu Leu Gly Asn Ile Asn Gln
1               5                   10                  15

Thr Gly Tyr Phe Arg
            20

<210> SEQ ID NO 146
<211> LENGTH: 16
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; tyrosine at position 4 is
      phosphorylated

<400> SEQUENCE: 146

Thr Ser His Tyr Leu Thr Pro Gln Ser Asn His Leu Ser Leu Ser Lys
1               5                   10                  15

<210> SEQ ID NO 147
<211> LENGTH: 29
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: PHOSPHORYLATION; tyrosine at position 14 is
      phosphorylated

<400> SEQUENCE: 147

Ala Ala Leu Met Phe Ala Asn Ala Glu Glu Phe Phe Tyr Glu Glu
1               5                   10                  15

Gln Gly Lys Pro Glu Val Leu Gly Gly Pro Asp Thr Arg
            20                  25

<210> SEQ ID NO 148
<211> LENGTH: 20
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PHOSPHORYLATION; tyrosine at position 1 is
      phosphorylated

<400> SEQUENCE: 148

Tyr Tyr Asn Lys Pro Leu Leu Gly Gln Thr Gly Leu Pro Gln Gly Pro
1               5                   10                  15

Ser Glu Gln Lys
            20

<210> SEQ ID NO 149
<211> LENGTH: 20
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION; tyrosine at position 2 is
      phosphorylated

<400> SEQUENCE: 149

Tyr Tyr Asn Lys Pro Leu Leu Gly Gln Thr Gly Leu Pro Gln Gly Pro

```
                1               5                  10                 15

Ser Glu Gln Lys
            20

<210> SEQ ID NO 150
<211> LENGTH: 34
<212> TYPE: PRT
<213> ORGANISM: Homo sapiens
<220> FEATURE:
<221> NAME/KEY: MOD_RES
<222> LOCATION: (28)..(28)
<223> OTHER INFORMATION: PHOSPHORYLATION; tyrosine at position 28 is
      phosphorylated

<400> SEQUENCE: 150

Pro Ala Leu Leu Ala Ala Gly Val Ala Ile Gln Val Gly Ser Leu Leu
1               5                  10                 15

Gly Ala Val Ala Met Phe Pro Pro Thr Ser Ile Tyr His Val Phe His
            20                  25                 30

Ser Arg

<210> SEQ ID NO 151
<211> LENGTH: 27
<212> TYPE: PRT
<213> ORGANISM: Homo sapiens
<220> FEATURE:
<221> NAME/KEY: MOD_RES
<222> LOCATION: (23)..(23)
<223> OTHER INFORMATION: PHOSPHORYLATION; tyrosine at position 23 is
      phosphorylated

<400> SEQUENCE: 151

Ala Phe Ser Thr Cys Ala Ala His Leu Thr Ser Val Thr Leu Phe Tyr
1               5                  10                 15

Gly Thr Ala Ser Met Thr Tyr Leu Gln Pro Lys
            20                  25

<210> SEQ ID NO 152
<211> LENGTH: 27
<212> TYPE: PRT
<213> ORGANISM: Homo sapiens
<220> FEATURE:
<221> NAME/KEY: MOD_RES
<222> LOCATION: (23)..(23)
<223> OTHER INFORMATION: PHOSPHORYLATION; tyrosine at position 23 is
      phosphorylated

<400> SEQUENCE: 152

Ala Phe Cys Thr Cys Phe Ser His Leu Cys Val Ile Gly Leu Phe Tyr
1               5                  10                 15

Gly Thr Ala Ile Ile Met Tyr Val Gly Pro Arg
            20                  25

<210> SEQ ID NO 153
<211> LENGTH: 23
<212> TYPE: PRT
<213> ORGANISM: Homo sapiens
<220> FEATURE:
<221> NAME/KEY: MOD_RES
<222> LOCATION: (20)..(20)
<223> OTHER INFORMATION: PHOSPHORYLATION; tyrosine at position 20 is
      phosphorylated

<400> SEQUENCE: 153

Gly Lys Met Val Ser Leu Phe Cys Gly Ile Ile Ala Pro Met Leu Asn
1               5                  10                 15
```

```
Pro Leu Ile Tyr Thr Leu Arg
            20

<210> SEQ ID NO 154
<211> LENGTH: 32
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION tyrosine at position 12 is
      phosphorylated

<400> SEQUENCE: 154

Thr Ile Thr Tyr Gly Gly Cys Val Ala Gln Leu Tyr Ile Ser Leu Ala
1               5                   10                  15

Leu Gly Ser Thr Glu Cys Ile Leu Leu Ala Asp Met Ala Leu Asp Arg
            20                  25                  30

<210> SEQ ID NO 155
<211> LENGTH: 21
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: PHOSPHORYLATION; tyrosine at position 18 is
      phosphorylated

<400> SEQUENCE: 155

Ala Val Ser Ala Phe Tyr Thr Ile Leu Thr Pro Met Leu Asn Pro Leu
1               5                   10                  15

Ile Tyr Ser Leu Arg
            20

<210> SEQ ID NO 156
<211> LENGTH: 32
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 156

Asp Met Met Val Ser Val Phe Tyr Thr Ile Leu Thr Pro Val Leu Asn
1               5                   10                  15

Pro Leu Ile Tyr Ser Leu Arg Asn Lys Asp Val Met Gly Ala Leu Lys
            20                  25                  30

<210> SEQ ID NO 157
<211> LENGTH: 32
<212> TYPE: PRT
<213> ORGANISM: Homo sapiens
<220> FEATURE:
<221> NAME/KEY: MOD_RES
<222> LOCATION: (20)..(20)
<223> OTHER INFORMATION: PHOSPHORYLATION; tyrosine at position 20 is
      phosphorylated

<400> SEQUENCE: 157

Asp Met Met Val Ser Val Phe Tyr Thr Ile Leu Thr Pro Val Leu Asn
1               5                   10                  15

Pro Leu Ile Tyr Ser Leu Arg Asn Lys Asp Val Met Gly Ala Leu Lys
            20                  25                  30
```

```
<210> SEQ ID NO 158
<211> LENGTH: 30
<212> TYPE: PRT
<213> ORGANISM: Homo sapiens
<220> FEATURE:
<221> NAME/KEY: MOD_RES
<222> LOCATION: (27)..(27)
<223> OTHER INFORMATION: PHOSPHORYLATION; tyrosine at position 27 is
      phosphorylated

<400> SEQUENCE: 158

Ser Ser Tyr Ser Thr Asp Gln Asn Lys Val Val Ser Val Phe Tyr Thr
1               5                   10                  15

Val Val Ile Pro Met Leu Asn Pro Leu Ile Tyr Ser Leu Arg
            20                  25                  30

<210> SEQ ID NO 159
<211> LENGTH: 9
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 159

Met Pro Ser Ala Arg Gly Lys Tyr Lys
1               5

<210> SEQ ID NO 160
<211> LENGTH: 21
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PHOSPHORYLATION; tyrosine at position 1 is
      phosphorylated

<400> SEQUENCE: 160

Tyr Leu Val Thr Leu Met Gly Asn Thr Val Ile Ile Met Ile Val Cys
1               5                   10                  15

Val Asp Lys Arg Leu
            20

<210> SEQ ID NO 161
<211> LENGTH: 17
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PHOSPHORYLATION; tyrosine at position 1 is
      phosphorylated

<400> SEQUENCE: 161

Tyr Val Ser Tyr Ile Ser Pro Leu Ser Ala Val Ser Val Met Glu Asp
1               5                   10                  15

Lys

<210> SEQ ID NO 162
<211> LENGTH: 17
<212> TYPE: PRT
<213> ORGANISM: Homo sapiens
<220> FEATURE:
```

```
<221> NAME/KEY: MOD_RES
<222> LOCATION: (4)..(4)
<223> OTHER INFORMATION: PHOSPHORYLATION; tyrosine at position 4 is
      phosphorylated

<400> SEQUENCE: 162

Tyr Val Ser Tyr Ile Ser Pro Leu Ser Ala Val Ser Val Met Glu Asp
1               5                   10                  15

Lys

<210> SEQ ID NO 163
<211> LENGTH: 15
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: PHOSPHORYLATION; tyrosine at position 13 is
      phosphorylated

<400> SEQUENCE: 163

Gln Ser Pro His Asp Glu Asp Pro Gln Ala Val Thr Tyr Ala Lys
1               5                   10                  15

<210> SEQ ID NO 164
<211> LENGTH: 27
<212> TYPE: PRT
<213> ORGANISM: Homo sapiens
<220> FEATURE:
<221> NAME/KEY: MOD_RES
<222> LOCATION: (21)..(21)
<223> OTHER INFORMATION: PHOSPHORYLATION; tyrosine at position 21 is
      phosphorylated

<400> SEQUENCE: 164

Gln Lys Ala Thr Glu Pro Pro Pro Ser Gln Glu Gly Ala Ser Pro Ala
1               5                   10                  15

Glu Pro Ser Val Tyr Ala Thr Leu Ala Ile His
            20                  25

<210> SEQ ID NO 165
<211> LENGTH: 23
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: PHOSPHORYLATION; tyrosine at position 18 is
      phosphorylated

<400> SEQUENCE: 165

Cys Leu Pro Glu Ile Gln Gly Ile Phe Asp Arg Asp Pro Asp Thr Leu
1               5                   10                  15

Leu Tyr Leu Leu Gln Gln Lys
            20

<210> SEQ ID NO 166
<211> LENGTH: 19
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at position 9 is
      phosphorylated

<400> SEQUENCE: 166
```

```
Val Thr Ala Gly Asp Met Gly Ser Tyr Thr Cys Val Ala Glu Asn Met
1               5                   10                  15

Val Gly Lys

<210> SEQ ID NO 167
<211> LENGTH: 11
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 167

Asn Gly Leu Thr Ser Thr Tyr Ala Gly Ile Arg
1               5                   10

<210> SEQ ID NO 168
<211> LENGTH: 18
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 168

Asp Lys Glu Ala Ile Gln Ala Tyr Ser Glu Ser Leu Met Thr Ser Ala
1               5                   10                  15

Pro Lys

<210> SEQ ID NO 169
<211> LENGTH: 21
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: PHOSPHORYLATION; tyrosine at position 17 is
      phosphorylated

<400> SEQUENCE: 169

Met Val Asn Leu Gln Val Glu Asp Ser Gly Leu Tyr Gln Cys Val Ile
1               5                   10                  15

Tyr Gln Pro Pro Lys
                20

<210> SEQ ID NO 170
<211> LENGTH: 17
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; tyrosine at position 3 is
      phosphorylated

<400> SEQUENCE: 170

Ala Arg Tyr Pro His Leu Gly Gln Lys Pro Gly Gly Ser Asp Phe Leu
1               5                   10                  15

Arg

<210> SEQ ID NO 171
<211> LENGTH: 16
```

```
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: PHOSPHORYLATION; tyrosine at position 13 is
      phosphorylated

<400> SEQUENCE: 171

His Leu Asp Asp Asp Glu Asp Arg Lys Asn Pro Ala Tyr Ile Pro Arg
1               5                   10                  15

<210> SEQ ID NO 172
<211> LENGTH: 13
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION; tyrosine at position 10 is
      phosphorylated

<400> SEQUENCE: 172

Gly Ala Ala Pro Asn Val Val Tyr Thr Tyr Thr Gly Lys
1               5                   10

<210> SEQ ID NO 173
<211> LENGTH: 24
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: PHOSPHORYLATION; tyrosine at position 14 is
      phosphorylated

<400> SEQUENCE: 173

Gly Pro Pro Pro Thr Asp Pro Tyr Gly Arg Pro Pro Pro Tyr Asp Arg
1               5                   10                  15

Gly Asp Tyr Gly Pro Pro Gly Arg
            20

<210> SEQ ID NO 174
<211> LENGTH: 24
<212> TYPE: PRT
<213> ORGANISM: Homo sapiens
<220> FEATURE:
<221> NAME/KEY: MOD_RES
<222> LOCATION: (19)..(19)
<223> OTHER INFORMATION: PHOSPHORYLATION; tyrosine at position 19 is
      phosphorylated

<400> SEQUENCE: 174

Gly Pro Pro Pro Thr Asp Pro Tyr Gly Arg Pro Pro Pro Tyr Asp Arg
1               5                   10                  15

Gly Asp Tyr Gly Pro Pro Gly Arg
            20

<210> SEQ ID NO 175
<211> LENGTH: 14
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at position 9 is
      phosphorylated

<400> SEQUENCE: 175
```

```
Asn Val Ala Leu Leu Ser Gln Leu Tyr His Ser Pro Ala Arg
1               5                   10

<210> SEQ ID NO 176
<211> LENGTH: 22
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: PHOSPHORYLATION; tyrosine at position 18 is
      phosphorylated

<400> SEQUENCE: 176

Glu Trp Gly Glu Glu Leu Gln Ala Val Leu Arg Ser Ser Gln Gly Thr
1               5                   10                  15

Ser Tyr Asp Ser Tyr Arg
            20

<210> SEQ ID NO 177
<211> LENGTH: 33
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: PHOSPHORYLATION; tyrosine at position 18 is
      phosphorylated

<400> SEQUENCE: 177

Ser Gln Glu Ser Lys Thr Thr Tyr Leu Glu Asp Leu Pro Pro Pro Pro
1               5                   10                  15

Glu Tyr Glu Leu Ala Pro Ser Lys Leu Glu Glu Glu Val Asp Asp Val
            20                  25                  30

Phe

<210> SEQ ID NO 178
<211> LENGTH: 20
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated

<400> SEQUENCE: 178

Gly Phe Gly Phe Val Tyr Phe Gln Asn His Asp Ala Ala Asp Lys Ala
1               5                   10                  15

Ala Val Val Lys
            20

<210> SEQ ID NO 179
<211> LENGTH: 12
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PHOSPHORYLATION; tyrosine at position 1 is
      phosphorylated

<400> SEQUENCE: 179

Tyr His Thr Val Asn Gly His Asn Cys Glu Val Arg
1               5                   10
```

```
<210> SEQ ID NO 180
<211> LENGTH: 12
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PHOSPHORYLATION; tyrosine at position 1 is
      phosphorylated

<400> SEQUENCE: 180

Tyr His Thr Ile Asn Gly His Asn Ala Glu Val Arg
1               5                   10

<210> SEQ ID NO 181
<211> LENGTH: 12
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 181

Asp Tyr Tyr Asp Arg Met Tyr Ser Tyr Pro Ala Arg
1               5                   10

<210> SEQ ID NO 182
<211> LENGTH: 26
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 182

Gly Ala Tyr Gly Gly Gly Tyr Gly Gly Tyr Asp Asp Tyr Gly Gly Tyr
1               5                   10                  15

Asn Asp Gly Tyr Gly Phe Gly Ser Asp Arg
            20                  25

<210> SEQ ID NO 183
<211> LENGTH: 26
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: PHOSPHORYLATION; tyrosine at position 16 is
      phosphorylated

<400> SEQUENCE: 183

Gly Ala Tyr Gly Gly Gly Tyr Gly Gly Tyr Asp Asp Tyr Gly Gly Tyr
1               5                   10                  15

Asn Asp Gly Tyr Gly Phe Gly Ser Asp Arg
            20                  25

<210> SEQ ID NO 184
<211> LENGTH: 19
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; tyrosine at position 3 is
```

-continued phosphorylated

<400> SEQUENCE: 184

Gly Ser Tyr Gly Asp Leu Gly Gly Pro Ile Ile Thr Thr Gln Val Thr
1               5                   10                  15

Ile Pro Lys

<210> SEQ ID NO 185
<211> LENGTH: 20
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: PHOSPHORYLATION; tyrosine at position 18 is
      phosphorylated

<400> SEQUENCE: 185

Gln Asn Gln Phe Tyr Asp Thr Gln Val Ile Lys Gln Glu Asn Glu Ser
1               5                   10                  15

Gly Tyr Glu Arg
            20

<210> SEQ ID NO 186
<211> LENGTH: 21
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at position 9 is
      phosphorylated

<400> SEQUENCE: 186

Ser Gln Ser Gln Gly Asp Ser Glu Tyr Tyr Asp Tyr Gly His Gly Glu
1               5                   10                  15

Val Gln Asp Ser Tyr
            20

<210> SEQ ID NO 187
<211> LENGTH: 19
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: PHOSPHORYLATION; tyrosine at position 13 is
      phosphorylated

<400> SEQUENCE: 187

Gly Tyr Tyr Ser Gln Ser Gln Gly Asp Ser Glu Tyr Tyr Asp Tyr Gly
1               5                   10                  15

His Gly Glu

<210> SEQ ID NO 188
<211> LENGTH: 11
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; tyrosine at position 3 is
      phosphorylated

<400> SEQUENCE: 188

Gly Ala Tyr Arg Glu His Pro Tyr Gly Arg Tyr

```
<210> SEQ ID NO 189
<211> LENGTH: 12
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 189

Ser Ala Thr Arg Glu Pro Pro Tyr Arg Val Pro Arg
1               5                   10

<210> SEQ ID NO 190
<211> LENGTH: 23
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: PHOSPHORYLATION; tyrosine at position 14 is
      phosphorylated

<400> SEQUENCE: 190

Cys Arg Asp Asp Ser Phe Phe Gly Glu Thr Ser His Asn Tyr His Lys
1               5                   10                  15

Phe Asp Ser Glu Tyr Glu Arg
            20

<210> SEQ ID NO 191
<211> LENGTH: 23
<212> TYPE: PRT
<213> ORGANISM: Homo sapiens
<220> FEATURE:
<221> NAME/KEY: MOD_RES
<222> LOCATION: (21)..(21)
<223> OTHER INFORMATION: PHOSPHORYLATION; tyrosine at position 21 is
      phosphorylated

<400> SEQUENCE: 191

Cys Arg Asp Asp Ser Phe Phe Gly Glu Thr Ser His Asn Tyr His Lys
1               5                   10                  15

Phe Asp Ser Glu Tyr Glu Arg
            20

<210> SEQ ID NO 192
<211> LENGTH: 25
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION; tyrosine at position 10 is
      phosphorylated

<400> SEQUENCE: 192

Gln Lys Thr Asn Val Phe Ala Pro Asp Tyr Ile Ala Gly Val Ser Pro
1               5                   10                  15

Phe Val Glu Asn Asp Ile Ser Ser Arg
20                  25

<210> SEQ ID NO 193
<211> LENGTH: 13
<212> TYPE: PRT
```

```
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated

<400> SEQUENCE: 193

Phe Tyr Ile Asp Pro Tyr Lys Leu Leu Pro Leu Gln Arg
1               5                   10

<210> SEQ ID NO 194
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; tyrosine at position 4 is
      phosphorylated

<400> SEQUENCE: 194

Tyr Asn Pro Tyr Thr Thr Arg Pro Asn Arg
1               5                   10

<210> SEQ ID NO 195
<211> LENGTH: 22
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: PHOSPHORYLATION; tyrosine at position 13 is
      phosphorylated

<400> SEQUENCE: 195

Ile Cys Arg Asp Leu Ile Thr Ser Gly Ser Ser Asn Tyr Ala Tyr Val
1               5                   10                  15

Asn Phe Gln His Thr Lys
            20

<210> SEQ ID NO 196
<211> LENGTH: 22
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: PHOSPHORYLATION; tyrosine at position 15 is
      phosphorylated

<400> SEQUENCE: 196

Ile Cys Arg Asp Leu Ile Thr Ser Gly Ser Ser Asn Tyr Ala Tyr Val
1               5                   10                  15

Asn Phe Gln His Thr Lys
            20

<210> SEQ ID NO 197
<211> LENGTH: 24
<212> TYPE: PRT
<213> ORGANISM: Homo sapiens
<220> FEATURE:
<221> NAME/KEY: MOD_RES
<222> LOCATION: (21)..(21)
<223> OTHER INFORMATION: PHOSPHORYLATION; tyrosine at position 21 is
      phosphorylated

<400> SEQUENCE: 197
```

```
Gly Gly Ser Gly Ser His Asn Trp Gly Thr Val Lys Asp Glu Leu Thr
1               5                   10                  15

Glu Ser Pro Lys Tyr Ile Gln Lys
            20
```

<210> SEQ ID NO 198
<211> LENGTH: 19
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 198

```
Gly Pro Pro Leu Glu Ala Tyr Thr Ile Gln Gly Gln Tyr Ala Ile Pro
1               5                   10                  15

Gln Pro Asp
```

<210> SEQ ID NO 199
<211> LENGTH: 10
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated

<400> SEQUENCE: 199

```
His Arg Ile Tyr Glu Tyr Val Glu Ser Arg
1               5                   10
```

<210> SEQ ID NO 200
<211> LENGTH: 12
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION; tyrosine at position 5 is
      phosphorylated

<400> SEQUENCE: 200

```
Asn Gln Pro Ile Tyr Ile Gln Tyr Ser Asn His Lys
1               5                   10
```

<210> SEQ ID NO 201
<211> LENGTH: 8
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 201

```
Leu Ala Glu Leu Ser Asp Tyr Arg
1               5
```

<210> SEQ ID NO 202
<211> LENGTH: 8
<212> TYPE: PRT
<213> ORGANISM: Homo sapiens
<220> FEATURE:
<221> NAME/KEY: MOD_RES

```
<222> LOCATION: (5)..(5)
<223> OTHER INFORMATION: PHOSPHORYLATION; tyrosine at position 5 is
      phosphorylated

<400> SEQUENCE: 202

Ile Glu Ala Val Tyr Val Ser Arg
1               5

<210> SEQ ID NO 203
<211> LENGTH: 14
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 203

Ser Asp Val Asn Lys Glu Tyr Tyr Thr Gln Asn Met Glu Arg
1               5                   10

<210> SEQ ID NO 204
<211> LENGTH: 19
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION; tyrosine at position 5 is
      phosphorylated

<400> SEQUENCE: 204

Asn Gln Gly Gly Tyr Asp Arg Tyr Ser Gly Gly Asn Tyr Arg Asp Asn
1               5                   10                  15

Tyr Asp Asn

<210> SEQ ID NO 205
<211> LENGTH: 19
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: PHOSPHORYLATION; tyrosine at position 18 is
      phosphorylated

<400> SEQUENCE: 205

Asp Tyr Asn Gly Arg Asn Gln Gly Gly Tyr Asp Arg Tyr Ser Gly Gly
1               5                   10                  15

Asn Tyr Arg

<210> SEQ ID NO 206
<211> LENGTH: 19
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at position 9 is
      phosphorylated

<400> SEQUENCE: 206

Gly Gly His Met Asp Asp Gly Gly Tyr Ser Met Asn Phe Asn Met Ser
1               5                   10                  15

Ser Ser Arg
```

<210> SEQ ID NO 207
<211> LENGTH: 12
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; tyrosine at position 3 is
      phosphorylated

<400> SEQUENCE: 207

Asp Ser Tyr Ser Ser Arg Asp Tyr Pro Ser Ser Arg
1               5                   10

<210> SEQ ID NO 208
<211> LENGTH: 14
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION; tyrosine at position 11 is
      phosphorylated

<400> SEQUENCE: 208

Asp Tyr Gly His Ser Ser Ser Arg Asp Asp Tyr Pro Ser Arg
1               5                   10

<210> SEQ ID NO 209
<211> LENGTH: 30
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: PHOSPHORYLATION; tyrosine at position 14 is
      phosphorylated

<400> SEQUENCE: 209

Glu Pro Leu Asp Gly Asp Gly His Glu Ser Ala Glu Pro Tyr Ala Lys
1               5                   10                  15

His Met Lys Pro Ser Val Glu Pro Ala Pro Pro Val Ser Arg
            20                  25                  30

<210> SEQ ID NO 210
<211> LENGTH: 12
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION; tyrosine at position 5 is
      phosphorylated

<400> SEQUENCE: 210

Ser Gln Pro Val Tyr Ile Gln Tyr Ser Asn His Arg
1               5                   10

<210> SEQ ID NO 211
<211> LENGTH: 18
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; tyrosine at position 4 is
      phosphorylated

<400> SEQUENCE: 211

```
Leu Asp His Tyr Ala Ile Ile Lys Phe Pro Leu Thr Thr Glu Ser Ala
1               5                   10                  15

Met Lys

<210> SEQ ID NO 212
<211> LENGTH: 10
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated

<400> SEQUENCE: 212

Lys Leu Asp Glu Leu Tyr Gly Thr Trp Arg
1               5                   10

<210> SEQ ID NO 213
<211> LENGTH: 17
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated

<400> SEQUENCE: 213

Glu Gln Glu Arg Ala Tyr Ile Val Gln Leu Gln Ile Glu Asp Leu Thr
1               5                   10                  15

Arg

<210> SEQ ID NO 214
<211> LENGTH: 17
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: PHOSPHORYLATION; tyrosine at position 14 is
      phosphorylated

<400> SEQUENCE: 214

Gln Leu Ala Leu Glu Thr Ile Asp Ile Asn Lys Asp Pro Tyr Phe Met
1               5                   10                  15

Lys

<210> SEQ ID NO 215
<211> LENGTH: 23
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: PHOSPHORYLATION; tyrosine at position 14 is
      phosphorylated

<400> SEQUENCE: 215

Asp Ala Lys Asp Lys Leu Glu Ser Glu Met Glu Asp Ala Tyr His Glu
1               5                   10                  15

His Gln Ala Asn Leu Leu Arg
            20

<210> SEQ ID NO 216
```

```
<211> LENGTH: 13
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION; tyrosine at position 5 is
      phosphorylated

<400> SEQUENCE: 216

Gly Arg Glu Glu Tyr Glu Gly Pro Asn Lys Lys Pro Arg
1               5                   10

<210> SEQ ID NO 217
<211> LENGTH: 26
<212> TYPE: PRT
<213> ORGANISM: Homo sapiens
<220> FEATURE:
<221> NAME/KEY: MOD_RES
<222> LOCATION: (22)..(22)
<223> OTHER INFORMATION: PHOSPHORYLATION; tyrosine at position 22 is
      phosphorylated

<400> SEQUENCE: 217

His Val Gly Asn Arg Ala Asn Pro Asp Pro Asn Cys Cys Leu Gly Val
1               5                   10                  15

Phe Gly Leu Ser Leu Tyr Thr Thr Glu Arg
            20                  25

<210> SEQ ID NO 218
<211> LENGTH: 8
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION; tyrosine at position 5 is
      phosphorylated

<400> SEQUENCE: 218

Val Gly Asp Val Tyr Ile Pro Arg
1               5

<210> SEQ ID NO 219
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; tyrosine at position 4 is
      phosphorylated

<400> SEQUENCE: 219

Ala Phe Gly Tyr Tyr Gly Pro Leu Arg
1               5

<210> SEQ ID NO 220
<211> LENGTH: 15
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at position 9 is
      phosphorylated

<400> SEQUENCE: 220

Pro Arg Thr Ser His Arg Arg Ser Tyr Ser Gly Ser Arg Ser Arg
```

```
<210> SEQ ID NO 221
<211> LENGTH: 12
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION; tyrosine at position 5 is
      phosphorylated

<400> SEQUENCE: 221

Gly Ser Pro His Tyr Phe Ser Pro Phe Arg Pro Tyr
1               5                   10

<210> SEQ ID NO 222
<211> LENGTH: 20
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated

<400> SEQUENCE: 222

Ala Ala Ala Glu Ile Tyr Glu Glu Phe Leu Ala Ala Phe Glu Gly Ser
1               5                   10                  15

Asp Gly Asn Lys
            20

<210> SEQ ID NO 223
<211> LENGTH: 11
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; tyrosine at position 3 is
      phosphorylated

<400> SEQUENCE: 223

Met Gln Tyr Phe Gln Pro Thr Ile Gln Glu Lys
1               5                   10

<210> SEQ ID NO 224
<211> LENGTH: 13
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 224

Gly Gly Asn Arg Phe Glu Pro Tyr Ala Asn Pro Thr Lys
1               5                   10

<210> SEQ ID NO 225
<211> LENGTH: 15
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION; tyrosine at position 11 is
      phosphorylated
```

```
<400> SEQUENCE: 225

Asp Lys Phe Asn Glu Cys Gly His Val Leu Tyr Ala Asp Ile Lys
1               5                   10                  15

<210> SEQ ID NO 226
<211> LENGTH: 18
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION; tyrosine at position 5 is
      phosphorylated

<400> SEQUENCE: 226

Asp Ile Val Glu Tyr Tyr Asn Asp Ser Asn Gly Ser His Val Leu Gln
1               5                   10                  15

Gly Arg

<210> SEQ ID NO 227
<211> LENGTH: 30
<212> TYPE: PRT
<213> ORGANISM: Homo sapiens
<220> FEATURE:
<221> NAME/KEY: MOD_RES
<222> LOCATION: (30)..(30)
<223> OTHER INFORMATION: PHOSPHORYLATION; tyrosine at position 30 is
      phosphorylated

<400> SEQUENCE: 227

Gly Gln Asp Met Val Ser Pro Glu Ala Thr Asn Ser Ser Ser Ser
1               5                   10                  15

Phe Ser Ser Pro Ser Ser Ala Gly Arg His Val Arg Ser Tyr
            20                  25                  30

<210> SEQ ID NO 228
<211> LENGTH: 21
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: PHOSPHORYLATION; tyrosine at position 18 is
      phosphorylated

<400> SEQUENCE: 228

Cys Lys Pro Ile Arg Ala Thr Gln Lys Thr Tyr Phe Arg Asn Asn Tyr
1               5                   10                  15

Asn Tyr Val Ile Arg
            20

<210> SEQ ID NO 229
<211> LENGTH: 37
<212> TYPE: PRT
<213> ORGANISM: Homo sapiens
<220> FEATURE:
<221> NAME/KEY: MOD_RES
<222> LOCATION: (34)..(34)
<223> OTHER INFORMATION: PHOSPHORYLATION; tyrosine at position 34 is
      phosphorylated

<400> SEQUENCE: 229

Ile Pro Ser Pro Ser Phe Gly Gln Gln Thr Phe Ser Pro Gln Ser Ser
1               5                   10                  15

Pro Met Pro Gly Val Ala Gly Gly Ser Gly Gln Ser Lys Val Met Ala
```

```
                    20                  25                  30

Asn Tyr Met Tyr Lys
        35

<210> SEQ ID NO 230
<211> LENGTH: 37
<212> TYPE: PRT
<213> ORGANISM: Homo sapiens
<220> FEATURE:
<221> NAME/KEY: MOD_RES
<222> LOCATION: (36)..(36)
<223> OTHER INFORMATION: PHOSPHORYLATION; tyrosine at position 36 is
      phosphorylated

<400> SEQUENCE: 230

Ile Pro Ser Pro Ser Phe Gly Gln Gln Thr Phe Ser Pro Gln Ser Ser
1               5                   10                  15

Pro Met Pro Gly Val Ala Gly Gly Ser Gly Gln Ser Lys Val Met Ala
                20                  25                  30

Asn Tyr Met Tyr Lys
        35

<210> SEQ ID NO 231
<211> LENGTH: 24
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION; tyrosine at position 5 is
      phosphorylated

<400> SEQUENCE: 231

Lys Ile Val Ala Tyr Gly Lys Glu Gly His Met Leu Gln Thr Phe Asp
1               5                   10                  15

Tyr Ser Arg Asp Pro Gln Glu Arg
                20

<210> SEQ ID NO 232
<211> LENGTH: 16
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 232

Lys Ala Asp Arg Glu Ser Arg Tyr Glu Glu Glu Glu Glu Gln Ser Arg
1               5                   10                  15

<210> SEQ ID NO 233
<211> LENGTH: 32
<212> TYPE: PRT
<213> ORGANISM: Homo sapiens
<220> FEATURE:
<221> NAME/KEY: MOD_RES
<222> LOCATION: (19)..(19)
<223> OTHER INFORMATION: PHOSPHORYLATION; tyrosine at position 19 is
      phosphorylated

<400> SEQUENCE: 233

Pro Cys Thr Leu Thr Phe Lys His Cys Ala Glu Gln Pro Ser His Ala
1               5                   10                  15

Arg Thr Tyr Ser Ser Asn Thr Thr Leu Leu Asp Ala Lys Val Trp Arg
```

```
                20                  25                  30

<210> SEQ ID NO 234
<211> LENGTH: 25
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at position 9 is
      phosphorylated

<400> SEQUENCE: 234

Phe Val Glu Gly Val Asp Ser Asp Tyr His Asp Glu Asn Met Tyr Tyr
1               5                   10                  15

Ser Gln Ser Ser Met Phe Pro His Arg
            20                  25

<210> SEQ ID NO 235
<211> LENGTH: 25
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: PHOSPHORYLATION; tyrosine at position 15 is
      phosphorylated

<400> SEQUENCE: 235

Phe Val Glu Gly Val Asp Ser Asp Tyr His Asp Glu Asn Met Tyr Tyr
1               5                   10                  15

Ser Gln Ser Ser Met Phe Pro His Arg
            20                  25

<210> SEQ ID NO 236
<211> LENGTH: 25
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: PHOSPHORYLATION; tyrosine at position 16 is
      phosphorylated

<400> SEQUENCE: 236

Phe Val Glu Gly Val Asp Ser Asp Tyr His Asp Glu Asn Met Tyr Tyr
1               5                   10                  15

Ser Gln Ser Ser Met Phe Pro His Arg
            20                  25

<210> SEQ ID NO 237
<211> LENGTH: 18
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION tyrosine at position 7 is
      phosphorylated

<400> SEQUENCE: 237

Ile Thr Leu Ser Ala Ile Tyr Lys Trp Ile Thr Asp Asn Phe Cys Tyr
1               5                   10                  15

Phe Arg

<210> SEQ ID NO 238
```

```
<211> LENGTH: 18
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: PHOSPHORYLATION; tyrosine at position 16 is
      phosphorylated

<400> SEQUENCE: 238

Ile Thr Leu Ser Ala Ile Tyr Lys Trp Ile Thr Asp Asn Phe Cys Tyr
1               5                   10                  15

Phe Arg

<210> SEQ ID NO 239
<211> LENGTH: 18
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: PHOSPHORYLATION; tyrosine at position 13 is
      phosphorylated

<400> SEQUENCE: 239

Val Phe Ala Phe Asp Ala Thr Ala Arg Pro Pro Gly Tyr Glu Phe Glu
1               5                   10                  15

Leu Lys

<210> SEQ ID NO 240
<211> LENGTH: 15
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; tyrosine at position 3 is
      phosphorylated

<400> SEQUENCE: 240

Asn Ser Tyr Tyr Pro Thr Pro Pro Ala Pro Met Pro Gly Pro Thr
1               5                   10                  15

<210> SEQ ID NO 241
<211> LENGTH: 31
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: PHOSPHORYLATION; tyrosine at position 18 is
      phosphorylated

<400> SEQUENCE: 241

Thr Gly Leu Val Thr Gly Pro Asp Gly Lys Gly Met Asn Pro Pro Ser
1               5                   10                  15

Tyr Tyr Thr Gln Pro Ala Pro Ile Pro Asn Asn Asn Pro Ile Thr
                20                  25                  30

<210> SEQ ID NO 242
<211> LENGTH: 16
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated
```

```
<400> SEQUENCE: 242

Gln Glu Thr Phe Val Tyr Glu Met Glu Ser His Ala Ile Gly Lys Lys
1               5                   10                  15

<210> SEQ ID NO 243
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 243

Leu Ser Arg Ser Ile Arg Gln Tyr Tyr Lys Lys Gly Ile Ile Arg Lys
1               5                   10                  15

Pro Asp Ile Ser Gln Arg Leu Val Tyr Gln Phe Val His Pro Ile
            20                  25                  30

<210> SEQ ID NO 244
<211> LENGTH: 31
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at position 9 is
      phosphorylated

<400> SEQUENCE: 244

Leu Ser Arg Ser Ile Arg Gln Tyr Tyr Lys Lys Gly Ile Ile Arg Lys
1               5                   10                  15

Pro Asp Ile Ser Gln Arg Leu Val Tyr Gln Phe Val His Pro Ile
            20                  25                  30

<210> SEQ ID NO 245
<211> LENGTH: 25
<212> TYPE: PRT
<213> ORGANISM: Homo sapiens
<220> FEATURE:
<221> NAME/KEY: MOD_RES
<222> LOCATION: (21)..(21)
<223> OTHER INFORMATION: PHOSPHORYLATION; tyrosine at position 21 is
      phosphorylated

<400> SEQUENCE: 245

Lys Ala Thr Lys Pro Met Ala Glu Ser Pro Lys Asn Gly Gly Asp Val
1               5                   10                  15

Val Pro Gln Tyr Tyr Lys Asp Pro Lys
            20                  25

<210> SEQ ID NO 246
<211> LENGTH: 17
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION; tyrosine at position 10 is
      phosphorylated

<400> SEQUENCE: 246

Ile Asp Thr Leu Met Tyr Leu Leu Ala Tyr Pro Gln Lys Pro Met Val
1               5                   10                  15
```

Lys

```
<210> SEQ ID NO 247
<211> LENGTH: 22
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION; tyrosine at position 2 is
      phosphorylated

<400> SEQUENCE: 247

Gly Tyr Gln Asn Lys Tyr Pro Lys Ala Glu Met Thr Leu Ile Pro Met
1               5                   10                  15

Lys Gly Glu Phe Ser Arg
            20

<210> SEQ ID NO 248
<211> LENGTH: 30
<212> TYPE: PRT
<213> ORGANISM: Homo sapiens
<220> FEATURE:
<221> NAME/KEY: MOD_RES
<222> LOCATION: (28)..(28)
<223> OTHER INFORMATION: PHOSPHORYLATION; tyrosine at position 28 is
      phosphorylated

<400> SEQUENCE: 248

Thr Ile His Ser Val Leu Glu Thr Ser Pro Ala Val Leu Leu Lys Glu
1               5                   10                  15

Ile Ile Leu Val Asp Asp Leu Ser Asp Arg Val Tyr Leu Lys
            20                  25                  30

<210> SEQ ID NO 249
<211> LENGTH: 22
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated

<400> SEQUENCE: 249

Val Gly Lys Gly Ile Tyr Phe Ala Ser Glu Asn Ser Lys Ser Ala Gly
1               5                   10                  15

Tyr Val Ile Gly Met Lys
            20

<210> SEQ ID NO 250
<211> LENGTH: 22
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: PHOSPHORYLATION; tyrosine at position 17 is
      phosphorylated

<400> SEQUENCE: 250

Val Gly Lys Gly Ile Tyr Phe Ala Ser Glu Asn Ser Lys Ser Ala Gly
1               5                   10                  15

Tyr Val Ile Gly Met Lys
            20
```

```
<210> SEQ ID NO 251
<211> LENGTH: 22
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION; tyrosine at position 5 is
      phosphorylated

<400> SEQUENCE: 251

Gly Asp Ser Ala Tyr Leu Ser Gly Asp Val Leu Val Met Asp Glu Leu
1               5                   10                  15

Gly Tyr Met Tyr Phe Arg
            20

<210> SEQ ID NO 252
<211> LENGTH: 22
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: PHOSPHORYLATION; tyrosine at position 18 is
      phosphorylated

<400> SEQUENCE: 252

Gly Asp Ser Ala Tyr Leu Ser Gly Asp Val Leu Val Met Asp Glu Leu
1               5                   10                  15

Gly Tyr Met Tyr Phe Arg
            20

<210> SEQ ID NO 253
<211> LENGTH: 22
<212> TYPE: PRT
<213> ORGANISM: Homo sapiens
<220> FEATURE:
<221> NAME/KEY: MOD_RES
<222> LOCATION: (20)..(20)
<223> OTHER INFORMATION: PHOSPHORYLATION; tyrosine at position 20 is
      phosphorylated

<400> SEQUENCE: 253

Gly Asp Ser Ala Tyr Leu Ser Gly Asp Val Leu Val Met Asp Glu Leu
1               5                   10                  15

Gly Tyr Met Tyr Phe Arg
            20

<210> SEQ ID NO 254
<211> LENGTH: 25
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION; tyrosine at position 2 is
      phosphorylated

<400> SEQUENCE: 254

Arg Tyr Thr Gln Gly Val Met Thr Gly Glu Ser Thr Ala Gly Val Met
1               5                   10                  15

Ile Ser Leu Ser Arg Ile Leu Thr Lys
            20                  25

<210> SEQ ID NO 255
<211> LENGTH: 30
<212> TYPE: PRT
```

```
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at positin 9 is
      phosphorylated

<400> SEQUENCE: 255

Glu Pro Gly Arg Pro Thr Pro Thr Tyr His Leu Val Pro Asn Thr Ser
1               5                   10                  15

Gln Ser Gln Val Glu Glu Asp Val Ser Ser Pro Pro Gln Arg
            20                  25                  30

<210> SEQ ID NO 256
<211> LENGTH: 7
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated

<400> SEQUENCE: 256

Leu Ile Ala Glu Lys Tyr Arg
1               5

<210> SEQ ID NO 257
<211> LENGTH: 18
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION; tyrosine at position 12 is
      phosphorylated

<400> SEQUENCE: 257

Val Ala Thr Ala Leu Thr Leu Met Thr Gly Leu Tyr Gln Thr Ser Trp
1               5                   10                  15

Gly Arg

<210> SEQ ID NO 258
<211> LENGTH: 11
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION; tyrosine at position 5 is
      phosphorylated

<400> SEQUENCE: 258

Met Val Pro Gly Tyr Leu Leu Val Gln Tyr Phe
1               5                   10

<210> SEQ ID NO 259
<211> LENGTH: 34
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PHOSPHORYLATION; tyrosine at position 1 is
      phosphorylated

<400> SEQUENCE: 259

Tyr Pro Asn Trp Ser Met Val Leu Gly Trp Leu Met Leu Ala Cys Ser
```

-continued

```
1               5                   10                  15
Val Ile Trp Ile Pro Ile Met Phe Val Ile Lys Met His Leu Ala Pro
                20                  25                  30
Gly Arg
```

<210> SEQ ID NO 260
<211> LENGTH: 32
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: PHOSPHORYLATION; tyrosine at position 17 is
      phosphorylated

<400> SEQUENCE: 260

```
Val Ile Val Ser Leu Thr Val Tyr Thr Leu Phe Met Ile Asp Gly Tyr
1               5                   10                  15

Tyr Asn Val Leu Trp Glu Lys Leu Asp Asp Tyr Val Tyr Val Arg
                20                  25                  30
```

<210> SEQ ID NO 261
<211> LENGTH: 18
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated

<400> SEQUENCE: 261

```
Met Leu Glu Asp Gly Tyr Glu Gln Leu Arg Gln Leu Ser Gln His Ala
1               5                   10                  15

Met Lys
```

<210> SEQ ID NO 262
<211> LENGTH: 22
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; tyrosine at position 4 is
      phosphorylated

<400> SEQUENCE: 262

```
Asn Ser Asn Tyr Cys Leu Pro Ser Tyr Thr Ala Tyr Lys Asn Tyr Asp
1               5                   10                  15

Tyr Ser Glu Pro Gly Arg
                20
```

<210> SEQ ID NO 263
<211> LENGTH: 22
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: PHOSPHORYLATION; tyrosine at position 15 is
      phosphorylated

<400> SEQUENCE: 263

```
Asn Ser Asn Tyr Cys Leu Pro Ser Tyr Thr Ala Tyr Lys Asn Tyr Asp
1               5                   10                  15
```

Tyr Ser Glu Pro Gly Arg
            20

<210> SEQ ID NO 264
<211> LENGTH: 22
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: PHOSPHORYLATION; tyrosine at position 17 is
      phosphorylated

<400> SEQUENCE: 264

Asn Ser Asn Tyr Cys Leu Pro Ser Tyr Thr Ala Tyr Lys Asn Tyr Asp
1               5                   10                  15

Tyr Ser Glu Pro Gly Arg
            20

<210> SEQ ID NO 265
<211> LENGTH: 28
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: PHOSPHORYLATION; tyrosine at position 17 is
      phosphorylated

<400> SEQUENCE: 265

Glu Ser Glu Thr Ser Val Thr Thr Ala Gln Ala Ala Gly Asp Pro Glu
1               5                   10                  15

Tyr Leu Glu Gln Pro Ser Arg Ser Asp Phe Ser Lys
            20                  25

<210> SEQ ID NO 266
<211> LENGTH: 21
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: PHOSPHORYLATION; tyrosine at position 14 is
      phosphorylated

<400> SEQUENCE: 266

Ser Phe Thr Asp Leu Glu Glu Leu Asp Glu Thr Glu Leu Tyr Met Cys
1               5                   10                  15

His Lys Cys Lys Lys
            20

<210> SEQ ID NO 267
<211> LENGTH: 13
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION; tyrosine at position 2 is
      phosphorylated

<400> SEQUENCE: 267

Leu Tyr Leu Gln Glu Gln Glu Leu Asn Ala Arg Ala Arg
1               5                   10

<210> SEQ ID NO 268
<211> LENGTH: 20

```
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION; tyrosine at position 12 is
      phosphorylated

<400> SEQUENCE: 268

Ile Leu Arg Leu Lys Asn Gln Leu Asn Glu Asp Tyr Lys Thr Val Asn
1               5                   10                  15

Asn Leu Leu Lys
            20

<210> SEQ ID NO 269
<211> LENGTH: 24
<212> TYPE: PRT
<213> ORGANISM: Homo sapiens
<220> FEATURE:
<221> NAME/KEY: MOD_RES
<222> LOCATION: (21)..(21)
<223> OTHER INFORMATION: PHOSPHORYLATION; tyrosine at position 21 is
      phosphorylated

<400> SEQUENCE: 269

Lys Ala Glu Leu Leu Asp Asn Glu Lys Pro Ala Ala Val Val Ala Pro
1               5                   10                  15

Ile Thr Thr Gly Tyr Thr Val Lys
            20

<210> SEQ ID NO 270
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 270

Cys Glu Lys His Ala His Leu Tyr Arg Lys Leu Ile Thr Asn Ile Leu
1               5                   10                  15

Gly Gly Cys Ile Gln Met Val Leu Gly Gln Ile Glu Asp His Arg
            20                  25                  30

<210> SEQ ID NO 271
<211> LENGTH: 21
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at position 9 is
      phosphorylated

<400> SEQUENCE: 271

His Ile Leu Gly Ile Pro Val Asn Tyr Gln Asp Val Ala Ser Ile Asp
1               5                   10                  15

Pro Glu Tyr Ala Lys
            20

<210> SEQ ID NO 272
<211> LENGTH: 21
<212> TYPE: PRT
<213> ORGANISM: Homo sapiens
<220> FEATURE:
```

```
<221> NAME/KEY: MOD_RES
<222> LOCATION: (19)..(19)
<223> OTHER INFORMATION: PHOSPHORYLATION; tyrosine at position 19 is
      phosphorylated

<400> SEQUENCE: 272

His Ile Leu Gly Ile Pro Val Asn Tyr Gln Asp Val Ala Ser Ile Asp
1               5                   10                  15

Pro Glu Tyr Ala Lys
            20

<210> SEQ ID NO 273
<211> LENGTH: 8
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated

<400> SEQUENCE: 273

Thr Pro Gly Ser Ser Tyr Pro Arg
1               5

<210> SEQ ID NO 274
<211> LENGTH: 39
<212> TYPE: PRT
<213> ORGANISM: Homo sapiens
<220> FEATURE:
<221> NAME/KEY: MOD_RES
<222> LOCATION: (28)..(28)
<223> OTHER INFORMATION: PHOSPHORYLATION; tyrosine at position 28 is
      phosphorylated

<400> SEQUENCE: 274

Asp Gly Gly Ala Pro Gly Pro Gln Pro His Gly Glu Pro Pro Gly Gly
1               5                   10                  15

Pro Asp Ala Val Asp Gly Val Met Asn Gly Glu Tyr Tyr Gln Glu Ser
            20                  25                  30

Asn Gly Pro Thr Asp Ser Tyr
            35

<210> SEQ ID NO 275
<211> LENGTH: 30
<212> TYPE: PRT
<213> ORGANISM: Homo sapiens
<220> FEATURE:
<221> NAME/KEY: MOD_RES
<222> LOCATION: (28)..(28)
<223> OTHER INFORMATION: PHOSPHORYLATION; tyrosine at position 28 is
      phosphorylated

<400> SEQUENCE: 275

Gly Gly Ala Pro Gly Pro Gln Pro His Gly Glu Pro Pro Gly Gly Pro
1               5                   10                  15

Asp Ala Val Asp Gly Val Met Asn Gly Glu Tyr Tyr Gln Glu
            20                  25                  30

<210> SEQ ID NO 276
<211> LENGTH: 19
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
```

-continued phosphorylated

<400> SEQUENCE: 276

Asp Met Gly Ser Cys Glu Ile Tyr Pro Gln Thr Ile Gln His Asn Pro
1               5                   10                  15

Asn Gly Arg

<210> SEQ ID NO 277
<211> LENGTH: 18
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 277

Cys Pro Glu Ala Val Ile Pro Tyr Ala Asn His Glu Leu Lys Glu Glu
1               5                   10                  15

Asn Arg

<210> SEQ ID NO 278
<211> LENGTH: 24
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PHOSPHORYLATION; tyrosine at position 1 is
      phosphorylated

<400> SEQUENCE: 278

Tyr Thr Phe Thr Leu Lys Thr His Pro Ser Val Pro Gly Ser Ile
1               5                   10                  15

Ala Phe Ser Leu Pro Gln Arg Lys
            20

<210> SEQ ID NO 279
<211> LENGTH: 14
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 279

Gln Tyr Ala Thr Leu Asp Val Tyr Asn Pro Phe Glu Thr Arg
1               5                   10

<210> SEQ ID NO 280
<211> LENGTH: 24
<212> TYPE: PRT
<213> ORGANISM: Homo sapiens
<220> FEATURE:
<221> NAME/KEY: MOD_RES
<222> LOCATION: (22)..(22)
<223> OTHER INFORMATION: PHOSPHORYLATION; tyrosine at position 22 is
      phosphorylated

<400> SEQUENCE: 280

Gln Pro Gly Pro Val Thr Asn Gly Gln Leu Gln Gln Pro Thr Thr Gly
1               5                   10                  15

Ala Ala Ser Gly Gly Tyr Ile Lys

```
<210> SEQ ID NO 281
<211> LENGTH: 11
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at position 9 is
      phosphorylated

<400> SEQUENCE: 281

Ser Val Phe Gly Gly Leu Val Asn Tyr Phe Lys
1               5                   10

<210> SEQ ID NO 282
<211> LENGTH: 18
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION; tyrosine at position 11 is
      phosphorylated

<400> SEQUENCE: 282

Gly Ala Gly Ser Ala Met Ser Thr Asp Ala Tyr Pro Lys Asn Pro His
1               5                   10                  15

Leu Arg

<210> SEQ ID NO 283
<211> LENGTH: 18
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: PHOSPHORYLATION; tyrosine at position 15 is
      phosphorylated

<400> SEQUENCE: 283

Phe Val Glu Val Met Ser Glu Tyr Asn Ala Thr Gln Ser Asp Tyr Arg
1               5                   10                  15

Glu Arg

<210> SEQ ID NO 284
<211> LENGTH: 11
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at position 9 is
      phosphorylated

<400> SEQUENCE: 284

Gly Leu Asp Arg Val Gln Asp Glu Tyr Ser Arg
1               5                   10

<210> SEQ ID NO 285
<211> LENGTH: 18
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: PHOSPHORYLATION; tyrosine at position 16 is
```

-continued

```
<400> SEQUENCE: 285

Leu Leu Asp Gly Thr His Gln Gln His Gly Phe Leu Ser Leu Thr Tyr
1               5                   10                  15

Thr Lys

<210> SEQ ID NO 286
<211> LENGTH: 20
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: PHOSPHORYLATION; tyrosine at position 16 is
      phosphorylated

<400> SEQUENCE: 286

Lys Asp Ser Gln Asn Lys Thr Leu Leu Lys Thr Leu Ala Glu Leu Tyr
1               5                   10                  15

Thr Tyr Asp Lys
            20

<210> SEQ ID NO 287
<211> LENGTH: 20
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: PHOSPHORYLATION; tyrosine at position 18 is
      phosphorylated

<400> SEQUENCE: 287

Lys Asp Ser Gln Asn Lys Thr Leu Leu Lys Thr Leu Ala Glu Leu Tyr
1               5                   10                  15

Thr Tyr Asp Lys
            20

<210> SEQ ID NO 288
<211> LENGTH: 13
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; tyrosine at position 4 is
      phosphorylated

<400> SEQUENCE: 288

Tyr Gly Ile Tyr Ala Val Glu Asn Glu His Met Asn Arg
1               5                   10
```

REAGENTS FOR THE DETECTION OF PROTEIN PHOSPHORYLATION IN LEUKEMIA SIGNALING PATHWAYS

RELATED APPLICATIONS

This application claims the benefit of, and priority to, PCT serial number PCT/US06/034050, filed Aug. 31, 2006, presently pending, the disclosure of which is incorporated herein, in its entirety, by reference.

FIELD OF THE INVENTION

The invention relates generally to antibodies and peptide reagents for the detection of protein phosphorylation, and to protein phosphorylation in cancer.

BACKGROUND OF THE INVENTION

The activation of proteins by post-translational modification is an important cellular mechanism for regulating most aspects of biological organization and control, including growth, development, homeostasis, and cellular communication. Protein phosphorylation, for example, plays a critical role in the etiology of many pathological conditions and diseases, including cancer, developmental disorders, autoimmune diseases, and diabetes. Yet, in spite of the importance of protein modification, it is not yet well understood at the molecular level, due to the extraordinary complexity of signaling pathways, and the slow development of technology necessary to unravel it.

Protein phosphorylation on a proteome-wide scale is extremely complex as a result of three factors: the large number of modifying proteins, e.g. kinases, encoded in the genome, the much larger number of sites on substrate proteins that are modified by these enzymes, and the dynamic nature of protein expression during growth, development, disease states, and aging. The human genome, for example, encodes over 520 different protein kinases, making them the most abundant class of enzymes known. See Hunter, *Nature* 411: 355-65 (2001). Most kinases phosphorylate many different substrate proteins, at distinct tyrosine, serine, and/or threonine residues. Indeed, it is estimated that one-third of all proteins encoded by the human genome are phosphorylated, and many are phosphorylated at multiple sites by different kinases. See Graves et al., *Pharmacol. Ther.* 82: 111-21 (1999).

Many of these phosphorylation sites regulate critical biological processes and may prove to be important diagnostic or therapeutic targets for molecular medicine. For example, of the more than 100 dominant oncogenes identified to date, 46 are protein kinases. See Hunter, supra. Understanding which proteins are modified by these kinases will greatly expand our understanding of the molecular mechanisms underlying oncogenic transformation. Therefore, the identification of, and ability to detect, phosphorylation sites on a wide variety of cellular proteins is crucially important to understanding the key signaling proteins and pathways implicated in the progression of diseases like cancer.

One form of cancer in which underlying signal transduction events are involved, but still poorly understood, is leukemia. Leukemia is a malignant disease of the bone marrow and blood, characterized by abnormal accumulation of blood cells, and is divided in four major categories. An estimated 33,500 new cases of leukemia will be diagnosed in the U.S. alone this year, affecting roughly 30,000 adults and 3,000 children, and close to 24,000 patients will die from the disease (Source: The Leukemia & Lymphoma Society (2004)). Depending of the cell type involved and the rate by which the disease progresses it can be defined as acute or chronic myelogenous leukemia (AML or CML), or acute and chronic lymphocytic leukemia (ALL or CLL). The acute forms of the disease rapidly progress, causing the accumulation of immature, functionless cells in the marrow and blood, which in turn results in anemia, immunodeficiency and coagulation deficiencies, respectively. Chronic forms of leukemia progress more slowly, allowing a greater number of mature, functional cells to be produced, which amass to high concentration in the blood over time.

More than half of adult leukemias occur in patients 67 years of age or older, and leukemia accounts for about 30% of all childhood cancers. The most common type of adult leukemia is acute myelogenous leukemia (AML), with an estimated 11,920 new cases annually. Without treatment patients rarely survive beyond 6-12 months, and despite continued development of new therapies, it remains fatal in 80% of treated patients (Source: The Leukemia & Lymphoma Society (2004)). The most common childhood leukemia is acute lymphocytic leukemia (ALL), but it can develop at any age. Chronic lymphocytic leukemia (CLL) is the second most prevalent adult leukemia, with approximately 8,200 new cases of CLL diagnosed annually in the U.S. The course of the disease is typically slower than acute forms, with a five-year relative survival of 74%. Chronic myelogenous leukemia (CML) is less prevalent, with about 4,600 new cases diagnosed each year in the U.S., and is rarely observed in children.

Most varieties of leukemia are generally characterized by genetic alterations associated with the etiology of the disease, and it has recently become apparent that, in many instances, such alterations (chromosomal translocations, deletions or point mutations) result in the constitutive activation of protein kinase genes, and their products, particularly tyrosine kinases. The most well known alteration is the oncogenic role of the chimeric BCR-Abl gene, which is generated by translocation of chromosome 9 to chromosome 22, creating the so-called Philadelphia chromosome characteristic of CML (see Nowell, *Science* 132:1497 (1960)). The resulting BCR-Abl kinase protein is constitutively active and elicits characteristic signaling pathways that have been shown to drive the proliferation and survival of CML cells (see Daley, *Science* 247: 824-830 (1990); Raitano et al., *Biochim. Biophys. Acta.* December 9; 1333(3): F201-16 (1997)). The recent success of Imanitib (also known as STI571 or Gleevec®), the first molecularly targeted compound designed to specifically inhibit the tyrosine kinase activity of BCR-Abl, provided critical confirmation of the central role of BCR-Abl signaling in the progression of CML (see Schindler et al., *Science* 289: 1938-1942 (2000); Nardi et al., *Curr. Opin. Hematol.* 11: 35-43 (2003)).

The success of Gleevec® now serves as a paradigm for the development of targeted drugs designed to block the activity of other tyrosine kinases known to be involved in leukemias and other malignancies (see, e.g., Sawyers, *Curr. Opin. Genet. Dev.* Feb; 12(1): 111-5 (2002); Druker, *Adv. Cancer Res.* 91:1-30 (2004)). For example, recent studies have demonstrated that mutations in the FLT3 gene occur in one third of adult patients with AML. FLT3 (Fms-like tyrosine kinase 3) is a member of the class III receptor tyrosine kinase (RTK) family including FMS, platelet-derived growth factor receptor (PDGFR) and c-KIT (see Rosnet et al., *Crit. Rev. Oncog.* 4: 595-613 (1993). In 20-27% of patients with AML, an internal tandem duplication in the juxta-membrane region of FLT3 can be detected (see Yokota et al., *Leukemia* 11: 1605-1609 (1997)). Another 7% of patients have mutations within the active loop of the second kinase domain, predominantly substitutions of aspartate residue 835 (D835), while additional mutations have been described (see Yamamoto et al., *Blood* 97: 2434-2439 (2001); Abu-Duhier et al., *Br. J. Haematol.* 113: 983-988 (2001)). Expression of mutated FLT3 receptors results in constitutive tyrosine phosphorylation of FLT3, and subsequent phosphorylation and activation of downstream molecules such as STAT5, Akt and MAPK, resulting in factor-independent growth of hematopoietic cell lines.

Altogether, FLT3 is the single most common activated gene in AML known to date. This evidence has triggered an intensive search for FLT3 inhibitors for clinical use leading to at least four compounds in advanced stages of clinical development, including: PKC412 (by Novartis), CEP-701 (by Cephalon), MLN518 (by Millenium Pharmaceuticals), and SU5614 (by Sugen/Pfizer) (see Stone et al., *Blood* (in press) (2004); Smith et al., *Blood* 103: 3669-3676 (2004); Clark et al., *Blood* 104: 2867-2872 (2004); and Spiekerman et al., *Blood* 101: 1494-1504 (2003)).

There is also evidence indicating that kinases such as FLT3, c-KIT and Abl are implicated in some cases of ALL (see Cools et al., *Cancer Res.* 64: 6385-6389 (2004); Hu, *Nat. Genet.* 36: 453-461 (2004); and Graux et al., *Nat. Genet.* 36: 1084-1089 (2004)). In contrast, very little is know regarding any causative role of protein kinases in CLL, except for a high correlation between high expression of the tyrosine kinase ZAP70 and the more aggressive form of the disease (see Rassenti et al., *N. Eng. J. Med.* 351: 893-901 (2004)).

Despite the identification of a few key molecules involved in progression of leukemia, the vast majority of signaling protein changes underlying this disease remains unknown. There is, therefore, relatively scarce information about kinase-driven signaling pathways and phosphorylation sites relevant to the different types of leukemia. This has hampered a complete and accurate understanding of how protein activation within signaling pathways is driving these complex cancers. Accordingly, there is a continuing and pressing need to unravel the molecular mechanisms of kinase-driven oncogenesis in leukemia by identifying the downstream signaling proteins mediating cellular transformation in this disease. Identifying particular phosphorylation sites on such signaling proteins and providing new reagents, such as phospho-specific antibodies and AQUA peptides, to detect and quantify them remains particularly important to advancing our understanding of the biology of this disease.

Presently, diagnosis of leukemia is made by tissue biopsy and detection of different cell surface markers. However, misdiagnosis can occur since some leukemia cases can be negative for certain markers, and because these markers may not indicate which genes or protein kinases may be deregulated. Although the genetic translocations and/or mutations characteristic of a particular form of leukemia can be sometimes detected, it is clear that other downstream effectors of constitutively active kinases having potential diagnostic, predictive, or therapeutic value, remain to be elucidated. Accordingly, identification of downstream signaling molecules and phosphorylation sites involved in different types of leukemia and development of new reagents to detect and quantify these sites and proteins may lead to improved diagnostic/prognostic markers, as well as novel drug targets, for the detection and treatment of this disease.

SUMMARY OF THE INVENTION

The invention discloses nearly 288 novel phosphorylation sites identified in signal transduction proteins and pathways underlying human Leukemias and provides new reagents, including phosphorylation-site specific antibodies and AQUA peptides, for the selective detection and quantification of these phosphorylated sites/proteins. Also provided are methods of using the reagents of the invention for the detection, quantification, and profiling of the disclosed phosphorylation sites.

BRIEF DESCRIPTION OF THE DRAWINGS

FIG. 2—Is a table (corresponding to Table 1) enumerating the Leukemia signaling protein phosphorylation sites disclosed herein: Column A=the name of the parent protein; Column B=the SwissProt accession number for the protein (human sequence); Column C=the protein type/classification; Column D=the tyrosine residue (in the parent protein amino acid sequence) at which phosphorylation occurs within the phosphorylation site; Column E=the phosphorylation site sequence encompassing the phosphorylatable residue (residue at which phosphorylation occurs (and corresponding to the respective entry in Column D) appears in lowercase; Column F=the type of leukemia in which the phosphorylation site was discovered; and Column G=the cell type(s), tissue(s) and/or patient(s) in which the phosphorylation site was discovered.

FIG. 3—FIG. 3A is an exemplary mass spectrograph depicting the detection of the tyrosine 630 phosphorylation site in BANK1 (see Row 10 in FIG. 2/Table 1), as further described in Example 1 (red and blue indicate ions detected in MS/MS spectrum); Y* indicates the phosphorylated tyrosine (shown as lowercase "y" in FIG. 2). FIG. 3b represents the data for the generation of FIG. 3A.

FIG. 4—FIG. 4A is an exemplary mass spectrograph depicting the detection of the tyrosine 289 phosphorylation site in FASN (see Row 10 in FIG. 2/Table 1), as further described in Example 1 (red and blue indicate ions detected in MS/MS spectrum); Y* indicates the phosphorylated tyrosine (shown as lowercase "y" in FIG. 2). FIG. 4B represents the data for the generation of FIG. 4A.

FIG. 7—FIG. 7A is an exemplary mass spectrograph depicting the detection of the tyrosine 189 phosphorylation site in RASGRP2 (see Row 105 in FIG. 2/Table 1), as further described in Example 1 (red and blue indicate ions detected in MS/MS spectrum); Y* indicates the phosphorylated tyrosine (shown as lowercase "y" in FIG. 2). FIG. 7B represents the data for the generation of FIG. 7A.

DETAILED DESCRIPTION OF THE INVENTION

Figure 1:
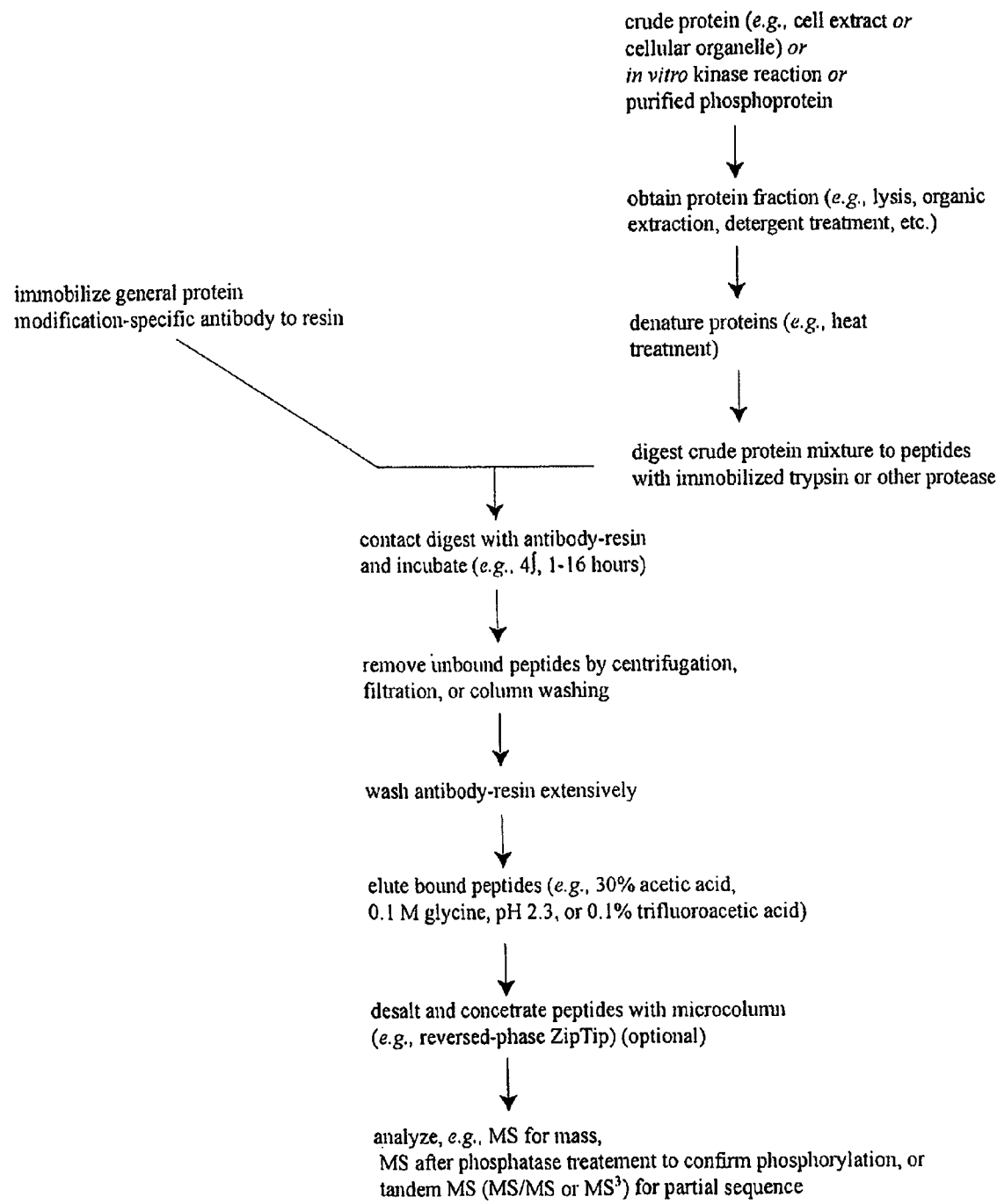
FIG. 1—Is a diagram broadly depicting the immunoaffinity isolation and mass-spectrometric characterization methodology (IAP) employed to identify the novel phosphorylation sites disclosed herein.
Figure 3A:
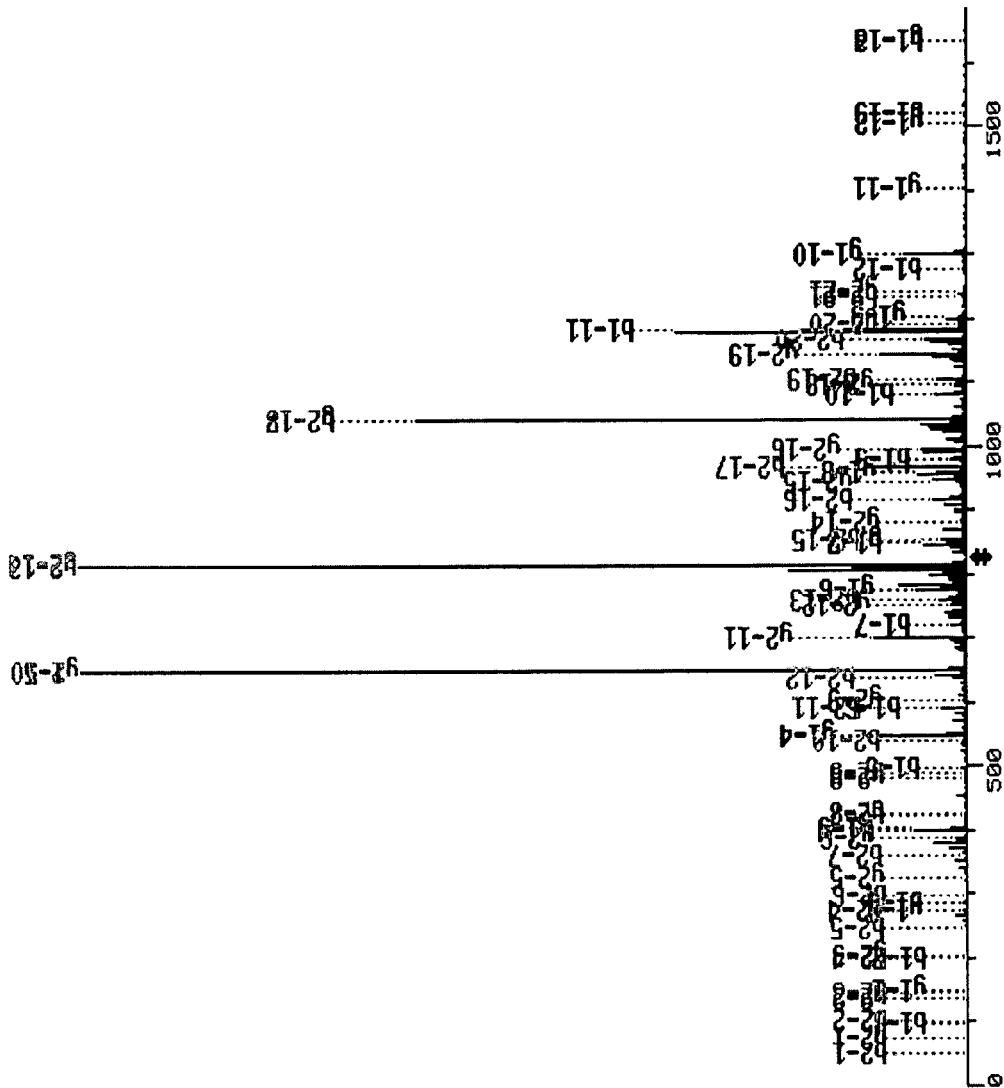
Figure 4A:
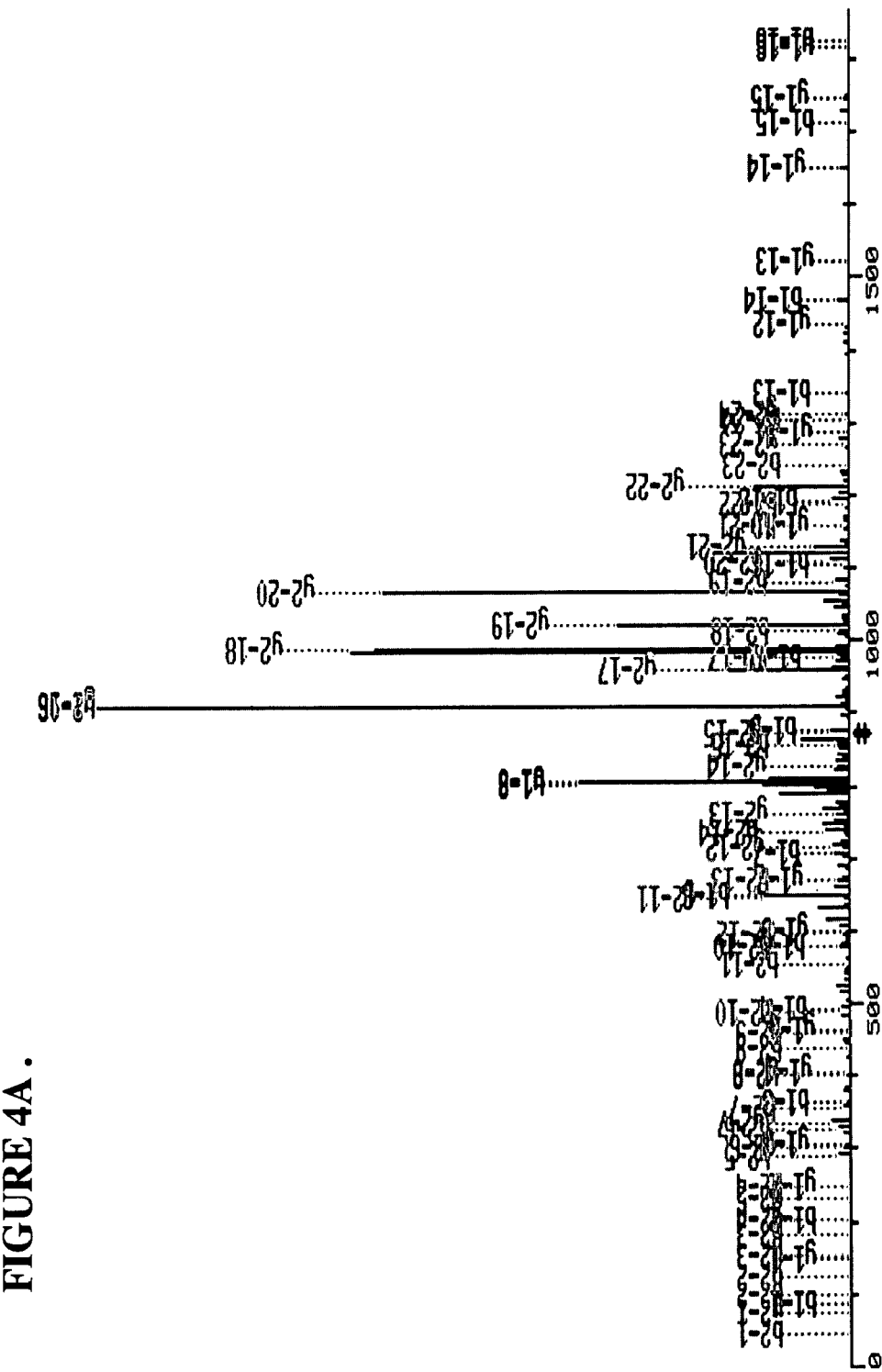
Figure 5:
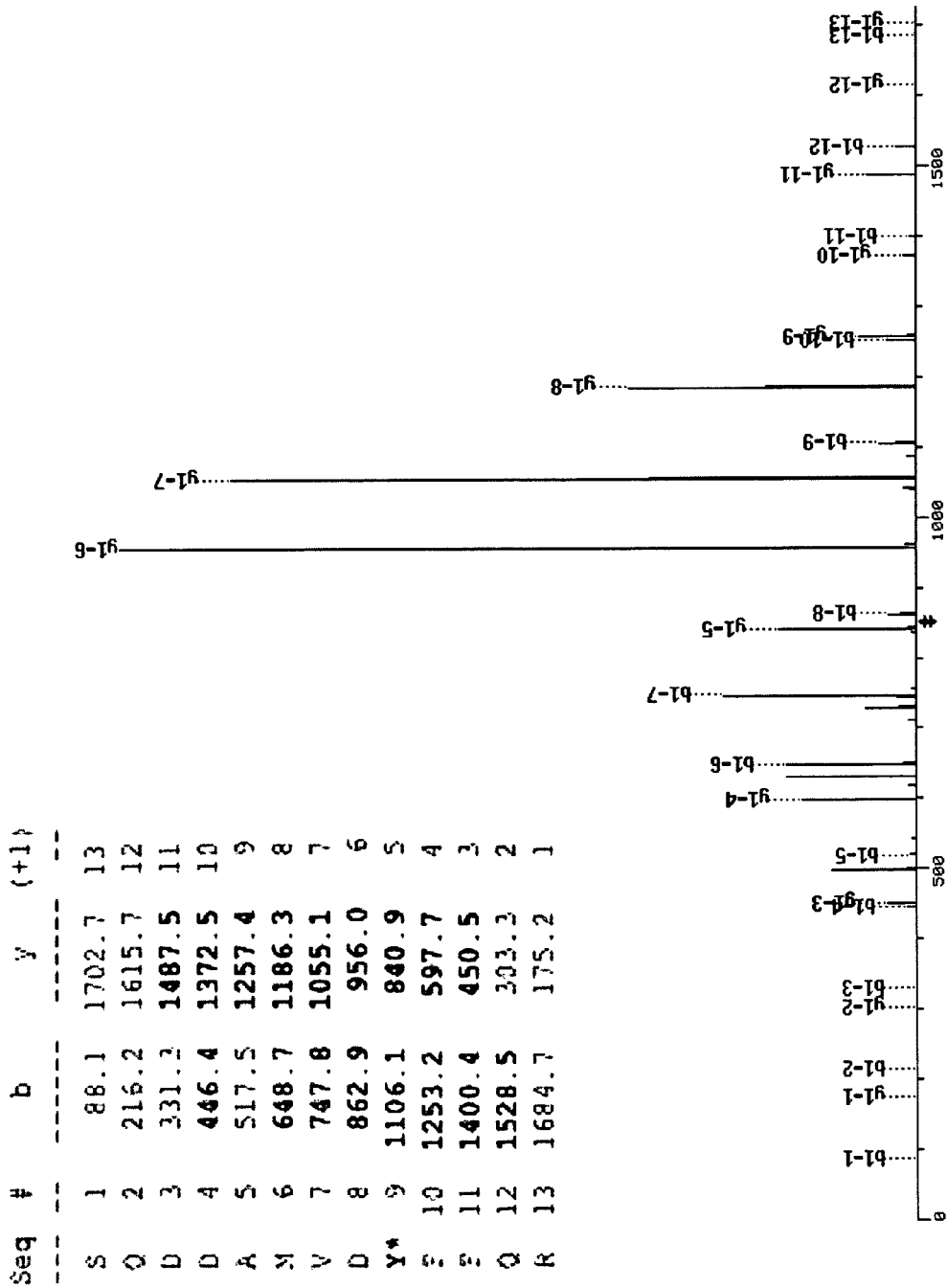
FIG. 5—is an exemplary mass spectrograph depicting the detection of the tyrosine 83 phosphorylation site in PUM1 (see Row 142 in FIG. 2/Table 1), as further described in Example 1 (red and blue indicate ions detected in MS/MS spectrum); Y* indicates the phosphorylated serine (shown as lowercase "y" in FIG. 2).
Figure 6:
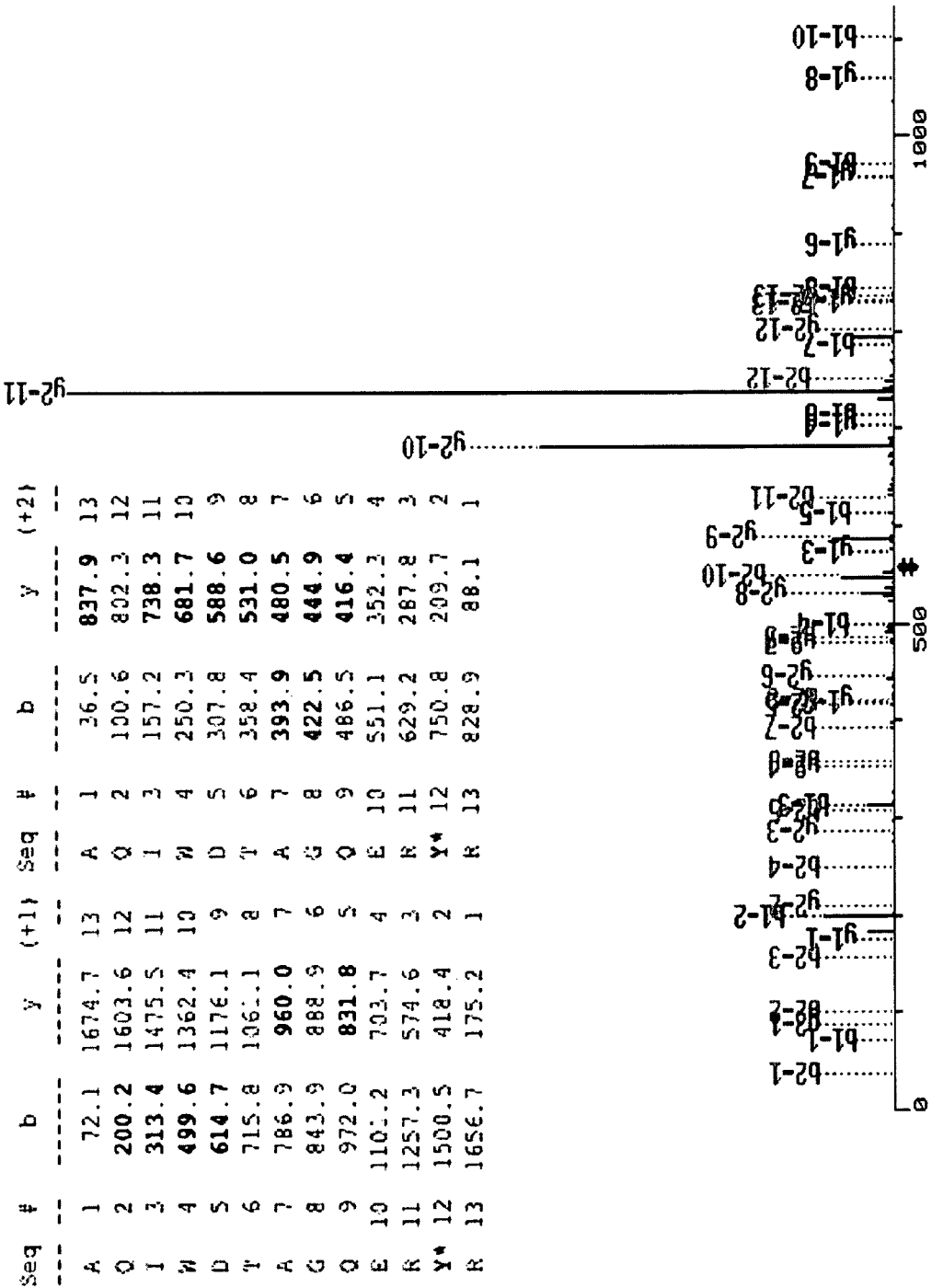
FIG. 6—is an exemplary mass spectrograph depicting the detection of the tyrosine 73 phosphorylation site in RAB11B (see Row 94 in FIG. 2/Table 1), as further described in Example 1 (red and blue indicate ions detected in MS/MS spectrum); Y* indicates the phosphorylated tyrosine (shown as lowercase "y" in FIG. 2).
Figure 7A:
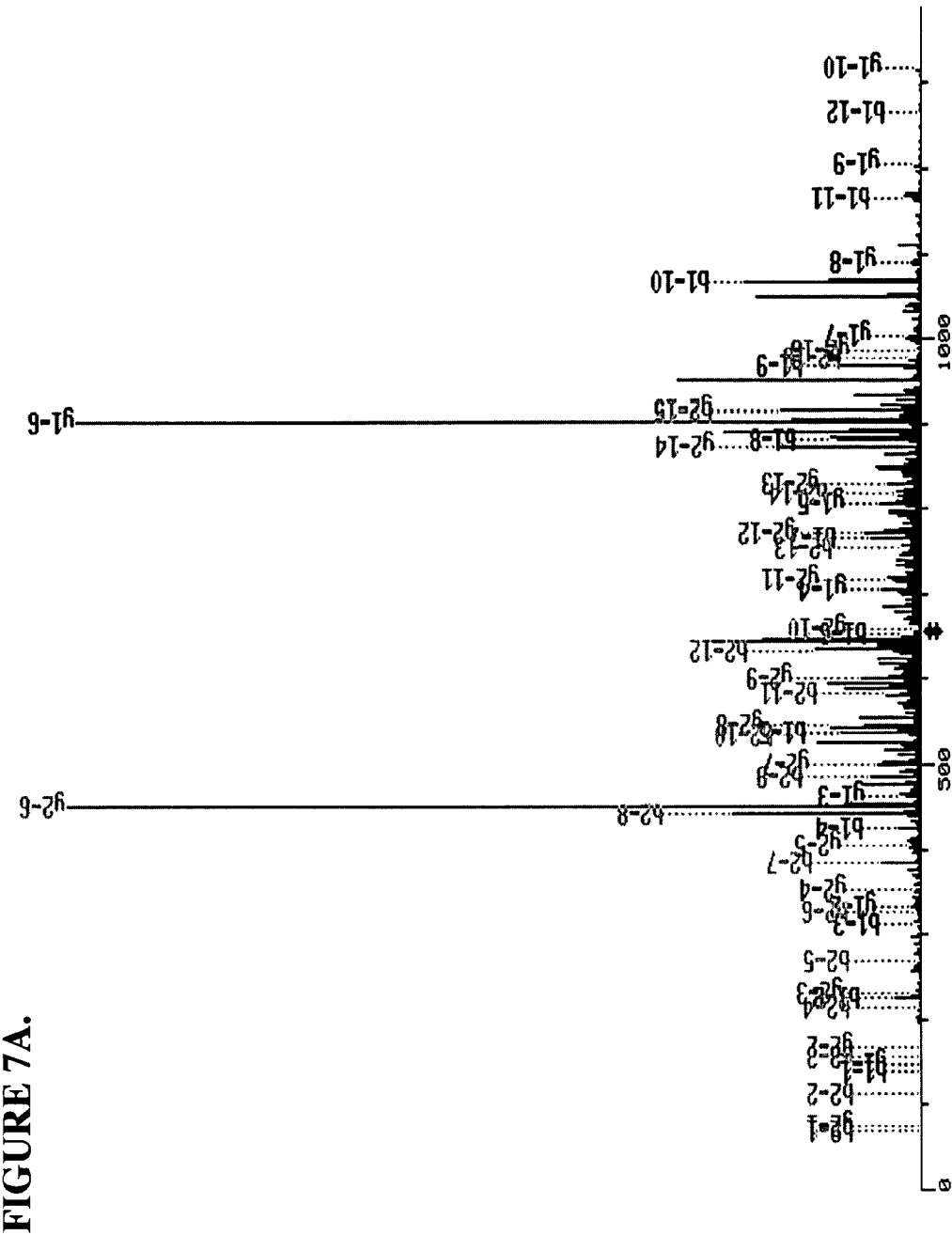
Figure 8:
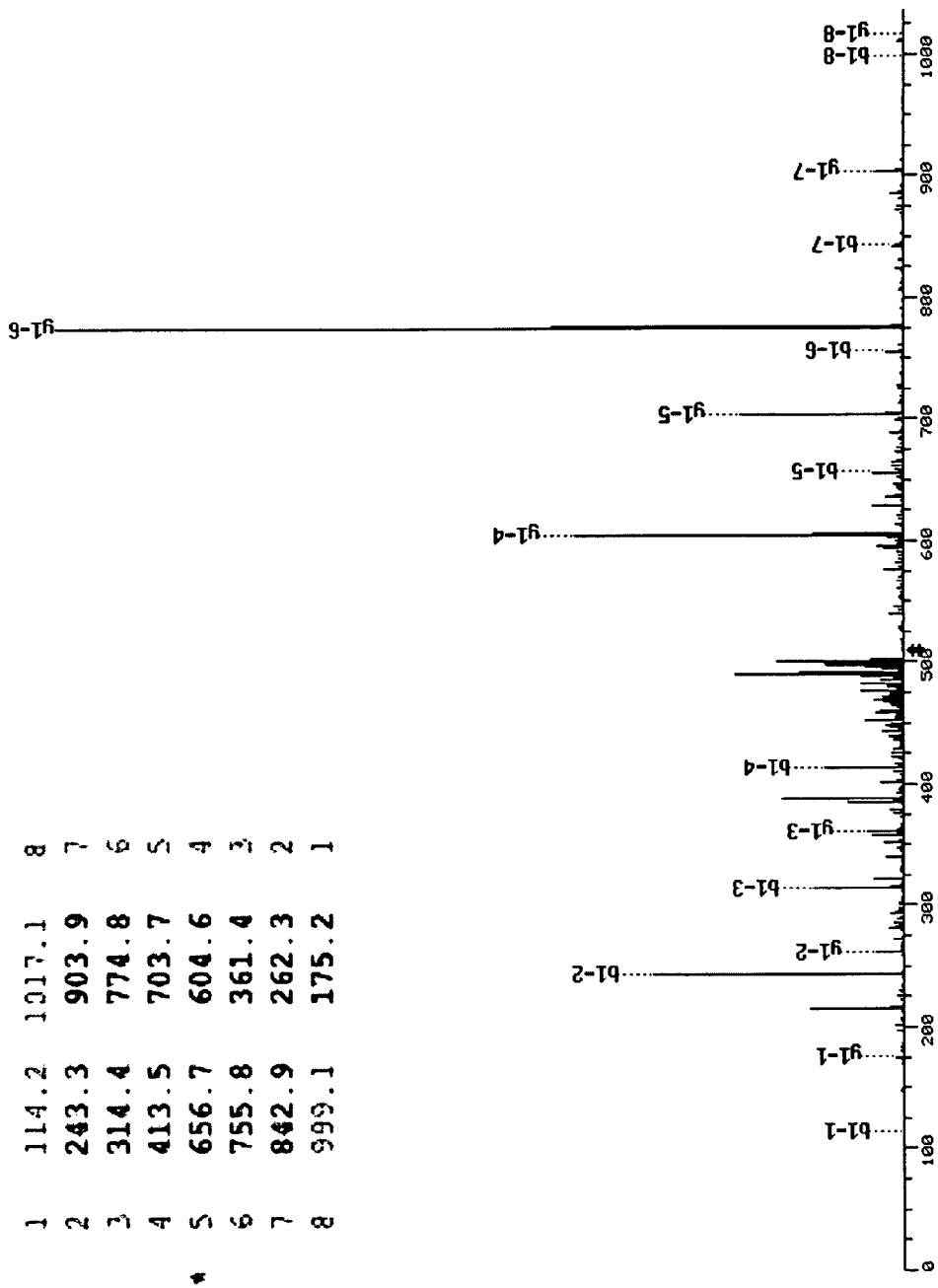
FIG. 8—is an exemplary mass spectrograph depicting the detection of the tyrosine 251 phosphorylation site in RBM15 (see Row 203 in FIG. 2/Table 1), as further described in Example 1 (red and blue indicate ions detected in MS/MS spectrum); Y* indicates the phosphorylated tyrosine (shown as lowercase "y" in FIG. 2).

In accordance with the present invention, nearly 288 novel protein phosphorylation sites in signaling proteins and pathways underlying human Leukemia have now been discovered. These newly described phosphorylation sites were identified by employing the techniques described in "Immunoaffinity Isolation of Modified Peptides From Complex Mixtures," U.S. Patent Publication No. 20030044848, Rush et al., using cellular extracts from a variety of leukemia-derived cell lines, e.g. SEM, K562, etc., as further described below. The novel phosphorylation sites (tyrosine), and their corresponding parent proteins, disclosed herein are listed in Table 1. These phosphorylation sites correspond to numerous different parent proteins (the full sequences (human) of which are all publicly available in SwissProt database and their Accession numbers listed in Column B of Table 1/FIG. 2), each of which fall into discrete protein type groups, for example Acetyltransferases, oxyreductases, adaptor/scaffold proteins, cytoskeletal proteins, protein kinases, and adhesion proteins, etc. (see Column C of Table 1), the phosphorylation of which is relevant to signal transduction activity underlying Leukemias (AML, CML, CLL, and ALL), as disclosed herein.

The discovery of the nearly 288 novel protein phosphorylation sites described herein enables the production, by standard methods, of new reagents, such as phosphorylation site-specific antibodies and AQUA peptides (heavy-isotope labeled peptides), capable of specifically detecting and/or quantifying these phosphorylated sites/proteins. Such reagents are highly useful, inter alia, for studying signal transduction events underlying the progression of Leukemia. Accordingly, the invention provides novel reagents—phospho-specific antibodies and AQUA peptides—for the specific detection and/or quantification of a Leukemia-related signaling protein/polypeptide only when phosphorylated (or only when not phosphorylated) at a particular phosphorylation site disclosed herein. The invention also provides methods of detecting and/or quantifying one or more phosphorylated Leukemia-related signaling proteins using the phosphorylation-site specific antibodies and AQUA peptides of the invention, and methods of obtaining a phosphorylation profile of such proteins (e.g. Kinases).

In part, the invention provides an isolated phosphorylation site-specific antibody that specifically binds a given Leukemia-related signaling protein only when phosphorylated (or not phosphorylated, respectively) at a particular tyrosine enumerated in Column D of Table 1/FIG. 2 comprised within the phosphorylatable peptide site sequence enumerated in corresponding Column E. In further part, the invention provides a heavy-isotope labeled peptide (AQUA peptide) for the detection and quantification of a given Leukemia-related signaling protein, the labeled peptide comprising a particular phosphorylatable peptide site/sequence enumerated in Column E of Table 1/FIG. 2 herein. For example, among the reagents provided by the invention is an isolated phosphorylation site-specific antibody that specifically binds the PUM1 phosphatase only when phosphorylated (or only when not phosphorylated) at tyrosine 83 (see Row 142 (and Columns D and E) of Table 1/FIG. 2). By way of further example, among the group of reagents provided by the invention is an AQUA peptide for the quantification of phosphorylated TRPM3 channel protein, the AQUA peptide comprising the phosphorylatable peptide sequence listed in Column E, Row 48, of Table 1/FIG. 2 (which encompasses the phosphorylatable tyrosine at position 712).

In one embodiment, the invention provides an isolated phosphorylation site-specific antibody that specifically binds a human Leukemia-related signaling protein selected from Column A of Table 1 (Rows 2-289) only when phosphorylated at the tyrosine residue listed in corresponding Column D of Table 1, comprised within the phosphorylatable peptide sequence listed in corresponding Column E of Table 1 (SEQ ID NOs: 1-3, 6-28, 30-42, 44-93, 95-168, 170-183, 185-203, 205-278, and 280-288), wherein said antibody does not bind said signaling protein when not phosphorylated at said tyrosine. In another embodiment, the invention provides an isolated phosphorylation site-specific antibody that specifically binds a Leukemia-related signaling protein selected from Column A of Table 1 only when not phosphorylated at the tyrosine residue listed in corresponding Column D of Table 1, comprised within the peptide sequence listed in corresponding Column E of Table 1 (SEQ ID NOs: 1-3, 6-28, 30-42, 44-93, 95-168, 170-183, 185-203, 205-278, and 280-288), wherein said antibody does not bind said signaling protein when phosphorylated at said tyrosine. Such reagents enable the specific detection of phosphorylation (or non-phosphorylation) of a novel phosphorylatable site disclosed herein. The invention further provides immortalized cell lines producing such antibodies. In one preferred embodiment, the immortalized cell line is a rabbit or mouse hybridoma.

In another embodiment, the invention provides a heavy-isotope labeled peptide (AQUA peptide) for the quantification of a Leukemia-related signaling protein selected from Column A of Table 1, said labeled peptide comprising the phosphorylatable peptide sequence listed in corresponding Column E of Table 1 (SEQ ID NOs: 1-3, 6-28, 30-42, 44-93, 95-168, 170-183, 185-203, 205-278, and 280-288), which sequence comprises the phosphorylatable tyrosine listed in corresponding Column D of Table 1. In certain preferred embodiments, the phosphorylatable tyrosine within the labeled peptide is phosphorylated, while in other preferred embodiments, the phosphorylatable residue within the labeled peptide is not phosphorylated.

Reagents (antibodies and AQUA peptides) provided by the invention may conveniently be grouped by the type of Leukemia-related signaling protein in which a given phosphorylation site (for which reagents are provided) occurs. The protein types for each respective protein (in which a phosphorylation site has been discovered) are provided in Column C of Table 1/FIG. 2, and include: adaptor/scaffold proteins, acetyltransferases, actin binding proteins, adhesion proteins, apoptosis proteins, calcium channel proteins, cell cycle regulation proteins, cell surface proteins, channel proteins, chaperone proteins, contractile proteins, cytokine proteins, chaperone proteins, cytoskeletal proteins, DNA binding proteins, endoplasmic reticulum proteins, cellular metabolism enzymes, G protein regulators and GTPase activating proteins, guanine nucleotide exchange factors, helicase proteins, hydrolases, isomerases immunoglobulin superfamily proteins, inhibitor proteins, kinases, ligases, lyases, methyltransferases, motor proteins, mitochondrial proteins, myosin binding proteins, oxidoreductases, phosphotases, phosphodiesterases, proteases, receptor proteins, RNA binding proteins, transcription proteins, secreted proteins transferases, translation/transporter proteins, ubiquitin conjugating system proteins and vesicle proteins. Each of these distinct protein groups is considered a preferred subset of Leukemia-related signal transduction protein phosphorylation sites disclosed herein, and reagents for their detection/ quantification may be considered a preferred subset of reagents provided by the invention.

Particularly preferred subsets of the phosphorylation sites (and their corresponding proteins) disclosed herein are those occurring on the following protein types/groups listed in Column C of Table 1/FIG. 2, are the protein kinases, adaptor/scaffold proteins, adhesion proteins, enzymes cell cycle regulation proteins, cell surface proteins, transcription proteins, phosphatases, proteases, receptor proteins, RNA binding proteins, G protein regulators/GTPase activators/Guanine nucleotide exchange factors, transporter proteins and ubiquitan conjugating system proteins. Accordingly, among preferred subsets of reagents provided by the invention are isolated antibodies and AQUA peptides useful for the detection and/or quantification of the foregoing preferred protein/phosphorylation site subsets.

In one subset of preferred embodiments, there is provided:
(i) An isolated phosphorylation site-specific antibody that specifically binds a protein kinase selected from Column A, Rows 118-120, of Table 1 only when phosphorylated at the tyrosine listed in corresponding Column D, Rows 118-120, of Table 1, comprised within the phosphorylatable peptide sequence listed in corresponding Column E, Rows 118-120, of Table 1 (SEQ ID NOs: 117-119), wherein said antibody does not bind said protein when not phosphorylated at said tyrosine.
(ii) An equivalent antibody to (i) above that only binds the protein kinase when not phosphorylated at the disclosed site (and does not bind the protein when it is phosphorylated at the site).
(iii) A heavy-isotope labeled peptide (AQUA peptide) for the quantification of a protein kinase selected from Column A, Rows 118-120, said labeled peptide comprising the phosphorylatable peptide sequence listed in corresponding Column E, Rows 118-120, of Table 1 (SEQ ID NOs: 117-119), which sequence comprises the phosphorylatable tyrosine listed in corresponding Column D, Rows 118-120, of Table 1.

In a second subset of preferred embodiments there is provided:
(i) An isolated phosphorylation site-specific antibody that specifically binds an adaptor/scaffold protein selected from Column A, Rows 8-22, of Table 1 only when phosphorylated at the tyrosine listed in corresponding Column D, Rows 8-22, of Table 1, comprised within the phosphorylatable peptide sequence listed in corresponding Column E, Rows 8-22, of Table 1 (SEQ ID NOs: 7-21), wherein said antibody does not bind said protein when not phosphorylated at said tyrosine.
(ii) An equivalent antibody to (i) above that only binds the adaptor/scaffold protein when not phosphorylated at the disclosed site (and does not bind the protein when it is phosphorylated at the site).
(iii) A heavy-isotope labeled peptide (AQUA peptide) for the quantification of a Leukemia-related signaling protein that is a adaptor/scaffold protein selected from Column A, Rows 8-22, said labeled peptide comprising the phosphorylatable peptide sequence listed in corresponding Column E, Rows 8-22, of Table 1 (SEQ ID NOs: 7-21), which sequence comprises the phosphorylatable tyrosine listed in corresponding Column D, Rows 8-22, of Table 1.

Among this preferred subset of reagents, antibodies and AQUA peptides for the detection/quantification of the following adaptor/scaffold protein phosphorylation sites are particularly preferred: BANK1 (Y630), LAX1 (Y373), and PIK3AP1 (Y163) (see SEQ ID NOs: 9, 14 and 18).

In another subset of preferred embodiments there is provided:
(i) An isolated phosphorylation site-specific antibody that specifically binds an adhesion protein selected from Column A, Rows 23-37, of Table 1 only when phosphorylated at the tyrosine listed in corresponding Column D, Rows 23-37, of Table 1, comprised within the phosphorylatable peptide sequence listed in corresponding Column E, Rows 23-37, of Table 1 (SEQ ID NOs: 22-28, and 30-36), wherein said antibody does not bind said protein when not phosphorylated at said tyrosine.
(ii) An equivalent antibody to (i) above that only binds the adhesion protein when not phosphorylated at the disclosed site (and does not bind the protein when it is phosphorylated at the site).
(iii) A heavy-isotope labeled peptide (AQUA peptide) for the quantification of a Leukemia-related signaling protein that is an adhesion protein selected from Column A, Rows 23-37, said labeled peptide comprising the phosphorylatable peptide sequence listed in corresponding Column E, Rows 23-37, of Table 1 (SEQ ID NOs: 22-28, and 30-36), which sequence comprises the phosphorylatable tyrosine listed in corresponding Column D, Rows 23-37, of Table 1.

Among this preferred subset of reagents, antibodies and AQUA peptides for the detection/quantification of the following adhesion protein phosphorylation sites are particularly preferred: FAT (Y400) (see SEQ ID NO: 22).

In still another subset of preferred embodiments there is provided:
(i) An isolated phosphorylation site-specific antibody that specifically binds an enzyme protein selected from Column A, Rows 68-90, of Table 1 only when phosphorylated at the tyrosine listed in corresponding Column D, Rows 68-90, of Table 1, comprised within the phosphorylatable peptide sequence listed in corresponding Column E, Rows 68-90, of Table 1 (SEQ ID NOs: 67-89), wherein said antibody does not bind said protein when not phosphorylated at said tyrosine.
(ii) An equivalent antibody to (i) above that only binds the enzyme protein when not phosphorylated at the disclosed site (and does not bind the protein when it is phosphorylated at the site).
(iii) A heavy-isotope labeled peptide (AQUA peptide) for the quantification of a Leukemia-related signaling protein that is a enzyme protein selected from Column A, Rows 68-90, said labeled peptide comprising the phosphorylatable peptide sequence listed in corresponding Column E, Rows 68-90, of Table 1 (SEQ ID NOs: 67-89), which sequence comprises the phosphorylatable tyrosine listed in corresponding Column D, Rows 68-90, of Table 1.

Among this preferred subset of reagents, antibodies and AQUA peptides for the detection/quantification of the following enzyme protein phosphorylation sites are particularly preferred: ACACA (Y306), FASN (Y289), GLA (Y329), MOGAT2 (Y154) (see SEQ ID NOs: 71, 78, 84 and 85).

In still another subset of preferred embodiments there is provided:
(i) An isolated phosphorylation site-specific antibody that specifically binds a G protein/GTPase activating protein/Guanine nucleotide exchange factor selected from Column A, Rows 92-105, of Table 1 only when phosphorylated at the tyrosine listed in corresponding Column D, Rows 92-105, of Table 1, comprised within the phosphorylatable peptide sequence listed in corresponding Column E, Rows 92-105, of Table 1 (SEQ ID NOs: 91-93, and 95-104), wherein said antibody does not bind said protein when not phosphorylated at said tyrosine.

(ii) An equivalent antibody to (i) above that only binds the G protein/GTPase activating protein/Guanine nucleotide exchange factor when not phosphorylated at the disclosed site (and does not bind the protein when it is phosphorylated at the site).

(iii) A heavy-isotope labeled peptide (AQUA peptide) for the quantification of a Leukemia-related signaling protein that is a G protein/GTPase activating protein/Guanine nucleotide exchange factor selected from Column A, Rows 92-105, said labeled peptide comprising the phosphorylatable peptide sequence listed in corresponding Column E, Rows 92-105, of Table 1 (SEQ ID NOs: 91-93, and 95-104), which sequence comprises the phosphorylatable tyrosine listed in corresponding Column D, Rows 92-105, of Table 1.

Among this preferred subset of reagents, antibodies and AQUA peptides for the detection/quantification of the following G protein/GTPase activating protein/Guanine nucleotide exchange factor phosphorylation sites are particularly preferred: RAB11B (Y73), RICS (Y1353), RASGRP2 (Y189) (see SEQ ID NOs: 93, 99 and 104).

In still another subset of preferred embodiments there is provided:
(i) An isolated phosphorylation site-specific antibody that specifically binds a phosphatase selected from Column A, Rows 136-142, of Table 1 only when phosphorylated at the tyrosine listed in corresponding Column D, Rows 136-142, of Table 1, comprised within the phosphorylatable peptide sequence listed in corresponding Column E, Rows 136-142 of Table 1 (SEQ ID NOs: 135-141), wherein said antibody does not bind said protein when not phosphorylated at said tyrosine.
(ii) An equivalent antibody to (i) above that only binds phosphatase when not phosphorylated at the disclosed site (and does not bind the protein when it is phosphorylated at the site).
(iii) A heavy-isotope labeled peptide (AQUA peptide) for the quantification of a Leukemia-related signaling protein that is a phosphatase selected from Column A, Rows 136-142, said labeled peptide comprising the phosphorylatable peptide sequence listed in corresponding Column E, Rows 136-142, of Table 1 (SEQ ID NOs: 135-141), which sequence comprises the phosphorylatable tyrosine listed in corresponding Column D, Rows 136-142, of Table 1.

Among this preferred subset of reagents, antibodies and AQUA peptides for the detection/quantification of the following phosphatase phosphorylation sites are particularly preferred: PP2R5B (Y244), PUM1 (Y83) (see SEQ ID NOs: 136-141).

In yet another subset of preferred embodiments, there is provided:
(i) An isolated phosphorylation site-specific antibody that specifically binds a protease selected from Column A, Rows 143-146, of Table 1 only when phosphorylated at the tyrosine listed in corresponding Column D, Rows 143-146, of Table 1, comprised within the phosphorylatable peptide sequence listed in corresponding Column E, Rows 143-146, of Table 1 (SEQ ID NOs: 142-145), wherein said antibody does not bind said protein when not phosphorylated at said tyrosine.
(ii) An equivalent antibody to (i) above that only binds the protease when not phosphorylated at the disclosed site (and does not bind the protein when it is phosphorylated at the site).
(iii) A heavy-isotope labeled peptide (AQUA peptide) for the quantification of a Leukemia-related signaling protein that is a protease selected from Column A, Rows 143-146, said labeled peptide comprising the phosphorylatable peptide sequence listed in corresponding Column E, Rows 143-146, of Table 1 (SEQ ID NOs: 142-145), which sequence comprises the phosphorylatable tyrosine listed in corresponding Column D, Rows 143-146, of Table 1.

Among this preferred subset of reagents, antibodies and AQUA peptides for the detection/quantification of the following protease phosphorylation sites are particularly preferred: ADAMTS14 (Y38) and SNEP2 (Y239) (see SEQ ID NOs: 142 and 143).

In yet another subset of preferred embodiments, there is provided:
(i) An isolated phosphorylation site-specific antibody specifically binds a receptor protein selected from Column A, Rows 149-170, of Table 1 only when phosphorylated at the tyrosine listed in corresponding Column D, Rows 149-170, of Table 1, comprised within the phosphorylatable peptide sequence listed in corresponding Column E, Rows 149-170, of Table 1 (SEQ ID NOs: 148-168), wherein said antibody does not bind said protein when not phosphorylated at said tyrosine.
(ii) An equivalent antibody to (i) above that only binds the receptor protein when not phosphorylated at the disclosed site (and does not bind the protein when it is phosphorylated at the site).
(iii) A heavy-isotope labeled peptide (AQUA peptide) for the quantification of a Leukemia-related signaling protein that is a receptor protein selected from Column A, Rows 149-170, said labeled peptide comprising the phosphorylatable peptide sequence listed in corresponding Column E, Rows 149-170, of Table 1 (SEQ ID NOs: 148-168), which sequence comprises the phosphorylatable tyrosine listed in corresponding Column D, Rows 149-170, of Table 1.

Among this preferred subset of reagents, antibodies and AQUA peptides for the detection/quantification of the following receptor protein phosphorylation sites are particularly preferred: ROBO1 (Y328) (see SEQ ID NOs: 166).

In yet another subset of preferred embodiments, there is provided:
(i) An isolated phosphorylation site-specific antibody that specifically binds a RNA binding protein selected from Column A, Rows 171-226, of Table 1 only when phosphorylated at the tyrosine listed in corresponding Column D, Rows 171-226, of Table 1, comprised within the phosphorylatable peptide sequence listed in corresponding Column E, Rows 171-226, of Table 1 (SEQ ID NOs: 170-183, 185-203, and 205-225), wherein said antibody does not bind said protein when not phosphorylated at said tyrosine.
(ii) An equivalent antibody to (i) above that only binds the RNA binding protein when not phosphorylated at the disclosed site (and does not bind the protein when it is phosphorylated at the site).
(iii) A heavy-isotope labeled peptide (AQUA peptide) for the quantification of a Leukemia-related signaling protein that is a RNA binding protein selected from Column A, Rows 171-226, said labeled peptide comprising the phosphorylatable peptide sequence listed in corresponding Column E, Rows 171-226, of Table 1 (SEQ ID NOs: 170-183, 185-203, and 205-225), which sequence comprises the phosphorylatable tyrosine listed in corresponding Column D, Rows 171-226, of Table 1.

Among this preferred subset of reagents, antibodies and AQUA peptides for the detection/quantification of the following RNA binding protein phosphorylation sites are particularly preferred: ARPP-19 (Y36), KHDRBS1 (Y435), MATR3 (Y243), and RBM15 (Y251) (see SEQ ID NO: 170, 188, 190 and 202).

In still another subset of preferred embodiments, there is provided:

(i) An isolated phosphorylation site-specific antibody that specifically binds a transcription protein selected from Column A, Rows 230-247, of Table 1 only when phosphorylated at the tyrosine listed in corresponding Column D, Rows 230-247, of Table 1, comprised within the phosphorylatable peptide sequence listed in corresponding Column E, Rows 230-247, of Table 1 (SEQ ID NOs: 229-246), wherein said antibody does not bind said protein when not phosphorylated at said tyrosine.

(ii) An equivalent antibody to (i) above that only binds the transcription protein when not phosphorylated at the disclosed site (and does not bind the protein when it is phosphorylated at the site).

(iii) A heavy-isotope labeled peptide (AQUA peptide) for the quantification of a Leukemia-related signaling protein that transcription protein selected from Column A, Rows 230-247, said labeled peptide comprising the phosphorylatable peptide sequence listed in corresponding Column E, Rows 230-247, of Table 1 (SEQ ID NOs: 229-246), which sequence comprises the phosphorylatable tyrosine listed in corresponding Column D, Rows 230-247, of Table 1.

Among this preferred subset of reagents, antibodies and AQUA peptides for the detection/quantification of the following transcription protein phosphorylation sites are particularly preferred: FOXJ1 (Y157) and IRFBP1 (Y268) (see SEQ ID NOs: 238 and 239).

In still another subset of preferred embodiments, there is provided:

(i) An isolated phosphorylation site-specific antibody that specifically binds a transporter protein selected from Column A, Rows 252-260, of Table 1 only when phosphorylated at the tyrosine listed in corresponding Column D, Rows 252-260, of Table 1, comprised within the phosphorylatable peptide sequence listed in corresponding Column E, Rows 252-260, of Table 1 (SEQ ID NOs: 251-259), wherein said antibody does not bind said protein when not phosphorylated at said tyrosine.

(ii) An equivalent antibody to (i) above that only binds the transporter protein when not phosphorylated at the disclosed site (and does not bind the protein when it is phosphorylated at the site).

(iii) A heavy-isotope labeled peptide (AQUA peptide) for the quantification of a Leukemia-related signaling protein that is an transporter protein selected from Column A, Rows 252-260, said labeled peptide comprising the phosphorylatable peptide sequence listed in corresponding Column E, Rows 252-260, of Table 1 (SEQ ID NOs: 251-259), which sequence comprises the phosphorylatable tyrosine listed in corresponding Column D, Rows 252-260, of Table 1.

In still another subset of preferred embodiments, there is provided:

(i) An isolated phosphorylation site-specific antibody that specifically binds an ubiquitin conjugating pathway protein selected from Column A, Rows 261-274, of Table 1 only when phosphorylated at the tyrosine listed in corresponding Column D, Rows 261-274, of Table 1, comprised within the phosphorylatable peptide sequence listed in corresponding Column E, Rows 261-274, of Table 1 (SEQ ID NOs: 260-273), wherein said antibody does not bind said protein when not phosphorylated at said tyrosine.

(ii) An equivalent antibody to (i) above that only binds the ubiquitin conjugating pathway protein when not phosphorylated at the disclosed site (and does not bind the protein when it is phosphorylated at the site).

(iii) A heavy-isotope labeled peptide (AQUA peptide) for the quantification of a Leukemia-related signaling protein that is an an ubiquitin conjugating pathway protein selected from Column A, Rows 261-274, said labeled peptide comprising the phosphorylatable peptide sequence listed in corresponding Column E, Rows 261-274, of Table 1 (SEQ ID NOs: 260-273), which sequence comprises the phosphorylatable tyrosine listed in corresponding Column D, Rows 261-274, of Table 1.

Among this preferred subset of reagents, antibodies and AQUA peptides for the detection/quantification of the following an ubiquitin conjugating pathway protein phosphorylation sites are particularly preferred: UBE3B (Y695) and CUL7 (Y786) (see SEQ ID NO: 261 and 270).

In yet a further subset of preferred embodiments, there is provided:

(i) An isolated phosphorylation site-specific antibody that specifically binds a protein selected from the group consisting of BIRC4BP (Y261), TRPM3 (Y712), C17orf31 (Y52), HIST1H2BO (Y43), TRAPPC1 (Y39), SUFU (Y60), AVO3 (Y1269), PARP3 (Y420), SCAMP3 (Y41) and SNAP23 (Y139) (Column A, Rows 38, 48, 58, 61, 67, 116, 147, 250, 280 and 281 of Table 1) only when phosphorylated at the tyrosine listed in corresponding Column D, Rows 38, 48, 58, 61, 67, 116, 147, 250, 280 and 281 of Table 1), said tyrosine comprised within the phosphorylatable peptide sequence listed in corresponding Column E, Rows 38, 48, 58, 61, 67, 116, 147, 250, 280 and 281 of Table 1 (SEQ ID NOs: 37, 47, 57, 60, 66, 115, 146, 249, 279 and 280), wherein said antibody does not bind said protein when not phosphorylated at said tyrosine.

(ii) An equivalent antibody to (i) above that only binds the of BIRC4BP (Y261), TRPM3 (Y712), C17orf31 (Y52), HIST1H2BO (Y43), TRAPPC1 (Y39), SUFU (Y60), AVO3 (Y1269), PARP3 (Y420), SCAMP3 (Y41) and SNAP23 (Y139) protein when not phosphorylated at the disclosed site (and does not bind the protein when it is phosphorylated at the site).

(iii) A heavy-isotope labeled peptide (AQUA peptide) for the quantification of a protein selected from the group consisting of BIRC4BP (Y261), TRPM3 (Y712), C17orf31 (Y52), HIST1H2BO (Y43), TRAPPC1 (Y39), SUFU (Y60), AVO3 (Y1269), PARP3 (Y420), SCAMP3 (Y41) and SNAP23 (Y139) (Column A, Rows 38, 48, 58, 61, 67, 116, 147, 250, 280 and 281 of Table 1), said labeled peptide comprising the phosphorylatable peptide sequence listed in corresponding Column E, Rows 38, 48, 58, 61, 67, 116, 147, 250, 280 and 281, of Table 1 (SEQ ID NOs: 37, 47, 57, 60, 66, 115, 146, 249, 279 and 280), which sequence comprises the phosphorylatable tyrosine listed in corresponding Column D, Rows 38, 48, 58, 61, 67, 116, 147, 250, 280 and 281 of Table 1.

The invention also provides, in part, an immortalized cell line producing an antibody of the invention, for example, a cell line producing an antibody within any of the foregoing preferred subsets of antibodies. In one preferred embodiment, the immortalized cell line is a rabbit hybridoma or a mouse hybridoma.

In certain other preferred embodiments, a heavy-isotope labeled peptide (AQUA peptide) of the invention (for example, an AQUA peptide within any of the foregoing preferred subsets of AQUA peptides) comprises a disclosed site sequence wherein the phosphorylatable tyrosine is phosphorylated. In certain other preferred embodiments, a heavy-isotope labeled peptide of the invention comprises a disclosed site sequence wherein the phosphorylatable tyrosine is not phosphorylated.

The foregoing subsets of preferred reagents of the invention should not be construed as limiting the scope of the invention, which, as noted above, includes reagents for the detection and/or quantification of disclosed phosphorylation sites on any of the other protein type/group subsets (each a preferred subset) listed in Column C of Table 1/FIG. 2.

Also provided by the invention are methods for detecting or quantifying a Leukemia-related signaling protein that is tyrosine phosphorylated, said method comprising the step of utilizing one or more of the above-described reagents of the invention to detect or quantify one or more Leukemia-related signaling protein(s) selected from Column A of Table 1 only when phosphorylated at the tyrosine listed in corresponding Column D of Table 1. In certain preferred embodiments of the methods of the invention, the reagents comprise a subset of preferred reagents as described above.

Also provided by the invention is a method for obtaining a phosphorylation profile of protein kinases that are phosphorylated in Leukemia signaling pathways, said method comprising the step of utilizing one or more isolated antibody that specifically binds a protein inase selected from Column A, Rows 210-291, of Table 1 only when phosphorylated at the tyrosine listed in corresponding Column D, Rows 210-291, of Table 1, comprised within the phosphorylation site sequence listed in corresponding Column E, Rows 210-291, of Table 1 (SEQ ID NOs: SEQ ID NOs: 210-221, 223-280, and 281-290), to detect the phosphorylation of one or more of said protein kinases, thereby obtaining a phosphorylation profile for said kinases.

The identification of the disclosed novel Leukemia-related signaling protein phosphorylation sites, and the standard production and use of the reagents provided by the invention are described in further detail below and in the Examples that follow.

All cited references are hereby incorporated herein, in their entirety, by reference. The Examples are provided to further illustrate the invention, and do not in any way limit its scope, except as provided in the claims appended hereto.

TABLE 1

Newly Discovered Leukemia-related Phosphorylation Sites.

| A<br>Protein<br>1 Name | B<br>Accession<br>No. | C<br>Protein Type | D<br>Phospho-<br>Residue | E<br>Phosphorylation<br>Site Sequence | H<br>SEQ ID NO |
|---|---|---|---|---|---|
| 2 CAS1 | NP_075051.3 | Acetyltransferase | Y184 | IHNGSSEALSQyKMNITSIAPLLEK | SEQ ID NO: 1 |
| 3 CPT1B | NP_004368.1 | Acetyltransferase | Y644 | NMyRLAMTGAGIDRHLFC | SEQ ID NO: 2 |
| 4 FLJ10774 | NP_078938.1 | Acetyltransferase | Y820 | EELEALFLPyDLK | SEQ ID NO: 3 |
| 5 Pstpip2 | | Actin binding protein | Y323 | RIPDDPDySVVEDYSLLYQ | SEQ ID NO: 4 |
| 6 Pstpip2 | | Actin binding protein | Y333 | RIPDDPDYSVVEDYSLLyQ | SEQ ID NO: 5 |
| 7 SHRM | NP_065910.2 | Actin binding protein | Y1833 | PNEFDKyRMFIGDLDK | SEQ ID NO: 6 |
| 8 AP4E1 | NP_031373.2 | Adaptor/scaffold | Y830 | DDyYSNTLHDTGDKE | SEQ ID NO: 7 |
| 9 AP4E1 | NP_031373.2 | Adaptor/scaffold | Y831 | DDYySNTLHDTGDKE | SEQ ID NO: 8 |
| 10 BANK1 | NP_060405.2 | Adaptor/scaffold | Y630 | PTSIPPKEETTPyIAQVFQQK | SEQ ID NO: 9 |
| 11 FCRL2 | NP_110391.2 | Adaptor/scaffold | Y502 | TLLENKDSQVIySSVK | SEQ ID NO: 10 |
| 12 FCRL3 | NP_443171.2 | Adaptor/scaffold | Y722 | GRAHEEDDEENyENVPR | SEQ ID NO: 11 |
| 13 FGF14 | NP_004106.1 | Adaptor/scaffold | Y81 | QGyYLQMHPDGALDGTKDDSTNSTLFNLIPVGLR | SEQ ID NO: 12 |
| 14 FGF14 | NP_004106.1 | Adaptor/scaffold | Y82 | QGYyLQMHPDGALDGTKDDSTNSTLFNLIPVGLR | SEQ ID NO: 13 |
| 15 LAX1 | NP_060243.2 | Adaptor/scaffold | Y373 | HREEMSNEDSSDyENVLTAK | SEQ ID NO: 14 |
| 16 LRRFIP2 | NP_006300.1 | Adaptor/scaffold | Y304 | SDKQYAENyTRPSSR | SEQ ID NO: 15 |
| 17 LRRFIP2 | NP_006300.1 | Adaptor/scaffold | Y348 | DIyDLKDQIQDVEGR | SEQ ID NO: 16 |
| 18 MAP3K7IP2 | NP_055908.1 | Adaptor/scaffold | Y632 | GPHFNPSAIHNFyDNIGFVGPVPPKPK | SEQ ID NO: 17 |
| 19 PIK3AP1 | NP_689522.2 | Adaptor/scaffold | Y163 | AISEDSGCDSVTDTEPEDEKVVSySK | SEQ ID NO: 18 |
| 20 PRKCABP | NP_036539.1 | Adaptor/scaffold | Y275 | EMDDEEySCIALGEPLYR | SEQ ID NO: 19 |
| 21 PRKCABP | NP_036539.1 | Adaptor/scaffold | Y285 | EMDDEEYSCIALGEPLyR | SEQ ID NO: 20 |
| 22 SPG20 | NP_055902.1 | Adaptor/scaffold | Y45 | GLNTDELGQKEEAKNyYK | SEQ ID NO: 21 |

TABLE 1-continued

Newly Discovered Leukemia-related Phosphorylation Sites.

| A<br>Protein<br>Name | B<br>Accession<br>No. | C<br>Protein Type | D<br>Phospho-<br>Residue | E<br>Phosphorylation<br>Site Sequence | H<br>SEQ ID NO |
|---|---|---|---|---|---|
| 23 FAT | NP_005236.2 | Adhesion | Y400 | DVYRAEISEFAPPNTPVVMVKAIPAYSHLRyVFK | SEQ ID NO: 22 |
| 24 FAT2 | NP_001438.1 | Adhesion | Y2139 | yHLKVIARDGGTPSLQSEEEVLVTVR | SEQ ID NO: 23 |
| 25 ITGBL1 | NP_004782.1 | Adhesion | Y280 | DCRAVyDRYSDDFCSGHGQCNCGR | SEQ ID NO: 24 |
| 26 ITGBL1 | NP_004782.1 | Adhesion | Y283 | DCRAVYDRySDDFCSGHGQCNCGR | SEQ ID NO: 25 |
| 27 NRXN1 | NP_004792.1 | Adhesion | Y1027 | ITTQITAGARNLDLKSDLyIGGVAKETYKSLPK | SEQ ID NO: 26 |
| 28 NRXN1 | NP_004792.1 | Adhesion | Y1036 | ITTQITAGARNLDLKSDLYIGGVAKETyKSLPK | SEQ ID NO: 27 |
| 29 PARVG | NP_071424.1 | Adhesion | Y7 | FLyDLLQLPKGVEPPAEEE | SEQ ID NO: 28 |
| 30 PCDHB5 | | Adhesion | Y191 | DGRKyPELVLDK | SEQ ID NO: 29 |
| 31 PCDHGB6 | NP_061749.1 | Adhesion | Y418 | EQTPEyNVTIVATDRGKPPLSSSR | SEQ ID NO: 30 |
| 32 PVRL1 | NP_976030.1 | Adhesion | Y370 | LLAGTVAVFLILVAVLTVFFLyNR | SEQ ID NO: 31 |
| 33 PVRL2 | NP_002847.1 | Adhesion | Y408 | KSPGGAGGGASGDGGFyDPK | SEQ ID NO: 32 |
| 34 SIGLEC9 | NP_055256.1 | Adhesion | Y456 | GQEATDTEySEIK | SEQ ID NO: 33 |
| 35 TES | NP_056456.1 | Adhesion | Y251 | EGDPAIyAER | SEQ ID NO: 34 |
| 36 VEZATIN | NP_060069.2 | Adhesion | Y514 | KDDFyYLSQEDKERQKREHEESK | SEQ ID NO: 35 |
| 37 VEZATIN | NP_060069.2 | Adhesion | Y515 | KDDFYyLSQEDKERQKREHEESK | SEQ ID NO: 36 |
| 38 BIRC4BP | NP_059993.2 | Apoptosis | Y261 | GDKAAyDILR | SEQ ID NO: 37 |
| 39 PAWR | NP_002574.2 | Apoptosis | Y177 | STGVVNIPAAECLDEyEDDEAGQKER | SEQ ID NO: 38 |
| 40 PAWR | NP_002574.2 | Apoptosis | Y241 | YKSTTSVSEEDVSSRySR | SEQ ID NO: 39 |
| 41 PDCD1 | NP_005009.1 | Apoptosis | 121 | NDSGTyLCGAISLAPKAQIK | SEQ ID NO: 40 |
| 42 SCOTIN | NP_057563.3 | Apoptosis | 232 | PASQPPYNPAyMDAPKAAL | SEQ ID NO: 41 |
| 43 POLS | NP_008930.1 | Cell cycle regulation | 339 | IATCNGEQTQNREPESPyGQR | SEQ ID NO: 42 |
| 44 CD300A | | Cell surface | 267 | EELHyASVVFDSNTNR | SEQ ID NO: 43 |
| 45 CD300A | NP_009192.2 | Cell surface | Y293 | IAAQRPREEEPDSDySVIR | SEQ ID NO: 44 |
| 46 MUC13 | NP_149038.2 | Cell surface | Y500 | DSQMQNPySR | SEQ ID NO: 45 |
| 47 ITPR2 | NP_002214.2 | Channel, calcium | Y2109 | DVGHNIyILAHQLAR | SEQ ID NO: 46 |
| 48 TRPM3 | NP_001007472.1 | Channel, calcium | Y712 | DFGQLAVELLDQSyKQDEQLAMK | SEQ ID NO: 47 |
| 49 C21orf55 | NP_060303.2 | Chaperone | Y31 | SHLIKATVIPNRVKMLPyFGIIRNR | SEQ ID NO: 48 |
| 50 TOMM34 | NP_006800.2 | Chaperone | Y54 | VLQAQGSSDPEEESVLySNR | SEQ ID NO: 49 |
| 51 IL12A | NP_000873.2 | Cytokine | Y162 | KTSFMMALCLSSIyEDLK | SEQ ID NO: 50 |
| 52 CKAP2 | NP_060674.2 | Cytoskeletal protein | Y598 | YNVSTTPyLQSVK | SEQ ID NO: 51 |
| 53 CKAP2 | NP_060674.2 | Cytoskeletal protein | Y676 | ETDAFVCRPNAALCRVyYEADTT | SEQ ID NO: 52 |
| 54 GAS2L2 | NP_644814.1 | Cytoskeletal protein | Y801 | RDHRPEKQPSRIPRPLAyVFLGPARQPPKDR | SEQ ID NO: 53 |
| 55 GAS2L3 | NP_777602.1 | Cytoskeletal protein | Y683 | KKEDDDHyFVMTGSK | SEQ ID NO: 54 |

TABLE 1-continued

Newly Discovered Leukemia-related Phosphorylation Sites.

| A<br>Protein<br>Name | B<br>Accession<br>No. | C<br>Protein Type | D<br>Phospho-<br>Residue | E<br>Phosphorylation<br>Site Sequence | H<br>SEQ ID NO |
|---|---|---|---|---|---|
| 56 HOOK3 | NP_115786.1 | Cytoskeletal protein | Y347 | NTMyMQNTVSLEEELRK | SEQ ID NO: 55 |
| 57 KA35 | NP_998821.2 | Cytoskeletal protein | Y379 | QNQEyEILLDVKSR | SEQ ID NO: 56 |
| 58 C17orf31 | NP_060045.3 | DNA binding protein | Y52 | RPDLEIyKPGLSR | SEQ ID NO: 57 |
| 59 C17orf31 | NP_060045.3 | DNA binding protein | Y508 | FQNSDNPyYYPR | SEQ ID NO: 58 |
| 60 HIST1H2BG | NP_003509.1 | DNA binding protein | Y43 | KESYSVYVyK | SEQ ID NO: 59 |
| 61 HIST1H2BO | NP_003518.2 | DNA binding protein | Y43 | KESYSIYVyK | SEQ ID NO: 60 |
| 62 PCM1 | NP_006188.2 | DNA binding protein | Y1176 | TEyMAFPKPFESSSSIGAEKPR | SEQ ID NO: 61 |
| 63 SMARCE1 | NP_003070.3 | DNA binding protein | Y170 | GEPyMSIQPAEDPDDYDDGFSMK | SEQ ID NO: 62 |
| 64 HNRPU | NP_004492.2 | DNA binding protein; RNA binding protein | Y247 | GYFEYIEENKySR | SEQ ID NO: 63 |
| 65 RTN4 | NP_065393.1 | Endoplasmic reticulum | Y659 | SIKHEPENPPPyEE | SEQ ID NO: 64 |
| 66 RTN4 | NP_065393.1 | Endoplasmic reticulum | Y718 | TKLSAEPAPDFSDySE | SEQ ID NO: 65 |
| 67 TRAPPC1 | NP_067033.1 | Endoplasmic reticulum | Y39 | LMyGMLFSIRSFVSKMSPLDMK | SEQ ID NO: 66 |
| 68 RARS | NP_002878.2 | Enzym, misc. | Y384 | SDGGYTyDTSDLAAIK | SEQ ID NO: 67 |
| 69 ALDH2 | NP_000681.2 | Enzyme, cellular metabolism | Y396 | GyFIQPTVFGDVQDGMTIAK | SEQ ID NO: 68 |
| 70 GLUD1 | NP_005262.1 | Enzyme, cellular metabolism | Y464 | DSNyHLLMSVQESLERK | SEQ ID NO: 69 |
| 71 LDHA | NP_005557.1 | Enzyme, cellular metabolism | Y127 | NVNIFKFIIPNVVKySPNCK | SEQ ID NO: 70 |
| 72 ACACA | AAC50139.1 | Enzyme, cellular metabolism; Transferase | Y306 | GYVKDVDDGLKAAEKVGyPVMIK | SEQ ID NO: 71 |
| 73 AARS | NP_001596.2 | Enzyme, misc. | Y543 | TCFYAEQGGQIyDEGYLVK | SEQ ID NO: 72 |
| 74 ALDOA | NP_000025.1 | Enzyme, misc. | Y3 | PyQYPALTPEQK | SEQ ID NO: 73 |
| 75 BG1 | NP_055977.3 | Enzyme, misc. | Y719 | LTVLEKYKGIIDSFyQEQK | SEQ ID NO: 74 |
| 76 CAD | NP_004332.2 | Enzyme, misc. | Y1890 | KVAEPELMGTPDGTCyPPPPVPR | SEQ ID NO: 75 |
| 77 CSAD | NP_057073.3 | Enzyme, misc. | Y158 | LRALVGWSSGDGIFCPGGSISNMyAVNLAR | SEQ ID NO: 76 |
| 78 FA2H | NP_077282.2 | Enzyme, misc. | Y311 | CMQLILPEAVGGTVFAGGLLGYVLyDMTH | SEQ ID NO: 77 |
| 79 FASN | NP_004095.4 | Enzyme, misc. | Y289 | SLYQSAGVAPESFEyIEAHGTGTK | SEQ ID NO: 78 |
| 80 FASN | AAC50259.1 | Enzyme, misc. | Y2433 | AKySGNVMLLR | SEQ ID NO: 79 |
| 81 FUCA1 | NP_000138.1 | Enzyme, misc. | Y301 | FKPQSLPDHKWEMCTSIDKFSWGyRR | SEQ ID NO: 80 |
| 82 GALE | NP_000394.2 | Enzyme, misc. | Y267 | IyNLGTGTGYSVLQMVQAMEKASGKKIPYK | SEQ ID NO: 81 |

TABLE 1-continued

Newly Discovered Leukemia-related Phosphorylation Sites.

| A Protein Name | B Accession No. | C Protein Type | D Phospho-Residue | E Phosphorylation Site Sequence | H SEQ ID NO |
|---|---|---|---|---|---|
| 83 GALE | NP_000394.2 | Enzyme, misc. | Y275 | IYNLGTGTGySVLQMVQAMEKASGKKIPYK | SEQ ID NO: 82 |
| 84 GLA | NP_000160.1 | Enzyme, misc. | Y134 | LGIyADVGNK | SEQ ID NO: 83 |
| 85 GLA | NP_000160.1 | Enzyme, misc. | Y329 | ALLQDKDVIAINQDPLGKQGyQLRQGDNFEVWER | SEQ ID NO: 84 |
| 86 MOGAT2 | NP_079374.2 | Enzyme, misc. | Y154 | DyIMSAGLVTSEKESAAHILNRK | SEQ ID NO: 85 |
| 87 TARS | NP_689508.3 | Enzyme, misc. | Y298 | IyGISFPDPK | SEQ ID NO: 86 |
| 88 UROC1 | NP_653240.1 | Enzyme, misc. | Y185 | LVITNGMVIPNySSRTEYEK | SEQ ID NO: 87 |
| 89 VARS2 | NP_006286.1 | Enzyme, misc. | Y280 | DPGVITyDLPTPPGEK | SEQ ID NO: 88 |
| 90 WARS | NP_004175.2 | Enzyme, misc. | Y316 | DRTDIQCLIPCAIDQDPyFR | SEQ ID NO: 89 |
| 91 USH2A | NP_996816.1 | Extracelluar matrix | Y3701 | HIIINSTTVELyWSLPEK | SEQ ID NO: 90 |
| 92 SYTL4 | NP_542775.1 | G protein regulator, misc. | Y554 | EAKNLTAAKAGGTSDSFVKGyLLPMRNK | SEQ ID NO: 91 |
| 93 SPG3A | NP_056999.2 | G protein, monomeric (non-Rab) | Y538 | HLyHQAFPTPKSESTEQSEKKK | SEQ ID NO: 92 |
| 94 RAB11B | NP_004209.1 | G protein, Rab | Y73 | AQIWDTAGQERyR | SEQ ID NO: 93 |
| 95 ARFGAP3 | | GTPase activating protein, ARF | Y349 | KKYNDDSDDSyFTSSSR | SEQ ID NO: 94 |
| 96 GPSM1 | NP_056412.2 | GTPase activating protein, misc. | Y376 | LTSPAASEKPDLAGyEAQGARPK | SEQ ID NO: 95 |
| 97 TBC1D15 | NP_073608.2 | GTPase activating protein, misc. | Y215 | NCQNKSLSQSFENLLDEPAyGLIQAG | SEQ ID NO: 96 |
| 98 DLC1 | NP_006085.2 | GTPase activating protein, Rac/Rho | Y919 | EKFKGWVSYSTSEQAELSyK | SEQ ID NO: 97 |
| 99 RICS | NP_055530.2 | GTPase activating protein, Rac/Rho | Y1283 | SDyHVTQLQPYFENGR | SEQ ID NO: 98 |
| 100 RICS | NP_055530.2 | GTPase activating protein, Rac/Rho | Y1353 | SLySYAGLAPRPR | SEQ ID NO: 99 |
| 101 RICS | NP_055530.2 | GTPase activating protein, Rac/Rho | Y1369 | ANVTGyFSPNDHNVVSMPPMDVK | SEQ ID NO: 100 |
| 102 DOCK8 | NP_982272.1 | Guanine nucleotide exchange factor, misc. | Y869 | MSyYCSGSSDAPSSPMPRPASK | SEQ ID NO: 101 |
| 103 ARHGEF18 | NP_056133.2 | Guanine nucleotide exchange factor, Rac/Rho | Y845 | VSMLPSGVGPEyAERPEVAR | SEQ ID NO: 102 |
| 104 MCF2L2 | NP_055893.2 | Guanine nucleotide exchange factor, Rac/Rho | Y751 | yLKGPSQRLIK | SEQ ID NO: 103 |
| 105 RASGRP2 | NP_005816.2 | Guanine nucleotide exchange factor, Ras | Y189 | HSSLIDIDSVPTyK | SEQ ID NO: 104 |
| 106 DDX17 | NP_006377.2 | Helicase | Y580 | TTSSANNPNLMyQDECDRR | SEQ ID NO: 105 |
| 107 DDX23 | NP_004809.2 | Helicase | Y599 | MLANFESGKHKyR | SEQ ID NO: 106 |
| 108 ASPA | NP_000040.1 | Hydrolase | Y64 | yIDCDLNRIFDLENLGKK | SEQ ID NO: 107 |
| 109 HAGH | NP_005317.2 | Hydrolase, esterase | Y145 | FyEGTADEMCKALLEVLGR | SEQ ID NO: 108 |

TABLE 1-continued

Newly Discovered Leukemia-related Phosphorylation Sites.

| A<br>Protein<br>Name | B<br>Accession<br>No. | C<br>Protein Type | D<br>Phospho-<br>Residue | E<br>Phosphorylation<br>Site Sequence | H<br>SEQ ID NO |
|---|---|---|---|---|---|
| 110 HINT1 | NP_005331.1 | Hydrolase, esterase | Y109 | MVVNEGSDGGQSVyHVHLHVLGGR | SEQ ID NO: 109 |
| 111 MPG | NP_001015052.1 | Hydrolase, non-esterase | Y66 | CLGPPTTPGPyR | SEQ ID NO: 110 |
| 112 RENT1 | NP_002902.2 | Hydrolase, non-esterase | Y114 | TSQLLAELNFEEDEEDTYyTK | SEQ ID NO: 111 |
| 113 UNG | NP_550433.1 | Hydrolase, non-esterase | Y8 | MIGQKTLySFFSPSPAR | SEQ ID NO: 112 |
| 114 NCDN | NP_001014839.1 | Inhibitor protein | Y378 | EAIGAVIHyLLQVGSEKQK | SEQ ID NO: 113 |
| 115 SPRED1 | NP_689807.1 | Inhibitor protein | Y187 | RVyMQSQANQITFGQPGLDIQSRSMEYVQR | SEQ ID NO: 114 |
| 116 SUFU | NP_057253.2 | Inhibitor protein | Y60 | yWLGGPDPLDYVSMYR | SEQ ID NO: 115 |
| 117 PIN4 | NP_006214.2 | Isomerase | Y147 | FGyHIIMVEGR | SEQ ID NO: 116 |
| 118 IPMK | NP_689416.1 | Kinase (non-protein) | Y127 | YLPKYYGIWSPPTAPNDLyLKLEDVTHK | SEQ ID NO: 117 |
| 119 TAOK3 | NP_057365.2 | KINASE; Protein kinase, Ser/Thr non-receptor) | Y429 | PTQSVQSQALHyR | SEQ ID NO: 118 |
| 120 TLK1 | NP_036422.3 | KINASE; Protein kinase, Ser/Thr (non-receptor) | Y669 | EPPKISNKVDVWSVGVIFFQCLyGR | SEQ ID NO: 119 |
| 121 ACAS2L | NP_115890.2 | Ligase | Y623 | IAKyAVPDEILVVKRLPKTR | SEQ ID NO: 120 |
| 122 SCLY | NP_057594.2 | Lyase | Y33 | VyMDYNATTPLEPEVIQAMTK | SEQ ID NO: 121 |
| 123 SCLY | NP_057594.2 | Lyase | Y36 | VYMDyNATTPLEPEVIQAMTK | SEQ ID NO: 122 |
| 124 NSD1 | NP_071900.2 | Methyltransferase | Y1400 | TPGNyESKRQRKPTKKLLESNDLDPGFMPK | SEQ ID NO: 123 |
| 125 MRPL38 | NP_115867.1 | Mitochondrial | Y154 | MPVyCGNEVTPTEAAQAPEV | SEQ ID NO: 124 |
| 126 RTN4IP1 | NP_116119.2 | Mitochondrial | Y94 | MRSGyGATALNMK | SEQ ID NO: 125 |
| 127 DNAH11 | NP_003768.2 | Motor protein | Y437 | VQVAVNILKTFKNSFFNyRK | SEQ ID NO: 126 |
| 128 DNAH11 | NP_003768.2 | Motor protein | Y759 | yIGNLDLLVQGYNKLK | SEQ ID NO: 127 |
| 129 DNAH3 | NP_060009.1 | Motor protein | Y1559 | FRTVAMMVPDyALIGEISL | SEQ ID NO: 128 |
| 130 DNAH8 | NP_001362.1 | Motor protein | Y1010 | DISKLVLLLSSSVNSLRKAAHEALQDFQKyK | SEQ ID NO: 129 |
| 131 MYH14 | NP_079005.2 | Motor protein | Y1045 | RRRRSRASISyGSNMRPQSQTWRDRLR | SEQ ID NO: 130 |
| 132 MYH15 | XP_036988.9 | Motor protein | Y362 | YGCyKLTGAIMHFGNMK | SEQ ID NO: 131 |
| 133 MYO1G | NP_149043.1 | Motor protein | Y548 | LLyNSTDPTLR | SEQ ID NO: 132 |
| 134 MYBPC3 | NP_000247.1 | Myosin binding protein | Y1119 | KTMEWFTVLEHyRR | SEQ ID NO: 133 |
| 135 COX11 | NP_004366.1 | Oxidoreductase | Y117 | QNKTTLTYVAAVAVGMLGASYAAVPLyR | SEQ ID NO: 134 |
| 136 NUDT11 | NP_060629.2 | Phosphatase (non-protein) | Y11 | MKCKPNQTRTyDPEGFKK | SEQ ID NO: 135 |
| 137 PPP2R5B | NP_006235.1 | Phosphatase, regulatory subunit | Y244 | FIyEFEHFNGVAELLEILGSIINGFALPLK | SEQ ID NO: 136 |

TABLE 1-continued

Newly Discovered Leukemia-related Phosphorylation Sites.

| A Protein Name | B Accession No. | C Protein Type | D Phospho-Residue | E Phosphorylation Site Sequence | H SEQ ID NO |
|---|---|---|---|---|---|
| 138 PTPN22 | NP_036543.2 | Phosphatase; Protein phosphatase, tyrosine (non-receptor) | Y526 | HHDSSALGVySYIPLVENPYFSSWPPSGTSSK | SEQ ID NO: 137 |
| 139 PTPN22 | NP_036543.2 | Phosphatase; Protein phosphatase, tyrosine (non-receptor) | Y528 | HHDSSALGVYSyIPLVENPYFSSWPPSGTSSK | SEQ ID NO: 138 |
| 140 PTPN22 | NP_036543.2 | Phosphatase; Protein phosphatase, tyrosine (non-receptor) | Y536 | HHDSSALGVYSYIPLVENPyFSSWPPSGTSSK | SEQ ID NO: 139 |
| 141 PTPRCAP | NP_005599.1 | Phosphatase; Receptor protein phosphatase, tyrosine | Y64 | DSGGyYHPAR | SEQ ID NO: 140 |
| 142 PUM1 | NP_055491.1 | Phosphatase; Receptor protein phosphatase, tyrosine | Y83 | SQDDAMVDyFFQR | SEQ ID NO: 141 |
| 143 ADAMTS14 | NP_542453.2 | Protease (non-proteasomal) | Y38 | LSDyGVTVPCSTDFR | SEQ ID NO: 142 |
| 144 SENP2 | NP_067640.2 | Protease (non-proteasomal) | Y239 | LKESGHGNSVCPVTSNyHSSQR | SEQ ID NO: 143 |
| 145 TRHDE | NP_037513.1 | Protease (non-proteasomal) | Y179 | NATRyVVLHASR | SEQ ID NO: 144 |
| 146 TRHDE | NP_037513.1 | Protease (non-proteasomal) | Y672 | ITyLDKGSWLLGNINQTGYFR | SEQ ID NO: 145 |
| 147 AVO3 | NP_689969.2 | Protein kinase, regulatory subunit | Y1269 | TSHyLTPQSNHLSLSK | SEQ ID NO: 146 |
| 148 BCCIP | NP_057651.1 | Protein kinase, regulatory subunit | Y257 | AALMFANAEEEFFyEEQGKPEVLGGPDTR | SEQ ID NO: 147 |
| 149 CELSR2 | NP_001399.1 | Receptor, GPCR | Y1459 | yYNKPLLGQTGLPQGPSEQK | SEQ ID NO: 148 |
| 150 CELSR2 | NP_001399.1 | Receptor, GPCR | Y1460 | YyNKPLLGQTGLPQGPSEQK | SEQ ID NO: 149 |
| 151 GPR172A | NP_078807.1 | Receptor, GPCR | Y430 | PALLAAGVAIQVGSLLGAVAMFPPTSIy-HVFHSR | SEQ ID NO: 150 |
| 152 OR10A6 | NP_001004461.1 | Receptor, GPCR | Y259 | AFSTCAAHLTSVTLFYGTASMTyLQPK | SEQ ID NO: 151 |
| 153 OR2A7 | NP_001005328.1 | Receptor, GPCR | Y258 | AFCTCFSHLCVIGLFYGTAIIMyVGPR | SEQ ID NO: 152 |
| 154 OR2B2 | NP_149046.1 | Receptor, GPCR | Y290 | GKMVSLFCGIIAPMLNPLIyTLR | SEQ ID NO: 153 |
| 155 OR2G3 | NP_001001914.1 | Receptor, GPCR | Y102 | TITYGGCVAQLyISLALGSTECILLADMALDR | SEQ ID NO: 154 |
| 156 OR2T27 | NP_001001824.1 | Receptor, GPCR | Y290 | AVSAFYTILTPMLNPLIySLR | SEQ ID NO: 155 |
| 157 OR2T29 | NP_001004694.1 | Receptor, GPCR | Y276 | DMMVSVFyTILTPVLNPLIYSLRNKDVMGALK | SEQ ID NO: 156 |
| 158 OR2T29 | NP_001004694.1 | Receptor, GPCR | Y288 | DMMVSVFYTILTPVLNPLIySLRNKDVMGALK | SEQ ID NO: 157 |
| 159 OR5P3 | NP_703146.1 | Receptor, GPCR | Y290 | SSYSTDQNKVVSVFYTVVIPMLNPLIySLR | SEQ ID NO: 158 |
| 160 OR7G1 | NP_001005192.1 | Receptor, GPCR | Y235 | MPSARGKyK | SEQ ID NO: 159 |
| 161 OR9A4 | NP_001001656.1 | Receptor, GPCR | Y34 | yLVTLMGNTVIIMIVCVDKRL | SEQ ID NO: 160 |
| 162 JMJD1C | NP_004232.2 | Receptor, misc. | Y377 | yVSYISPLSAVSVMEDK | SEQ ID NO: 161 |

TABLE 1-continued

Newly Discovered Leukemia-related Phosphorylation Sites.

| | A<br>Protein<br>Name | B<br>Accession<br>No. | C<br>Protein Type | D<br>Phospho-<br>Residue | E<br>Phosphorylation<br>Site Sequence | H<br>SEQ ID NO |
|---|---|---|---|---|---|---|
| 163 | JMJD1C | NP_004232.2 | Receptor, misc. | Y380 | YVSyISPLSAVSVMEDK | SEQ ID NO: 162 |
| 164 | LILRB4 | NP_006838.2 | Receptor, misc. | Y360 | QSPHDEDPQAVTyAK | SEQ ID NO: 163 |
| 165 | LILRB4 | NP_006838.2 | Receptor, misc. | Y442 | QKATEPPPSQEGASPAEPSVyATLAIH | SEQ ID NO: 164 |
| 166 | NRBF2 | NP_110386.1 | Receptor, misc. | Y143 | CLPEIQGIFDRDPDTLLyLLQQK | SEQ ID NO: 165 |
| 167 | ROBO1 | NP_002932.1 | Receptor, misc. | Y328 | VTAGDMGSyTCVAENMVGK | SEQ ID NO: 166 |
| 168 | ROBO1 | NP_002932.1 | Receptor, misc. | Y932 | NGLTSTyAGIR | SEQ ID NO: 167 |
| 169 | SCARB1 | NP_005496.3 | Receptor, misc. | Y490 | DKEAIQAySESLMTSAPK | SEQ ID NO: 168 |
| 170 | TREM1 | | Receptor, misc. | Y116 | MVNLQVEDSGLYQCVIyQPPK | SEQ ID NO: 169 |
| 171 | ARPP-19 | NP_006619.1 | RNA binding protein | Y36 | ARyPHLGQKPGGSDFLR | SEQ ID NO: 170 |
| 172 | CASC3 | NP_031385.2 | RNA binding protein | Y181 | HLDDDEDRKNPAyIPR | SEQ ID NO: 171 |
| 173 | CPSF6 | NP_008938.1 | RNA binding protein | Y76 | GAAPNVVYTyTGK | SEQ ID NO: 172 |
| 174 | CPSF6 | NP_008938.1 | RNA binding protein | Y390 | GPPPTDPYGRPPPyDRGDYGPPGR | SEQ ID NO: 173 |
| 175 | CPSF6 | NP_008938.1 | RNA binding protein | Y395 | GPPPTDPYGRPPPYDRGDyGPPGR | SEQ ID NO: 174 |
| 176 | ELAVL1 | NP_001410.2 | RNA binding protein | Y200 | NVALLSQLyHSPAR | SEQ ID NO: 175 |
| 177 | GEMIN4 | NP_056536.1 | RNA binding protein | Y343 | EWGEELQAVLRSSQGTSyDSYR | SEQ ID NO: 176 |
| 178 | GRSF1 | NP_002083.2 | RNA binding protein | Y79 | SQESKTTYLEDLPPPPEyELAPSKLEEEVDDVF | SEQ ID NO: 177 |
| 179 | HNRPA0 | NP_006796.1 | RNA binding protein | Y145 | GFGFVyFQNHDAADKAAVVK | SEQ ID NO: 178 |
| 180 | HNRPA1 | NP_002127.1 | RNA binding protein | Y167 | yHTVNGHNCEVR | SEQ ID NO: 179 |
| 181 | HNRPA2B1 | NP_002128.1 | RNA binding protein | Y162 | yHTINGHNAEVR | SEQ ID NO: 180 |
| 182 | HNRPC | NP_004491.1 | RNA binding protein | Y124 | DYYDRMySYPAR | SEQ ID NO: 181 |
| 183 | HNRPH2 | NP_062543.1 | RNA binding protein | Y240 | GAYGGGyGGYDDYGGYNDGYGFGSDR | SEQ ID NO: 182 |
| 184 | HNRPH2 | NP_062543.1 | RNA binding protein | Y249 | GAYGGGYGGYDDYGGyNDGYGFGSDR | SEQ ID NO: 183 |
| 185 | HNRPK | | RNA binding protein | Y380 | GSyGDLGGPIITTQVTIPK | SEQ ID NO: 184 |
| 186 | HNRPUL1 | NP_008971.2 | RNA binding protein | Y124 | QNQFYDTQVIKQENESGyER | SEQ ID NO: 185 |
| 187 | KHDRBS1 | NP_006550.1 | RNA binding protein | Y396 | SQSQGDSEyYDYGHGEVQDSY | SEQ ID NO: 186 |
| 188 | KHDRBS1 | NP_006550.1 | RNA binding protein | Y397 | GYYSQSQGDSEYyDYGHGE | SEQ ID NO: 187 |
| 189 | KHDRBS1 | NP_006550.1 | RNA binding protein | Y435 | GAyREHPYGRY | SEQ ID NO: 188 |

TABLE 1-continued

Newly Discovered Leukemia-related Phosphorylation Sites.

| A<br>Protein<br>Name | B<br>Accession<br>No. | C<br>Protein Type | D<br>Phospho-<br>Residue | E<br>Phosphorylation<br>Site Sequence | H<br>SEQ ID NO |
|---|---|---|---|---|---|
| 190 MATR3 | NP_061322.2 | RNA binding protein | Y171 | SATREPPyRVPR | SEQ ID NO: 189 |
| 191 MATR3 | NP_061322.2 | RNA binding protein | Y243 | CRDDSFFGETSHNyHKFDSEYER | SEQ ID NO: 190 |
| 192 MATR3 | NP_061322.2 | RNA binding protein | Y250 | CRDDSFFGETSHNYHKFDSEyER | SEQ ID NO: 191 |
| 193 NOB1P | NP_054781.1 | RNA binding protein | Y366 | QKTNVFAPDyIAGVSPFVENDISSR | SEQ ID NO: 192 |
| 194 NOLA1 | NP_061856.1 | RNA binding protein | Y149 | FYIDPyKLLPLQR | SEQ ID NO: 193 |
| 195 NXF1 | NP_006353.2 | RNA binding protein | Y75 | YNPyTTRPNR | SEQ ID NO: 194 |
| 196 PABPC3 | NP_112241.2 | RNA binding protein | Y54 | ICRDLITSGSSNyAYVNFQHTK | SEQ ID NO: 195 |
| 197 PABPC3 | NP_112241.2 | RNA binding protein | Y56 | ICRDLITSGSSNYAyVNFQHTK | SEQ ID NO: 196 |
| 198 PAI-RBP1 | NP_001018077.1 | RNA binding protein | Y231 | GGSGSHNWGTVKDELTESPKyIQK | SEQ ID NO: 197 |
| 199 PCBP2 | NP_005007.2 | RNA binding protein | Y230 | GPPLEAyTIQGQYAIPQPD | SEQ ID NO: 198 |
| 200 PRPF31 | NP_056444.2 | RNA binding protein | Y207 | HRIYEyVESR | SEQ ID NO: 199 |
| 201 PTBP2 | NP_067013.1 | RNA binding protein | Y127 | NQPIyIQYSNHK | SEQ ID NO: 200 |
| 202 RBM14 | NP_006319.1 | RNA binding protein | Y614 | LAELSDyR | SEQ ID NO: 201 |
| 203 RBM15 | NP_073605.4 | RNA binding protein | Y251 | IEAVyVSR | SEQ ID NO: 202 |
| 204 RBM22 | NP_060517.1 | RNA binding protein | Y116 | SDVNKEyYTQNMER | SEQ ID NO: 203 |
| 205 RBM3 | | RNA binding protein | Y143 | NQGGyDRYSGGNYRDNYDN | SEQ ID NO: 204 |
| 206 RBM3 | NP_006734.1 | RNA binding protein | Y151 | DYNGRNQGGYDRYSGGNyR | SEQ ID NO: 205 |
| 207 RBMX | NP_002130.2 | RNA binding protein | Y134 | GGHMDDGGySMNFNMSSSR | SEQ ID NO: 206 |
| 208 RBMX | NP_002130.2 | RNA binding protein | Y220 | DSySSRDYPSSR | SEQ ID NO: 207 |
| 209 RBMX | NP_002130.2 | RNA binding protein | Y255 | DYGHSSSRDDyPSR | SEQ ID NO: 208 |
| 210 RNASEH1 | NP_002927.2 | RNA binding protein | Y114 | EPLDGDGHESAEPyAKHMKPSVEPAPPVSR | SEQ ID NO: 209 |
| 211 ROD1 | NP_005147.3 | RNA binding protein | Y127 | SQPVyIQYSNHR | SEQ ID NO: 210 |
| 212 RPL23A | NP_000975.2 | RNA binding protein | Y74 | LDHyAIIKFPLTTESAMK | SEQ ID NO: 211 |
| 213 RPL4 | NP_000959.2 | RNA binding protein | Y264 | KLDELyGTWR | SEQ ID NO: 212 |

TABLE 1-continued

Newly Discovered Leukemia-related Phosphorylation Sites.

| | A<br>Protein<br>Name | B<br>Accession<br>No. | C<br>Protein Type | D<br>Phospho-<br>Residue | E<br>Phosphorylation<br>Site Sequence | H<br>SEQ ID NO |
|---|---|---|---|---|---|---|
| 214 | SF1 | NP_004621.2 | RNA binding protein | Y52 | EQERAyIVQLQIEDLTR | SEQ ID NO: 213 |
| 215 | SF3A2 | NP_009096.2 | RNA binding protein | Y45 | QLALETIDINKDPyFMK | SEQ ID NO: 214 |
| 216 | SFPQ | NP_005057.1 | RNA binding protein | Y527 | DAKDKLESEMEDAyHEHQANLLR | SEQ ID NO: 215 |
| 217 | SFPQ | NP_005057.1 | RNA binding protein | Y698 | GREEyEGPNKKPR | SEQ ID NO: 216 |
| 218 | SFRS10 | NP_004584.1 | RNA binding protein | Y128 | HVGNRANPDPNCCLGVFGLSLyTTER | SEQ ID NO: 217 |
| 219 | SFRS2 | NP_003007.2 | RNA binding protein | Y44 | VGDVyIPR | SEQ ID NO: 218 |
| 220 | SFRS3 | NP_003008.1 | RNA binding protein | Y32 | AFGyYGPLR | SEQ ID NO: 219 |
| 221 | SFRS6 | NP_006266.2 | RNA binding protein | Y191 | PRTSHRRSySGSRSR | SEQ ID NO: 220 |
| 222 | SFRS9 | NP_003760.1 | RNA binding protein | Y214 | GSPHyFSPFRPY | SEQ ID NO: 221 |
| 223 | SR140 | XP_031553.8 | RNA binding protein | Y173 | AAAEIyEEFLAAFEGSDGNK | SEQ ID NO: 222 |
| 224 | XRN1 | NP_061874.3 | RNA binding protein | Y1248 | MQyFQPTIQEK | SEQ ID NO: 223 |
| 225 | HNRPM | NP_005959.2 | RNA binding proteins | Y64 | GGNRFEPyANPTK | SEQ ID NO: 224 |
| 226 | HNRPM | NP_005959.2 | RNA binding proteins | Y681 | DKFNECGHVLyADIK | SEQ ID NO: 225 |
| 227 | AZGP1 | NP_001176.1 | Secreted protein | Y107 | DIVEyYNDSNGSHVLQGR | SEQ ID NO: 226 |
| 228 | FGF10 | NP_004456.1 | Secreted protein | Y70 | GQDMVSPEATNSSSSSFSSPSSAGRHVRSy | SEQ ID NO: 227 |
| 229 | FRZB | NP_001454.2 | Secreted protein | Y197 | CKPIRATQKTYFRNNYNyVIR | SEQ ID NO: 228 |
| 230 | MAML2 | NP_115803.1 | Transcription, coactivator/ corepressor | Y513 | IPSPSFGQQTFSPQSSPMPGVAGGSGQSKV MANyMYK | SEQ ID NO: 229 |
| 231 | MAML2 | NP_115803.1 | Transcription coactivator/ corepressor | Y515 | IPSPSFGQQTFSPQSSPMPGVAGGSGQSKV MANYMyK | SEQ ID NO: 230 |
| 232 | SLB | NP_056477.1 | Transcription, coactivator/ corepressor | Y222 | KIVAyGKEGHMLQTFDYSRDPQER | SEQ ID NO: 231 |
| 233 | SUPT16H | NP_009123.1 | Transcription, coactivator/ corepressor | Y1006 | KADRESRyEEEEEQSR | SEQ ID NO: 232 |
| 234 | UNC5CL | NP_775832.1 | Transcription, coactivator/ corepressor | Y194 | PCTLTFKHCAEQPSHARTySSNTTLLDAKVWR | SEQ ID NO: 233 |
| 235 | CNOT2 | NP_055330.1 | Transcription factor | Y37 | FVEGVDSDyHDENMYYSQSSMFPHR | SEQ ID NO: 234 |
| 236 | CNOT2 | NP_055330.1 | Transcription factor | Y43 | FVEGVDSDYHDENMyYSQSSMFPHR | SEQ ID NO: 235 |
| 237 | CNOT2 | NP_055330.1 | Transcription factor | Y44 | FVEGVDSDYHDENMYySQSSMFPHR | SEQ ID NO: 236 |

TABLE 1-continued

Newly Discovered Leukemia-related Phosphorylation Sites.

| | A<br>Protein<br>Name | B<br>Accession<br>No. | C<br>Protein Type | D<br>Phospho-<br>Residue | E<br>Phosphorylation<br>Site Sequence | H<br>SEQ ID NO |
|---|---|---|---|---|---|---|
| 238 | FOXJ1 | NP_001445.2 | Transcription factor | Y148 | ITLSAIyKWITDNFCYFR | SEQ ID NO: 237 |
| 239 | FOXJ1 | NP_001445.2 | Transcription factor | Y157 | ITLSAIYKWITDNFCyFR | SEQ ID NO: 238 |
| 240 | IRF2BP1 | NP_056464.1 | Transcription factor | Y268 | VFAFDATARPPGyEFELK | SEQ ID NO: 239 |
| 241 | LITAF | NP_004853.2 | Transcription factor | Y32 | NSyYPTPPAPMPGPT | SEQ ID NO: 240 |
| 242 | LITAF | NP_004853.2 | Transcription factor | Y62 | TGLVTGPDGKGMNPPSyTQPAPIPNNNPIT | SEQ ID NO: 241 |
| 243 | SNAPC3 | NP_001034786.1 | Transcription factor | Y157 | QETFVyEMESHAIGKK | SEQ ID NO: 242 |
| 244 | SPDEF | NP_036523.1 | Transcription factor | Y312 | LSRSIRQyYKKGIIRKPDISQRLVYQFVHPI | SEQ ID NO: 243 |
| 245 | SPDEF | NP_036523.1 | Transcription factor | Y313 | LSRSIRQYyKKGIIRKPDISQRLVYQFVHPI | SEQ ID NO: 244 |
| 246 | ZHX2 | NP_055758.1 | Transcription factor | Y731 | KATKPMAESPKNGGDWPQYyKDPK | SEQ ID NO: 245 |
| 247 | POLR3B | NP_060552.3 | Transcription initiation complex | Y714 | IDTLMYLLAyPQKPMVK | SEQ ID NO: 246 |
| 248 | CSS3 | NP_787052.3 | Transferase | Y677 | GyQNKYPKAEMTLIPMKGEFSR | SEQ ID NO: 247 |
| 249 | GALNT4 | NP_003765.2 | Transferase | Y181 | TIHSVLETSPAVLLKEIILVDDLSDRVyLK | SEQ ID NO: 248 |
| 250 | PARP3 | NP_001003931.1 | Transferase | Y420 | VGKGIyFASENSKSAGYVIGMK | SEQ ID NO: 249 |
| 251 | PARP3 | NP_001003931.1 | Transferase | Y431 | VGKGIYFASENSKSAGyVIGMK | SEQ ID NO: 250 |
| 252 | SLC27A1 | NP_940982.1 | Transporter, active | Y488 | GDSAyLSGDVLVMDELGYMYFR | SEQ ID NO: 251 |
| 253 | SLC27A1 | NP_940982.1 | Transporter, active | Y501 | GDSAYLSGDVLVMDELGyMYFR | SEQ ID NO: 252 |
| 254 | SLC27A1 | NP_940982.1 | Transporter, active | Y503 | GDSAYLSGDVLVMDELGYMyFR | SEQ ID NO: 253 |
| 255 | SLC29A4 | NP_694979.2 | Transporter, active | Y198 | RyTQGVMTGESTAGVMISLSRILTK | SEQ ID NO: 254 |
| 256 | SLC7A6 | AAH28216.1 | Transporter, active | Y13 | EPGRPTPTyHLVPNTSQSQVEEDVSSPPQR | SEQ ID NO: 255 |
| 257 | SLC12A7 | NP_006589.1 | Transporter, facilitator | Y991 | LIAEKyR | SEQ ID NO: 256 |
| 258 | SLC26A1 | NP_602297.1 | Transporter, facilitator | Y191 | VATALTLMTGLyQTSWGR | SEQ ID NO: 257 |
| 259 | SLC3582 | NP_835361.1 | Transporter, facilitator | Y54 | MVPGyLLVQYF | SEQ ID NO: 258 |
| 260 | SLC6A5 | NP_004202.2 | Transporter, facilitator | Y710 | yPNWSMVLGWLMLACSVIWIPIMFVIKM-HLAPGR | SEQ ID NO: 259 |
| 261 | RNF139 | NP_009149.2 | Ubiquitin conjugating pathway | Y450 | VIVSLTVYTLFMIDGYyNVLWEKLDDYVYYVR | SEQ ID NO: 260 |

TABLE 1-continued

Newly Discovered Leukemia-related Phosphorylation Sites.

| | A<br>Protein<br>Name | B<br>Accession<br>No. | C<br>Protein Type | D<br>Phospho-<br>Residue | E<br>Phosphorylation<br>Site Sequence | H<br>SEQ ID NO |
|---|---|---|---|---|---|---|
| 262 | UBE3B | NP_569733.2 | Ubiquitin conjugating pathway | Y695 | MLEDGyEQLRQLSQHAMK | SEQ ID NO: 261 |
| 263 | USP15 | NP_006304.1 | Ubiquitin conjugating pathway | Y234 | NSNyCLPSYTAYKNYDYSEPGR | SEQ ID NO: 262 |
| 264 | USP15 | NP_006304.1 | Ubiquitin conjugating pathway | Y245 | NSNYCLPSYTAYKNyDYSEPGR | SEQ ID NO: 263 |
| 265 | USP15 | NP_006304.1 | Ubiquitin conjugating pathway | Y247 | NSNYCLPSYTAYKNYDySEPGR | SEQ ID NO: 264 |
| 266 | USP2S | NP_.037528.3 | Ubiquitin conjugating pathway | Y740 | ESETSVTTAQAAGDPEyLEQPSRSDFSK | SEQ ID NO: 265 |
| 267 | USP3 | NP_006528.2 | Ubiquitin conjugating pathway | Y383 | SFTDLEELDETELyMCHKCKK | SEQ ID NO: 266 |
| 268 | U5P38 | NPJ_15946.2 | Ubiquitin conjugating pathway | Y987 | LyLQEQELNARAR | SEQ ID NO: 267 |
| 269 | U5P48 | NP_115612.4 | Ubiquitin conjugating pathway | Y575 | ILRLKNQLNEDyKTVNNLLK | SEQ ID NO: 268 |
| 270 | CACYBP | NP_001007215.1 | Ubiquitin conjugating system | Y28 | KAELLDNEKPAAVVAPITTGyTVK | SEQ ID NO: 269 |
| 271 | CUL7 | NP_055595.2 | Ubiquitin conjugating system | Y786 | CEKHAHLyRKLITNILGGCIQMVLGQIEDHR | SEQ ID NO: 270 |
| 272 | HACE1 | NP_065822.1 | Ubiquitin conjugating system | Y677 | HILGIPVNyQDVASIDPEYAK | SEQ ID NO: 271 |
| 273 | HACE1 | NP_065822.1 | Ubiquitin conjugating system | Y687 | HILGIPVNYQDVASIDPEyAK | SEQ ID NO: 272 |
| 274 | RNF25 | NP_071898.2 | Ubiquitin conjugating system | Y432 | TPGSSyPR | SEQ ID NO: 273 |
| 275 | CLTA | NP_001824.1 | Vesicle protein | Y83 | DGGAPGPQPHGEPPGGPDAVDGVMNGEyYQESNGPTDSY | SEQ ID NO: 274 |
| 276 | CLTA | NP_001824.1 | Vesicle protein | Y84 | GGAPGPQPHGEPPGGPDAVDGVMNGEYyQE | SEQ ID NO: 275 |
| 277 | COPB2 | NP_004757.1 | Vesicle protein | Y354 | DMGSCEIyPQTIQHNPNGR | SEQ ID NO: 276 |
| 278 | HPS3 | NP_115759.2 | Vesicle protein | Y922 | CPEAVIPyANHELKEENR | SEQ ID NO: 277 |
| 279 | NSF | NP_006169.1 | Vesicle protein | Y45 | yTFTLKTHPSVVPGSIAFSLPQRK | SEQ ID NO: 278 |
| 280 | SCAMP3 | | Vesicle protein | Y41 | QYATLDVyNPFETR | SEQ ID NO: 279 |
| 281 | SNAP23 | NP_003816.2 | Vesicle protein | Y139 | QPGPVTNGQLQQPTTGAASGGyIK | SEQ ID NO: 280 |
| 282 | SNAP29 | NP_004773.1 | Vesicle protein | Y122 | SVFGGLVNyFK | SEQ ID NO: 281 |
| 283 | SNAP29 | NP_004773.1 | Vesicle protein | Y189 | GAGSAMSTDAyPKNPHLR | SEQ ID NO: 282 |
| 284 | STX1A | NP_004594.1 | Vesicle protein | Y141 | FVEVMSEYNATQSDyRER | SEQ ID NO: 283 |

TABLE 1-continued

Newly Discovered Leukemia-related Phosphorylation Sites.

| A<br>Protein<br>Name | B<br>Accession<br>No. | C<br>Protein Type | D<br>Phospho-<br>Residue | E<br>Phosphorylation<br>Site Sequence | H<br>SEQ ID NO |
|---|---|---|---|---|---|
| 285 SV2A | NP_055664.2 | Vesicle protein | Y41 | GLDRVQDEySR | SEQ ID NO: 284 |
| 286 VPS13B | NP_060360.3 | Vesicle protein | Y1453 | LLDGTHQQHGFLSLTyTK | SEQ ID NO: 285 |
| 287 VPS41 | NP_055211.1 | Vesicle protein | Y518 | KDSQNKTLLKTLAELyTYDK | SEQ ID NO: 286 |
| 288 VPS41 | NP_055211.1 | Vesicle protein | Y520 | KDSQNKTLLKTLAELYTyDK | SEQ ID NO: 287 |
| 289 VTI1B | NP_006361.1 | Vesicle protein | Y115 | YGIyAVENEHMNR | SEQ ID NO: 288 |

The short name for each protein in which a phosphorylation site has presently been identified is provided in Column A, and its SwissProt accession number (human) is provided Column B. The protein type/group into which each protein falls is provided in Column C. The identified tyrosine residue at which phosphorylation occurs in a given protein is identified in Column D, and the amino acid sequence of the phosphorylation site encompassing the tyrosine residue is provided in Column E (lower case y=the tyrosine (identified in Column D)) at which phosphorylation occurs. Table 1 above is identical to FIG. 2, except that the latter includes the disease and cell type(s) in which the particular phosphorylation site was identified (Columns F and G).

The identification of these 288 phosphorylation sites is described in more detail in Part A below and in Example 1.

DEFINITIONS

As used herein, the following terms have the meanings indicated:

"Antibody" or "antibodies" refers to all types of immunoglobulins, including IgG, IgM, IgA, IgD, and IgE, including $F_{ab}$ or antigen-recognition fragments thereof, including chimeric, polyclonal, and monoclonal antibodies. The term "does not bind" with respect to an antibody's binding to one phospho-form of a sequence means does not substantially react with as compared to the antibody's binding to the other phospho-form of the sequence for which the antibody is specific.

"Leukemia-related signaling protein" means any protein (or poly-peptide derived therefrom) enumerated in Column A of Table 1/FIG. 2, which is disclosed herein as being phosphorylated in one or more leukemia cell line(s). Leukemia-related signaling proteins may be tyrosine kinases, such as Flt-3 or BCR-Abl, or serine/threonine kinases, or direct substrates of such kinases, or may be indirect substrates downstream of such kinases in signaling pathways. A Leukemia-related signaling protein may also be phosphorylated in other cell lines (non-leukemic) harboring activated kinase activity.

"Heavy-isotope labeled peptide" (used interchangeably with AQUA peptide) means a peptide comprising at least one heavy-isotope label, which is suitable for absolute quantification or detection of a protein as described in WO/03016861, "Absolute Quantification of Proteins and Modified Forms Thereof by Multistage Mass Spectrometry" (Gygi et al.), further discussed below.

"Protein" is used interchangeably with polypeptide, and includes protein fragments and domains as well as whole protein.

"Phosphorylatable amino acid" means any amino acid that is capable of being modified by addition of a phosphate group, and includes both forms of such amino acid.

"Phosphorylatable peptide sequence" means a peptide sequence comprising a phosphorylatable amino acid.

"Phosphorylation site-specific antibody" means an antibody that specifically binds a phosphorylatable peptide sequence/epitope only when phosphorylated, or only when not phosphorylated, respectively. The term is used interchangeably with "phospho-specific" antibody.

A. Identification of Novel Leukemia-related Protein Phosphorylation Sites

The nearly 288 novel Leukemia-related signaling protein phosphorylation sites disclosed herein and listed in Table 1/FIG. 2 were discovered by employing the modified peptide isolation and characterization techniques described in "Immunoaffinity Isolation of Modified Peptides From Complex Mixtures," U.S. Patent Publication No. 20030044848, Rush et al. (the teaching of which is hereby incorporated herein by reference, in its entirety) using cellular extracts from the following human Leukemia (AML, ALL, CML and CLL) derived cell lines and patient samples: Jurkat, K562, CMK, MV4-11, SEM, HT-93, CTV-1, MOLT15, CLL-9, H1993, OCI-ly3, KBM-3, UT-7, SUPT-13, MKPL-1, HU-3, M-07e, HU-3, EHEB, SU-DHL1, OCI-ly1, DU-528, CMK, OCI-ly8, ELF-153, OCI-ly18, MEC-1, Karpas 299, CLL23LB4, OCI-ly12, M01043, CLL-10, HL60, Molm 14, MV4-11, CLL-1202, EOL-1, CLL-19, CV-1, PL21; or from the following cell lines expressing activated BCR-Abl wild type and mutant kinases such as: Baf3-p210 BCR-Abl, Baf3-M351T-BCR-ABL, Baf3-E255K-BCR-Abl, Baf3-Y253F-BCR-Abl, Baf3-T315I-BCR-ABI, 3T3-v-Abl; or activated Flt3 kinase such as Baf3-FLT3 or FLT3-ITD; or JAK2 such as Baf3/Jak2; or mutant JAK2 V617F such as Baf3-V617F-JAK2, or Tyk2 such as Baf3/Tyk2; or TEL-FGFR3 such as Baf3-Tel/FGFR3; or TpoR such as Baf3/TpoR and Baf3/cc-TpoR-IV; or FGFR1 such as 293T-FGFR. The isolation and identification of phosphopeptides from these cell lines, using an immobilized general phosphotyrosine-specific antibody, or an antibody recognizing the phosphorylated motif PXpSP is described in detail in Example 1 below. In addition to the nearly 288 previously unknown protein phosphorylation sites (tyrosine) discovered, many known phosphorylation sites were also identified (not described herein). The immunoaffinity/mass spectrometric technique described in the '848 patent Publication (the "IAP" method)—and employed as described in detail in the Examples—is briefly summarized below.

The IAP method employed generally comprises the following steps: (a) a proteinaceous preparation (e.g. a digested cell extract) comprising phosphopeptides from two or more different proteins is obtained from an organism; (b) the preparation is contacted with at least one immobilized general phosphotyrosine-specific antibody; (c) at least one phosphopeptide specifically bound by the immobilized antibody in step (b) is isolated; and (d) the modified peptide isolated in step (c) is characterized by mass spectrometry (MS) and/or tandem mass spectrometry (MS-MS). Subsequently, (e) a search program (e.g. Sequest) may be utilized to substantially match the spectra obtained for the isolated, modified peptide during the characterization of step (d) with the spectra for a known peptide sequence. A quantification step employing, e.g. SILAC or AQUA, may also be employed to quantify isolated peptides in order to compare peptide levels in a sample to a baseline.

In the IAP method as employed herein, a general phosphotyrosine-specific monoclonal antibody (commercially available from Cell Signaling Technology, Inc., Beverly, Mass., Cat #9411 (p-Tyr-100)) was used in the immunoaffinity step to isolate the widest possible number of phospho-tyrosine and phospho-serine containing peptides from the cell extracts.

Extracts from the following human Leukemia cell lines (ALL, AML, CLL, CML, respectively) were employed: Jurkat, K562, SEM, HT-93, CTV-1, MOLT15, CLL-9, H1993, OCI-ly3, KBM-3, UT-7, SUPT-13, MKPL-1, HU-3, M-07e, HU-3, EHEB, SU-DHL1, OCI-ly1, DU-528, CMK, OCI-ly8, ELF-153, OCI-ly18, MEC-1, Karpas 299, CLL23LB4, OCI-ly12, M01043, CLL-10, HL60, Molm 14, MV4-11, CLL-1202, EOL-1, CLL-19, CV-1, PL21; or from the following cell lines expressing activated BCR-Abl wild type and mutant kinases such as: Baf3-p210 BCR-Abl, Baf3-M351T-BCR-ABL, Baf3-E255K-BCR-Abl, Baf3-Y253F-BCR-Abl, Baf3-T3151-BCR-ABI, 3T3-v-Abl; or activated Flt3 kinase such as Baf3-FLT3 or FLT3-ITD; or JAK2 such as Baf3/Jak2; or mutant JAK2 V617F such as Baf3-V617F-JAK2, or Tyk2 such as Baf3/Tyk2; or TEL-FGFR3 such as Baf3-Tel/FGFR3; or TpoR such as Baf3/TpoR and Baf3/cc-TpoR-IV; or FGFR1 such as 293T-FGFR.

As described in more detail in the Examples, lysates were prepared from these cells line and digested with trypsin after treatment with DTT and iodoacetamide to alkylate cysteine residues. Before the immunoaffinity step, peptides were pre-fractionated by reversed-phase solid phase extraction using Sep-Pak $C_{18}$ columns to separate peptides from other cellular components. The solid phase extraction cartridges were eluted with varying steps of acetonitrile. Each lyophilized peptide fraction was redissolved in PBS and treated with phosphotyrosine (P-Tyr-100, CST #9411) immobilized on protein G-Sepharose or Protein A-Sepharose. Immunoaffinity-purified peptides were eluted with 0.1% TFA and a portion of this fraction was concentrated with Stage or Zip tips and analyzed by LC-MS/MS, using a ThermoFinnigan LTQ ion trap mass spectrometer. Peptides were eluted from a 10 cm×75 µm reversed-phase column with a 45-min linear gradient of acetonitrile. MS/MS spectra were evaluated using the program Sequest with the NCBI human protein database.

This revealed a total of nearly 288 novel tyrosine phosphorylation sites in signaling pathways affected by kinase activation or active in leukemia cells. The identified phosphorylation sites and their parent proteins are enumerated in Table 1/FIG. 2. The tyrosine (human sequence) at which phosphorylation occurs is provided in Column D, and the peptide sequence encompassing the phosphorylatable tyrosine residue at the site is provided in Column E. FIG. 2 also shows the particular type of leukemic disease (see Column G) and cell line(s) (see Column F) in which a particular phosphorylation site was discovered.

As a result of the discovery of these phosphorylation sites, phospho-specific antibodies and AQUA peptides for the detection of and quantification of these sites and their parent proteins may now be produced by standard methods, described below. These new reagents will prove highly useful in, e.g., studying the signaling pathways and events underlying the progression of leukemias and the identification of new biomarkers and targets for diagnosis and treatment of such diseases.

B. Antibodies and Cell Lines

Isolated phosphorylation site-specific antibodies that specifically bind a Leukemia-related signaling protein disclosed in Column A of Table 1 only when phosphorylated (or only when not phosphorylated) at the corresponding amino acid and phosphorylation site listed in Columns D and E of Table 1/FIG. 2 may now be produced by standard antibody production methods, such as anti-peptide antibody methods, using the phosphorylation site sequence information provided in Column E of Table 1. For example, two previously unknown AP4E1 adaptor/scaffold phosphorylation sites (tyrosines 830 and 831) (see Rows 8 and 9 of Table 1/FIG. 2) are presently disclosed. Thus, antibodies that specifically bind either of these novel AP4E1 adaptor/scaffold sites can now be produced, e.g. by immunizing an animal with a peptide antigen comprising all or part of the amino acid sequence encompassing the respective phosphorylated residue (e.g. a peptide antigen comprising the sequence set forth in Row 357, Column E, of Table 1 (SEQ ID NO: 7) (which encompasses the phosphorylated tyrosine at position 830 in AP4E1), to produce an antibody that only binds AP4E1 adaptor/scaffold when phosphorylated at that site.

Polyclonal antibodies of the invention may be produced according to standard techniques by immunizing a suitable animal (e.g., rabbit, goat, etc.) with a peptide antigen corresponding to the Leukemia-related phosphorylation site of interest (i.e. a phosphorylation site enumerated in Column E of Table 1, which comprises the corresponding phosphorylatable amino acid listed in Column D of Table 1), collecting immune serum from the animal, and separating the polyclonal antibodies from the immune serum, in accordance with known procedures. For example, a peptide antigen corresponding to all or part of the novel RASGRP2 guanine nucleotide exchange factor phosphorylation site disclosed herein (SEQ ID NO: 104=HSSLIDIDSVPTyK, encompassing phosphorylated tyrosine 189 (see Row 104 of Table 1)) may be used to produce antibodies that only bind RASGRP2 when phosphorylated at Tyr 104. Similarly, a peptide comprising all or part of any one of the phosphorylation site sequences provided in Column E of Table 1 may employed as an antigen to produce an antibody that only binds the corresponding protein listed in Column A of Table 1 when phosphorylated (or when not phosphorylated) at the corresponding residue listed in Column D. If an antibody that only binds the protein when phosphorylated at the disclosed site is desired, the peptide antigen includes the phosphorylated form of the amino acid. Conversely, if an antibody that only binds the protein when not phosphorylated at the disclosed site is desired, the peptide antigen includes the non-phosphorylated form of the amino acid.

Peptide antigens suitable for producing antibodies of the invention may be designed, constructed and employed in accordance with well-known techniques. See, e.g., ANTIBODIES: A LABORATORY MANUAL, Chapter 5, p. 75-76, Harlow &

Lane Eds., Cold Spring Harbor Laboratory (1988); Czernik, *Methods In Enzymology*, 201: 264-283 (1991); Merrifield, *J. Am. Chem. Soc.* 85:21-49 (1962)).

It will be appreciated by those of skill in the art that longer or shorter phosphopeptide antigens may be employed. See Id. For example, a peptide antigen may comprise the full sequence disclosed in Column E of Table 1/FIG. 2, or it may comprise additional amino acids flanking such disclosed sequence, or may comprise of only a portion of the disclosed sequence immediately flanking the phosphorylatable amino acid (indicated in Column E by lowercase "y"). Typically, a desirable peptide antigen will comprise four or more amino acids flanking each side of the phosphorylatable amino acid and encompassing it. Polyclonal antibodies produced as described herein may be screened as further described below.

Monoclonal antibodies of the invention may be produced in a hybridoma cell line according to the well-known technique of Kohler and Milstein. See *Nature* 265:495-97 (1975); Kohler and Milstein, *Eur. J. Immunol.* 6: 511 (1976); see also, CURRENT PROTOCOLS IN MOLECULAR BIOLOGY, Ausubel et al. Eds. (1989). Monoclonal antibodies so produced are highly specific, and improve the selectivity and specificity of diagnostic assay methods provided by the invention. For example, a solution containing the appropriate antigen may be injected into a mouse or other species and, after a sufficient time (in keeping with conventional techniques), the animal is sacrificed and spleen cells obtained. The spleen cells are then immortalized by fusing them with myeloma cells, typically in the presence of polyethylene glycol, to produce hybridoma cells. Rabbit fusion hybridomas, for example, may be produced as described in U.S. Pat. No. 5,675,063, C. Knight, Issued Oct. 7, 1997. The hybridoma cells are then grown in a suitable selection media, such as hypoxanthine-aminopterin-thymidine (HAT), and the supernatant screened for monoclonal antibodies having the desired specificity, as described below. The secreted antibody may be recovered from tissue culture supernatant by conventional methods such as precipitation, ion exchange or affinity chromatography, or the like.

Monoclonal Fab fragments may also be produced in *Escherichia coli* by recombinant techniques known to those skilled in the art. See, e.g., W. Huse, *Science* 246: 1275-81 (1989); Mullinax et al., *Proc. Nat'l Acad. Sci.* 87: 8095 (1990). If monoclonal antibodies of one isotype are preferred for a particular application, particular isotypes can be prepared directly, by selecting from the initial fusion, or prepared secondarily, from a parental hybridoma secreting a monoclonal antibody of different isotype by using the sib selection technique to isolate class-switch variants (Steplewski, et al., *Proc. Nat'l. Acad. Sci.*, 82: 8653 (1985); Spira et al., *J. Immunol. Methods*, 74: 307 (1984)).

The preferred epitope of a phosphorylation-site specific antibody of the invention is a peptide fragment consisting essentially of about 8 to 17 amino acids including the phosphorylatable tyrosine, wherein about 3 to 8 amino acids are positioned on each side of the phosphorylatable tyrosine (for example, the BIRC4BP tyrosine 261 phosphorylation site sequence disclosed in Row 8, Column E of Table 1), and antibodies of the invention thus specifically bind a target Leukemia-related signaling polypeptide comprising such epitopic sequence. Particularly preferred epitopes bound by the antibodies of the invention comprise all or part of a phosphorylatable site sequence listed in Column E of Table 1, including the phosphorylatable amino acid.

Included in the scope of the invention are equivalent non-antibody molecules, such as protein binding domains or nucleic acid aptamers, which bind, in a phospho-specific manner, to essentially the same phosphorylatable epitope to which the phospho-specific antibodies of the invention bind. See, e.g., Neuberger et al., *Nature* 312: 604 (1984). Such equivalent non-antibody reagents may be suitably employed in the methods of the invention further described below.

Antibodies provided by the invention may be any type of immunoglobulins, including IgG, IgM, IgA, IgD, and IgE, including $F_{ab}$ or antigen-recognition fragments thereof. The antibodies may be monoclonal or polyclonal and may be of any species of origin, including (for example) mouse, rat, rabbit, horse, or human, or may be chimeric antibodies. See, e.g., M. Walker et al., *Molec. Immunol.* 26: 403-11 (1989); Morrision et al., *Proc. Nat'l. Acad. Sci.* 81: 6851 (1984); Neuberger et al., *Nature* 312: 604 (1984)). The antibodies may be recombinant monoclonal antibodies produced according to the methods disclosed in U.S. Pat. No. 4,474,893 (Reading) or U.S. Pat. No. 4,816,567 (Cabilly et al.) The antibodies may also be chemically constructed by specific antibodies made according to the method disclosed in U.S. Pat. No. 4,676,980 (Segel et al.)

The invention also provides immortalized cell lines that produce an antibody of the invention. For example, hybridoma clones, constructed as described above, that produce monoclonal antibodies to the Leukemia-related signaling protein phosphorylation sites disclosed herein are also provided. Similarly, the invention includes recombinant cells producing an antibody of the invention, which cells may be constructed by well known techniques; for example the antigen combining site of the monoclonal antibody can be cloned by PCR and single-chain antibodies produced as phage-displayed recombinant antibodies or soluble antibodies in *E. coli* (see, e.g., ANTIBODY ENGINEERING PROTOCOLS, 1995, Humana Press, Sudhir Paul editor.)

Phosphorylation site-specific antibodies of the invention, whether polyclonal or monoclonal, may be screened for epitope and phospho-specificity according to standard techniques. See, e.g. Czemik et al., *Methods in Enzymology*, 201: 264-283 (1991). For example, the antibodies may be screened against the phospho and non-phospho peptide library by ELISA to ensure specificity for both the desired antigen (i.e. that epitope including a phosphorylation site sequence enumerated in Column E of Table 1) and for reactivity only with the phosphorylated (or non-phosphorylated) form of the antigen. Peptide competition assays may be carried out to confirm lack of reactivity with other phospho-epitopes on the given Leukemia-related signaling protein. The antibodies may also be tested by Western blotting against cell preparations containing the signaling protein, e.g. cell lines over-expressing the target protein, to confirm reactivity with the desired phosphorylated epitope/target.

Specificity against the desired phosphorylated epitope may also be examined by constructing mutants lacking phosphorylatable residues at positions outside the desired epitope that are known to be phosphorylated, or by mutating the desired phospho-epitope and confirming lack of reactivity. Phosphorylation-site specific antibodies of the invention may exhibit some limited cross-reactivity to related epitopes in non-target proteins. This is not unexpected as most antibodies exhibit some degree of cross-reactivity, and anti-peptide antibodies will often cross-react with epitopes having high homology to the immunizing peptide. See, e.g., Czernik, supra. Cross-reactivity with non-target proteins is readily characterized by Western blotting alongside markers of known molecular weight. Amino acid sequences of cross-reacting proteins may be examined to identify sites highly homologous to the Leukemia-related signaling protein epitope for which the antibody of the invention is specific.

In certain cases, polyclonal antisera may exhibit some undesirable general cross-reactivity to phosphotyrosine or phosphoserine itself, which may be removed by further purification of antisera, e.g. over a phosphotyramine column. Antibodies of the invention specifically bind their target protein (i.e. a protein listed in Column A of Table 1) only when phosphorylated (or only when not phosphorylated, as the case may be) at the site disclosed in corresponding Columns D/E, and do not (substantially) bind to the other form (as compared to the form for which the antibody is specific).

Antibodies may be further characterized via immunohistochemical (IHC) staining using normal and diseased tissues to examine Leukemia-related phosphorylation and activation status in diseased tissue. IHC may be carried out according to well-known techniques. See, e.g., ANTIBODIES: A LABORATORY MANUAL, Chapter 10, Harlow & Lane Eds., Cold Spring Harbor Laboratory (1988). Briefly, paraffin-embedded tissue (e.g. tumor tissue) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary antibody and secondary antibody; and finally detecting using ABC avidin/biotin method according to manufacturer's instructions.

Antibodies may be further characterized by flow cytometry carried out according to standard methods. See Chow et al., *Cytometry (Communications in Clinical Cytometry)* 46: 72-78 (2001). Briefly and by way of example, the following protocol for cytometric analysis may be employed: samples may be centrifuged on Ficoll gradients to remove erythrocytes, and cells may then be fixed with 2% paraformaldehyde for 10 minutes at 37° C. followed by permeabilization in 90% methanol for 30 minutes on ice. Cells may then be stained with the primary phosphorylation-site specific antibody of the invention (which detects a Leukemia-related signal transduction protein enumerated in Table 1), washed and labeled with a fluorescent-labeled secondary antibody. Additional fluorochrome-conjugated marker antibodies (e.g. CD45, CD34) may also be added at this time to aid in the subsequent identification of specific hematopoietic cell types. The cells would then be analyzed on a flow cytometer (e.g. a Beckman Coulter FC500) according to the specific protocols of the instrument used.

Antibodies of the invention may also be advantageously conjugated to fluorescent dyes (e.g. Alexa488, PE) for use in multi-parametric analyses along with other signal transduction (phospho-CrkL, phospho-Erk 1/2) and/or cell marker (CD34) antibodies.

Phosphorylation-site specific antibodies of the invention specifically bind to a human Leukemia-related signal transduction protein or polypeptide only when phosphorylated at a disclosed site, but are not limited only to binding the human species, per se. The invention includes antibodies that also bind conserved and highly homologous or identical phosphorylation sites in respective Leukemia-related proteins from other species (e.g. mouse, rat, monkey, yeast), in addition to binding the human phosphorylation site. Highly homologous or identical sites conserved in other species can readily be identified by standard sequence comparisons, such as using BLAST, with the human Leukemia-related signal transduction protein phosphorylation sites disclosed herein.

C. Heavy-isotope Labeled Peptides (AQUA Peptides)

The novel Leukemia-related signaling protein phosphorylation sites disclosed herein now enable the production of corresponding heavy-isotope labeled peptides for the absolute quantification of such signaling proteins (both phosphorylated and not phosphorylated at a disclosed site) in biological samples. The production and use of AQUA peptides for the absolute quantification of proteins (AQUA) in complex mixtures has been described. See WO/03016861, "Absolute Quantification of Proteins and Modified Forms Thereof by Multistage Mass Spectrometry," Gygi et al. and also Gerber et al. *Proc. Natl. Acad. Sci. U.S.A.* 100: 6940-5 (2003) (the teachings of which are hereby incorporated herein by reference, in their entirety).

The AQUA methodology employs the introduction of a known quantity of at least one heavy-isotope labeled peptide standard (which has a unique signature detectable by LC-SRM chromatography) into a digested biological sample in order to determine, by comparison to the peptide standard, the absolute quantity of a peptide with the same sequence and protein modification in the biological sample. Briefly, the AQUA methodology has two stages: peptide internal standard selection and validation and method development; and implementation using validated peptide internal standards to detect and quantify a target protein in sample. The method is a powerful technique for detecting and quantifying a given peptide/protein within a complex biological mixture, such as a cell lysate, and may be employed, e.g., to quantify change in protein phosphorylation as a result of drug treatment, or to quantify differences in the level of a protein in different biological states.

Generally, to develop a suitable internal standard, a particular peptide (or modified peptide) within a target protein sequence is chosen based on its amino acid sequence and the particular protease to be used to digest. The peptide is then generated by solid-phase peptide synthesis such that one residue is replaced with that same residue containing stable isotopes ($^{13}C$, $^{15}N$). The result is a peptide that is chemically identical to its native counterpart formed by proteolysis, but is easily distinguishable by MS via a 7-Da mass shift. A newly synthesized AQUA internal standard peptide is then evaluated by LC-MS/MS. This process provides qualitative information about peptide retention by reverse-phase chromatography, ionization efficiency, and fragmentation via collision-induced dissociation. Informative and abundant fragment ions for sets of native and internal standard peptides are chosen and then specifically monitored in rapid succession as a function of chromatographic retention to form a selected reaction monitoring (LC-SRM) method based on the unique profile of the peptide standard.

The second stage of the AQUA strategy is its implementation to measure the amount of a protein or modified protein from complex mixtures. Whole cell lysates are typically fractionated by SDS-PAGE gel electrophoresis, and regions of the gel consistent with protein migration are excised. This process is followed by in-gel proteolysis in the presence of the AQUA peptides and LC-SRM analysis. (See Gerber et al. supra.) AQUA peptides are spiked in to the complex peptide mixture obtained by digestion of the whole cell lysate with a proteolytic enzyme and subjected to immunoaffinity purification as described above. The retention time and fragmentation pattern of the native peptide formed by digestion (e.g. trypsinization) is identical to that of the AQUA internal standard peptide determined previously; thus, LC-MS/MS analysis using an SRM experiment results in the highly specific and sensitive measurement of both internal standard and analyte directly from extremely complex peptide mixtures. Because an absolute amount of the AQUA peptide is added (e.g. 250 fmol), the ratio of the areas under the curve can be used to determine the precise expression levels of a protein or phosphorylated form of a protein in the original cell lysate. In addition, the internal standard is present during in-gel digestion as native peptides are formed, such that peptide extraction efficiency from gel pieces, absolute losses during sample handling (including vacuum centrifugation), and variability during introduction into the LC-MS system do not affect the determined ratio of native and AQUA peptide abundances.

An AQUA peptide standard is developed for a known phosphorylation site sequence previously identified by the IAP-LC-MS/MS method within a target protein. One AQUA peptide incorporating the phosphorylated form of the particular residue within the site may be developed, and a second AQUA peptide incorporating the non-phosphorylated form of the residue developed. In this way, the two standards may be used to detect and quantify both the phosphorylated and non-phosphorylated forms of the site in a biological sample.

Peptide internal standards may also be generated by examining the primary amino acid sequence of a protein and determining the boundaries of peptides produced by protease cleavage. Alternatively, a protein may actually be digested with a protease and a particular peptide fragment produced can then sequenced. Suitable proteases include, but are not limited to, serine proteases (e.g. trypsin, hepsin), metallo proteases (e.g. PUMP1), chymotrypsin, cathepsin, pepsin, thermolysin, carboxypeptidases, etc.

A peptide sequence within a target protein is selected according to one or more criteria to optimize the use of the peptide as an internal standard. Preferably, the size of the peptide is selected to minimize the chances that the peptide sequence will be repeated elsewhere in other non-target proteins. Thus, a peptide is preferably at least about 6 amino acids. The size of the peptide is also optimized to maximize ionization frequency. Thus, peptides longer than about 20 amino acids are not preferred. The preferred ranged is about 7 to 15 amino acids. A peptide sequence is also selected that is not likely to be chemically reactive during mass spectrometry, thus sequences comprising cysteine, tryptophan, or methionine are avoided.

A peptide sequence that does not include a modified region of the target region may be selected so that the peptide internal standard can be used to determine the quantity of all forms of the protein. Alternatively, a peptide internal standard encompassing a modified amino acid may be desirable to detect and quantify only the modified form of the target protein. Peptide standards for both modified and unmodified regions can be used together, to determine the extent of a modification in a particular sample (i.e. to determine what fraction of the total amount of protein is represented by the modified form). For example, peptide standards for both the phosphorylated and unphosphorylated form of a protein known to be phosphorylated at a particular site can be used to quantify the amount of phosphorylated form in a sample.

The peptide is labeled using one or more labeled amino acids (i.e. the label is an actual part of the peptide) or less preferably, labels may be attached after synthesis according to standard methods. Preferably, the label is a mass-altering label selected based on the following considerations: The mass should be unique to shift fragment masses produced by MS analysis to regions of the spectrum with low background; the ion mass signature component is the portion of the labeling moiety that preferably exhibits a unique ion mass signature in MS analysis; the sum of the masses of the constituent atoms of the label is preferably uniquely different than the fragments of all the possible amino acids. As a result, the labeled amino acids and peptides are readily distinguished from unlabeled ones by the ion/mass pattern in the resulting mass spectrum. Preferably, the ion mass signature component imparts a mass to a protein fragment that does not match the residue mass for any of the 20 natural amino acids.

The label should be robust under the fragmentation conditions of MS and not undergo unfavorable fragmentation. Labeling chemistry should be efficient under a range of conditions, particularly denaturing conditions, and the labeled tag preferably remains soluble in the MS buffer system of choice. The label preferably does not suppress the ionization efficiency of the protein and is not chemically reactive. The label may contain a mixture of two or more isotopically distinct species to generate a unique mass spectrometric pattern at each labeled fragment position. Stable isotopes, such as $^2H$, $^{13}C$, $^{15}N$, $^{17}O$, $^{18}O$, or $^{34}S$, are among preferred labels. Pairs of peptide internal standards that incorporate a different isotope label may also be prepared. Preferred amino acid residues into which a heavy isotope label may be incorporated include leucine, proline, valine, and phenylalanine.

Peptide internal standards are characterized according to their mass-to-charge (m/z) ratio, and preferably, also according to their retention time on a chromatographic column (e.g. an HPLC column). Internal standards that co-elute with unlabeled peptides of identical sequence are selected as optimal internal standards. The internal standard is then analyzed by fragmenting the peptide by any suitable means, for example by collision-induced dissociation (CID) using, e.g., argon or helium as a collision gas. The fragments are then analyzed, for example by multi-stage mass spectrometry ($MS^n$) to obtain a fragment ion spectrum, to obtain a peptide fragmentation signature. Preferably, peptide fragments have significant differences in m/z ratios to enable peaks corresponding to each fragment to be well separated, and a signature that is unique for the target peptide is obtained. If a suitable fragment signature is not obtained at the first stage, additional stages of MS are performed until a unique signature is obtained.

Fragment ions in the MS/MS and $MS^3$ spectra are typically highly specific for the peptide of interest, and, in conjunction with LC methods, allow a highly selective means of detecting and quantifying a target peptide/protein in a complex protein mixture, such as a cell lysate, containing many thousands or tens of thousands of proteins. Any biological sample potentially containing a target protein/peptide of interest may be assayed. Crude or partially purified cell extracts are preferably employed. Generally, the sample has at least 0.01 mg of protein, typically a concentration of 0.1-10 mg/mL, and may be adjusted to a desired buffer concentration and pH.

A known amount of a labeled peptide internal standard, preferably about 10 femtomoles, corresponding to a target protein to be detected/quantified is then added to a biological sample, such as a cell lysate. The spiked sample is then digested with one or more protease(s) for a suitable time period to allow digestion. A separation is then performed (e.g. by HPLC, reverse-phase HPLC, capillary electrophoresis, ion exchange chromatography, etc.) to isolate the labeled internal standard and its corresponding target peptide from other peptides in the sample. Microcapillary LC is a preferred method.

Each isolated peptide is then examined by monitoring of a selected reaction in the MS. This involves using the prior knowledge gained by the characterization of the peptide internal standard and then requiring the MS to continuously monitor a specific ion in the MS/MS or $MS^n$ spectrum for both the peptide of interest and the internal standard. After elution, the area under the curve (AUC) for both peptide standard and target peptide peaks are calculated. The ratio of the two areas provides the absolute quantification that can be normalized for the number of cells used in the analysis and the protein's molecular weight, to provide the precise number of copies of the protein per cell. Further details of the AQUA methodology are described in Gygi et al., and Gerber et al. supra.

In accordance with the present invention, AQUA internal peptide standards (heavy-isotope labeled peptides) may now be produced, as described above, for any of the nearly 288 novel Leukemia-related signaling protein phosphorylation sites disclosed herein (see Table 1/FIG. 2). Peptide standards for a given phosphorylation site (e.g. the tyrosine 712 in TRPM3—see Row 48 of Table 1) may be produced for both the phosphorylated and non-phosphorylated forms of the site (e.g. see TRPM3 site sequence in Column E, Row 48 of Table 1 (SEQ ID NO: 47) and such standards employed in the AQUA methodology to detect and quantify both forms of such phosphorylation site in a biological sample.

AQUA peptides of the invention may comprise all, or part of, a phosphorylation site peptide sequence disclosed herein (see Column E of Table 1/FIG. 2). In a preferred embodiment, an AQUA peptide of the invention comprises a phosphorylation site sequence disclosed herein in Table 1/FIG. 2. For example, an AQUA peptide of the invention for detection/quantification of C17orf31 DNA binding protein when phosphorylated at tyrosine Y52 may comprise the sequence RPDLElyKPGLSR (y=phosphotyrosine), which comprises phosphorylatable tyrosine 52 (see Row 329, Column E; (SEQ ID NO: 57)). Heavy-isotope labeled equivalents of the peptides enumerated in Table 1/FIG. 2 (both in phosphorylated and unphosphorylated form) can be readily synthesized and their unique MS and LC-SRM signature determined, so that the peptides are validated as AQUA peptides and ready for use in quantification experiments.

The phosphorylation site peptide sequences disclosed herein (see Column E of Table 1/FIG. 2) are particularly well suited for development of corresponding AQUA peptides, since the IAP method by which they were identified (see Part A above and Example 1) inherently confirmed that such peptides are in fact produced by enzymatic digestion (trypsinization) and are in fact suitably fractionated/ionized in MS/MS. Thus, heavy-isotope labeled equivalents of these peptides (both in phosphorylated and unphosphorylated form) can be readily synthesized and their unique MS and LC-SRM signature determined, so that the peptides are validated as AQUA peptides and ready for use in quantification experiments.

Accordingly, the invention provides heavy-isotope labeled peptides (AQUA peptides) for the detection and/or quantification of any of the Leukemia-related phosphorylation sites disclosed in Table 1/FIG. 2 (see Column E) and/or their corresponding parent proteins/polypeptides (see Column A). A phosphopeptide sequence comprising any of the phosphorylation sequences listed in Table 1 may be considered a preferred AQUA peptide of the invention. For example, an AQUA peptide comprising the sequence KESYSIYVyK (SEQ ID NO: 60) (where y may be either phosphotyrosine or tyrosine, and where V=labeled valine (e.g. $^{14}$C)) is provided for the quantification of phosphorylated (or non-phosphorylated) HIST1H2BO (Tyr43) in a biological sample (see Row 61 of Table 1, tyrosine 43 being the phosphorylatable residue within the site). However, it will be appreciated that a larger AQUA peptide comprising a disclosed phosphorylation site sequence (and additional residues downstream or upstream of it) may also be constructed. Similarly, a smaller AQUA peptide comprising less than all of the residues of a disclosed phosphorylation site sequence (but still comprising the phosphorylatable residue enumerated in Column D of Table 1/FIG. 2) may alternatively be constructed. Such larger or shorter AQUA peptides are within the scope of the present invention, and the selection and production of preferred AQUA peptides may be carried out as described above (see Gygi et al., Gerber et al. supra.).

Certain particularly preferred subsets of AQUA peptides provided by the invention are described above (corresponding to particular protein types/groups in Table 1, for example, Tyrosine Protein Kinases or Protein Phosphatases). Example 4 is provided to further illustrate the construction and use, by standard methods described above, of exemplary AQUA peptides provided by the invention. For example, the above-described AQUA peptides corresponding to both the phosphorylated and non-phosphorylated forms of the disclosed RAB11B G protein tyrosine 73 phosphorylation site (see Row 94 of Table 1/FIG. 2) may be used to quantify the amount of phosphorylated RAB11B (Tyr73) in a biological sample, e.g. a tumor cell sample (or a sample before or after treatment with a test drug).

AQUA peptides of the invention may also be employed within a kit that comprises one or multiple AQUA peptide(s) provided herein (for the quantification of a Leukemia-related signal transduction protein disclosed in Table 1/FIG. 2), and, optionally, a second detecting reagent conjugated to a detectable group. For example, a kit may include AQUA peptides for both the phosphorylated and non-phosphorylated form of a phosphorylation site disclosed herein. The reagents may also include ancillary agents such as buffering agents and protein stabilizing agents, e.g., polysaccharides and the like. The kit may further include, where necessary, other members of the signal-producing system of which system the detectable group is a member (e.g., enzyme substrates), agents for reducing background interference in a test, control reagents, apparatus for conducting a test, and the like. The test kit may be packaged in any suitable manner, typically with all elements in a single container along with a sheet of printed instructions for carrying out the test.

AQUA peptides provided by the invention will be highly useful in the further study of signal transduction anomalies underlying cancer, including leukemias, and in identifying diagnostic/bio-markers of these diseases, new potential drug targets, and/or in monitoring the effects of test compounds on Leukemia-related signal transduction proteins and pathways.

D. Immunoassay Formats

Antibodies provided by the invention may be advantageously employed in a variety of standard immunological assays (the use of AQUA peptides provided by the invention is described separately above). Assays may be homogeneous assays or heterogeneous assays. In a homogeneous assay the immunological reaction usually involves a phosphorylation-site specific antibody of the invention), a labeled analyte, and the sample of interest. The signal arising from the label is modified, directly or indirectly, upon the binding of the antibody to the labeled analyte. Both the immunological reaction and detection of the extent thereof are carried out in a homogeneous solution. Immunochemical labels that may be employed include free radicals, radioisotopes, fluorescent dyes, enzymes, bacteriophages, coenzymes, and so forth.

In a heterogeneous assay approach, the reagents are usually the specimen, a phosphorylation-site specific antibody of the invention, and suitable means for producing a detectable signal. Similar specimens as described above may be used. The antibody is generally immobilized on a support, such as a bead, plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the specimen. Means for producing a detectable signal include the use of radioactive labels, fluorescent labels, enzyme labels, and so forth. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are the radioimmunoassay, immunofluorescence methods, enzyme-linked immunoassays, and the like.

Immunoassay formats and variations thereof that may be useful for carrying out the methods disclosed herein are well known in the art. See generally E. Maggio, Enzyme-Immunoassay, (1980) (CRC Press, Inc., Boca Raton, Fla.); see also, e.g., U.S. Pat. No. 4,727,022 (Skold et al., "Methods for Modulating Ligand-Receptor Interactions and their Application"); U.S. Pat. No. 4,659,678 (Forrest et al., "Immunoassay of Antigens"); U.S. Pat. No. 4,376,110 (David et al., "Immunometric Assays Using Monoclonal Antibodies"). Conditions suitable for the formation of reagent-antibody complexes are well described. See id. Monoclonal antibodies of the invention may be used in a "two-site" or "sandwich" assay, with a single cell line serving as a source for both the labeled monoclonal antibody and the bound monoclonal antibody. Such assays are described in U.S. Pat. No. 4,376,110. The concentration of detectable reagent should be sufficient such that the binding of a target Leukemia-related signal transduction protein is detectable compared to background.

Phosphorylation site-specific antibodies disclosed herein may be conjugated to a solid support suitable for a diagnostic assay (e.g., beads, plates, slides or wells formed from materials such as latex or polystyrene) in accordance with known techniques, such as precipitation. Antibodies, or other target protein or target site-binding reagents, may likewise be conjugated to detectable groups such as radiolabels (e.g., $^{35}$S, $^{125}$I, $^{131}$I), enzyme labels (e.g., horseradish peroxidase, alkaline phosphatase), and fluorescent labels (e.g., fluorescein) in accordance with known techniques.

Antibodies of the invention may also be optimized for use in a flow cytometry (FC) assay to determine the activation/phosphorylation status of a target Leukemia-related signal transduction protein in patients before, during, and after treatment with a drug targeted at inhibiting phosphorylation at such a protein at the phosphorylation site disclosed herein. For example, bone marrow cells or peripheral blood cells from patients may be analyzed by flow cytometry for target Leukemia-related signal transduction protein phosphorylation, as well as for markers identifying various hematopoietic cell types. In this manner, activation status of the malignant cells may be specifically characterized. Flow cytometry may be carried out according to standard methods. See, e.g. Chow et al., Cytometry (*Communications in Clinical Cytometry*) 46: 72-78 (2001). Briefly and by way of example, the following protocol for cytometric analysis may be employed: fixation of the cells with 1% para-formaldehyde for 10 minutes at 37° C. followed by permeabilization in 90% methanol for 30 minutes on ice. Cells may then be stained with the primary antibody (a phospho-specific antibody of the invention), washed and labeled with a fluorescent-labeled secondary antibody. Alternatively, the cells may be stained with a fluorescent-labeled primary antibody. The cells would then be analyzed on a flow cytometer (e.g. a Beckman Coulter EPICS-XL) according to the specific protocols of the instrument used. Such an analysis would identify the presence of activated Leukemia-related signal transduction protein(s) in the malignant cells and reveal the drug response on the targeted protein.

Alternatively, antibodies of the invention may be employed in immunohistochemical (IHC) staining to detect differences in signal transduction or protein activity using normal and diseased tissues. IHC may be carried out according to well-known techniques. See, e.g., ANTIBODIES: A LABORATORY MANUAL, supra. Briefly, paraffin-embedded tissue (e.g. tumor tissue) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary antibody and secondary antibody; and finally detecting using ABC avidin/biotin method according to manufacturer's instructions.

Antibodies of the invention may be also be optimized for use in other clinically-suitable applications, for example bead-based multiplex-type assays, such as IGEN, Luminex™ and/or Bioplex™ assay formats, or otherwise optimized for antibody arrays formats, such as reversed-phase array applications (see, e.g. Paweletz et al., *Oncogene* 20(16): 1981-89 (2001)). Accordingly, in another embodiment, the invention provides a method for the multiplex detection of Leukemia-related protein phosphorylation in a biological sample, the method comprising utilizing two or more antibodies or AQUA peptides of the invention to detect the presence of two or more phosphorylated Leukemia-related signaling proteins enumerated in Column A of Table 1/FIG. 2. In one preferred embodiment, two to five antibodies or AQUA peptides of the invention are employed in the method. In another preferred embodiment, six to ten antibodies or AQUA peptides of the invention are employed, while in another preferred embodiment eleven to twenty such reagents are employed.

Antibodies and/or AQUA peptides of the invention may also be employed within a kit that comprises at least one phosphorylation site-specific antibody or AQUA peptide of the invention (which binds to or detects a Leukemia-related signal transduction protein disclosed in Table 1/FIG. 2), and, optionally, a second antibody conjugated to a detectable group. In some embodies, the kit is suitable for multiplex assays and comprises two or more antibodies or AQUA peptides of the invention, and in some embodiments, comprises two to five, six to ten, or eleven to twenty reagents of the invention. The kit may also include ancillary agents such as buffering agents and protein stabilizing agents, e.g., polysaccharides and the like. The kit may further include, where necessary, other members of the signal-producing system of which system the detectable group is a member (e.g., enzyme substrates), agents for reducing background interference in a test, control reagents, apparatus for conducting a test, and the like. The test kit may be packaged in any suitable manner, typically with all elements in a single container along with a sheet of printed instructions for carrying out the test.

The following Examples are provided only to further illustrate the invention, and are not intended to limit its scope, except as provided in the claims appended hereto. The present invention encompasses modifications and variations of the methods taught herein which would be obvious to one of ordinary skill in the art.

EXAMPLE 1

Isolation of Phosphotyrosine-Containing Peptides from Extracts of Leukemia Cell Lines and Identification of Novel Phosphorylation Sites In order to discover previously unknown Leukemia-related signal transduction protein phosphorylation sites, IAP isolation techniques were employed to identify phosphotyrosine- and/or phosphoserine-containing peptides in cell extracts from the following human Leukemia cell lines and patient cell lines: Jurkat, K562, SEM, HT-93, CTV-1, MOLT15, CLL-9, H1993, OCI-ly3, KBM-3, UT-7, SUPT-13, MKPL-1, HU-3, M-07e, HU-3, EHEB, SU-DHL1, OCI-ly1, DU-528, CMK, OCI-ly8, ELF-153, OCI-ly18, MEC-1, Karpas 299, CLL23LB4, OCI-ly12, M01043, CLL-10, HL60, Molm 14, MV4-11, CLL-1202, EOL-1, CLL-19, CV-1, PL21; or from the following cell lines expressing activated BCR-Abl wild type and mutant kinases such as: Baf3-p210 BCR-Abl, Baf3-M351T-BCR-ABL, Baf3-E255K-BCR-Abl, Baf3-Y253F-BCR-Abl, Baf3-T315I-BCR-ABI, 3T3-v-Abl; or activated Flt3 kinase such as Baf3-FLT3 or FLT3-ITD; or JAK2 such as Baf3/Jak2; or mutant JAK2 V617F such as Baf3-V617F-JAK2, or Tyk2 such as Baf3/Tyk2; or TEL-FGFR3 such as Baf3-Tel/FGFR3; or TpoR such as Baf3/TpoR and Baf3/cc-TpoR-IV; or FGFR1 such as 293T-FGFR.

Tryptic phosphotyrosine- and phosphoserine-containing peptides were purified and analyzed from extracts of each of the 29 cell lines mentioned above, as follows. Cells were cultured in DMEM medium or RPMI 1640 medium supplemented with 10% fetal bovine serum and penicillin/streptomycin.

Suspension cells were harvested by low speed centrifugation. After complete aspiration of medium, cells were resuspended in 1 mL lysis buffer per $1.25 \times 10^8$ cells (20 mM HEPES pH 8.0, 9 M urea, 1 mM sodium vanadate, supplemented or not with 2.5 mM sodium pyro-phosphate, 1 mM β-glycerol-phosphate) and sonicated.

Sonicated cell lysates were cleared by centrifugation at 20,000×g, and proteins were reduced with DTT at a final concentration of 4.1 mM and alkylated with iodoacetamide at 8.3 mM. For digestion with trypsin, protein extracts were diluted in 20 mM HEPES pH 8.0 to a final concentration of 2 M urea and soluble TLCK-trypsin (Worthington) was added at 10-20 μg/mL. Digestion was performed for 1-2 days at room temperature.

Trifluoroacetic acid (TFA) was added to protein digests to a final concentration of 1%, precipitate was removed by centrifugation, and digests were loaded onto Sep-Pak $C_{18}$ columns (Waters) equilibrated with 0.1% TFA. A column volume of 0.7-1.0 ml was used per $2 \times 10^8$ cells. Columns were washed with 15 volumes of 0.1% TFA, followed by 4 volumes of 5% acetonitrile (MeCN) in 0.1% TFA. Peptide fraction I was obtained by eluting columns with 2 volumes each of 8, 12, and 15% MeCN in 0.1% TFA and combining the eluates. Fractions II and III were a combination of eluates after eluting columns with 18, 22, 25% MeCN in 0.1% TFA and with 30, 35, 40% MeCN in 0.1% TFA, respectively. All peptide fractions were lyophilized.

Peptides from each fraction corresponding to $2 \times 10^8$ cells were dissolved in 1 ml of IAP buffer (20 mM Tris/HCl or 50 mM MOPS pH 7.2, 10 mM sodium phosphate, 50 mM NaCl) and insoluble matter (mainly in peptide fractions III) was removed by centrifugation. IAP was performed on each peptide fraction separately. The phosphotyrosine monoclonal antibody P-Tyr-100 (Cell Signaling Technology, Inc., catalog number 9411) was coupled at 4 mg/ml beads to protein G or protein A agarose (Roche), respectively. Immobilized antibody (15 μl, 60 μg) was added as 1:1 slurry in IAP buffer to 1 ml of each peptide fraction, and the mixture was incubated overnight at 4° C. with gentle rotation. The immobilized antibody beads were washed three times with 1 ml IAP buffer and twice with 1 ml water, all at 4° C. Peptides were eluted from beads by incubation with 75 μl of 0.1% TFA at room temperature for 10 minutes.

Alternatively, one single peptide fraction was obtained from Sep-Pak C18 columns by elution with 2 volumes each of 10%, 15%, 20%, 25%, 30%, 35% and 40% acetonitrile in 0.1% TFA and combination of all eluates. IAP on this peptide fraction was performed as follows: After lyophilization, peptide was dissolved in 1.4 ml IAP buffer (MOPS pH 7.2, 10 mM sodium phosphate, 50 mM NaCl) and insoluble matter was removed by centrifugation. Immobilized antibody (40 μl, 160 μg) was added as 1:1 slurry in IAP buffer, and the mixture was incubated overnight at 4° C. with gentle shaking. The immobilized antibody beads were washed three times with 1 ml IAP buffer and twice with 1 ml water, all at 4° C. Peptides were eluted from beads by incubation with 55 μl of 0.15% TFA at room temperature for 10 min (eluate 1), followed by a wash of the beads (eluate 2) with 45 μl of 0.15% TFA. Both eluates were combined.

Analysis by LC-MS/MS Mass Spectrometry

40 μl or more of IAP eluate were purified by 0.2 μl StageTips or ZipTips. Peptides were eluted from the microcolumns with 1 μl of 40% MeCN, 0.1% TFA (fractions I and II) or 1 μl of 60% MeCN, 0.1% TFA (fraction III) into 7.6 μl of 0.4% acetic acid/0.005% heptafluorobutyric acid. This sample was loaded onto a 10 cm×75 μm PicoFrit capillary column (New Objective) packed with Magic C18 AQ reversed-phase resin (Michrom Bioresources) using a Famos autosampler with an inert sample injection valve (Dionex). The column was then developed with a 45-min linear gradient of acetonitrile delivered at 200 nl/min (Ultimate, Dionex), and tandem mass spectra were collected in a data-dependent manner with an LTQ ion trap mass spectrometer essentially as described by Gygi et al., supra.

Database Analysis & Assignments

MS/MS spectra were evaluated using TurboSequest in the Sequest Browser package (v. 27, rev. 12) supplied as part of BioWorks 3.0 (ThermoFinnigan). Individual MS/MS spectra were extracted from the raw data file using the Sequest Browser program CreateDta, with the following settings: bottom MW, 700; top MW, 4,500; minimum number of ions, 20; minimum TIC, $4 \times 10^5$; and precursor charge state, unspecified. Spectra were extracted from the beginning of the raw data file before sample injection to the end of the eluting gradient. The IonQuest and VuDta programs were not used to further select MS/MS spectra for Sequest analysis. MS/MS spectra were evaluated with the following TurboSequest parameters: peptide mass tolerance, 2.5; fragment ion tolerance, 0.0; maximum number of differential amino acids per modification, 4; mass type parent, average; mass type fragment, average; maximum number of internal cleavage sites, 10; neutral losses of water and ammonia from b and y ions were considered in the correlation analysis. Proteolytic enzyme was specified except for spectra collected from elastase digests.

Searches were performed against the NCBI human protein database (as released on Feb. 23, 2004 and containing 27,175 protein sequences). Cysteine carboxamidomethylation was specified as a static modification, and phosphorylation was allowed as a variable modification on serine, threonine, and tyrosine residues or on tyrosine residues alone. It was determined that restricting phosphorylation to tyrosine residues had little effect on the number of phosphorylation sites assigned. Furthermore, it should be noted that certain peptides were originally isolated in mouse and later normalized to human sequences as shown by Table 1/FIG. 2.

In proteomics research, it is desirable to validate protein identifications based solely on the observation of a single peptide in one experimental result, in order to indicate that the protein is, in fact, present in a sample. This has led to the development of statistical methods for validating peptide assignments, which are not yet universally accepted, and guidelines for the publication of protein and peptide identification results (see Carr et al., Mol. Cell. Proteomics 3: 531-533 (2004)), which were followed in this Example. However, because the immunoaffinity strategy separates phosphorylated peptides from unphosphorylated peptides, observing just one phosphopeptide from a protein is a common result, since many phosphorylated proteins have only one tyrosine-phosphorylated site. For this reason, it is appropriate to use additional criteria to validate phosphopeptide assignments. Assignments are likely to be correct if any of these additional criteria are met: (i) the same sequence is assigned to co-eluting ions with different charge states, since the MS/MS spectrum changes markedly with charge state; (ii) the site is found in more than one peptide sequence context due to sequence overlaps from incomplete proteolysis or use of proteases other than trypsin; (iii) the site is found in more than one peptide sequence context due to homologous but not identical protein isoforms; (iv) the site is found in more than one peptide sequence context due to homologous but not identical proteins among species; and (v) sites validated by MS/MS analysis of synthetic phosphopeptides corresponding to assigned sequences, since the ion trap mass spectrometer produces highly reproducible MS/MS spectra. The last criterion is routinely employed to confirm novel site assignments of particular interest.

All spectra and all sequence assignments made by Sequest were imported into a relational database. The following Sequest scoring thresholds were used to select phosphopeptide assignments that are likely to be correct: RSp<6, XCorr≧2.2, and DeltaCN>0.099. Further, the assigned sequences could be accepted or rejected with respect to accuracy by using the following conservative, two-step process.

In the first step, a subset of high-scoring sequence assignments should be selected by filtering for XCorr values of at least 1.5 for a charge state of +1, 2.2 for +2, and 3.3 for +3, allowing a maximum RSp value of 10. Assignments in this subset should be rejected if any of the following criteria were satisfied: (i) the spectrum contains at least one major peak (at least 10% as intense as the most intense ion in the spectrum) that can not be mapped to the assigned sequence as an a, b, or y ion, as an ion arising from neutral-loss of water or ammonia from a b or y ion, or as a multiply protonated ion; (ii) the spectrum does not contain a series of b or y ions equivalent to at least six uninterrupted residues; or (iii) the sequence is not observed at least five times in all the studies conducted (except for overlapping sequences due to incomplete proteolysis or use of proteases other than trypsin).

In the second step, assignments with below-threshold scores should be accepted if the low-scoring spectrum shows a high degree of similarity to a high-scoring spectrum collected in another study, which simulates a true reference library-searching strategy.

EXAMPLE 2

Production of Phospho-Specific Polyclonal Antibodies for the Detection of Leukemia-related Signaling Protein Phosphorylation Polyclonal antibodies that specifically bind a Leukemia-related signal transduction protein only when phosphorylated at the respective phosphorylation site disclosed herein (see Table 1/FIG. 2) are produced according to standard methods by first constructing a synthetic peptide antigen comprising the phosphorylation site sequence and then immunizing an animal to raise antibodies against the antigen, as further described below. Production of exemplary polyclonal antibodies is provided below.

A. SCAMP3 (Tyrosine 41)

A 14 amino acid phospho-peptide antigen, QYATLDVy*NPFETR (where y*=phosphotyrosine) that corresponds to the sequence encompassing the tyrosine 41 phosphorylation site in human SCAMP3 vesicle protein (see Row 280 of Table 1; SEQ ID NO: 279), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals to produce (and subsequently screen) phospho-specific SCAMP3 (tyr41) polyclonal antibodies as described in Immunization/Screening below.

B. BIRC4BP (Tyrosine 261)

A 10 amino acid phospho-peptide antigen, GDKAAy*DILR (where s*=phosphotyrosine) that corresponds to the sequence encompassing the tyrosine 261 phosphorylation site in human BIRC4BP apoptosis protein (see Row 38 of Table 1 (SEQ ID NO: 37)), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals to produce (and subsequently screen) phospho-specific BIRC4BP (tyr261) polyclonal antibodies as described in Immunization/Screening below.

C. PUM1 (Tyrosine 83)

A 13 amino acid phospho-peptide antigen, SQDDAMVDYy*FFQR (where y*=phosphotyrosine) that corresponds to the sequence encompassing the tyrosine 83 phosphorylation site in human PUM1 phosphatase protein (see Row 142 of Table 1 (SEQ ID NO: 141), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals to produce (and subsequently screen) phospho-specific PUM1 (tyr83) antibodies as described in Immunization/Screening Below.

Immunization/Screening

A synthetic phospho-peptide antigen as described in A-C above is coupled to KLH, and rabbits are injected intradermally (ID) on the back with antigen in complete Freunds adjuvant (500 μg antigen per rabbit). The rabbits are boosted with same antigen in incomplete Freund adjuvant (250 μg antigen per rabbit) every three weeks. After the fifth boost, bleeds are collected. The sera are purified by Protein A-affinity chromatography by standard methods (see ANTIBODIES: A LABORATORY MANUAL, Cold Spring Harbor, supra.). The eluted immunoglobulins are further loaded onto a non-phosphorylated synthetic peptide antigen-resin Knotes column to pull out antibodies that bind the non-phosphorylated form of the phosphorylation site. The flow through fraction is collected and applied onto a phospho-synthetic peptide antigen-resin column to isolate antibodies that bind the phosphorylated form of the site. After washing the column extensively, the bound antibodies (i.e. antibodies that bind a phosphorylated peptide described in A-C above, but do not bind the non-phosphorylated form of the peptide) are eluted and kept in antibody storage buffer.

The isolated antibody is then tested for phospho-specificity using Western blot assay using an appropriate cell line that expresses (or overexpresses) target phospho-protein (i.e. phosphorylated SCAMP3, PUM1 or BIRC4BP), for example, SEM and Jurkat cells, respectively. Cells are cultured in DMEM or RPMI supplemented with 10% FCS. Cell are collected, washed with PBS and directly lysed in cell lysis buffer. The protein concentration of cell lysates is then measured. The loading buffer is added into cell lysate and the mixture is boiled at 100° C. for 5 minutes. 20 μl (10 μg protein) of sample is then added onto 7.5% SDS-PAGE gel.

A standard Western blot may be performed according to the Immunoblotting Protocol set out in the CELL SIGNALING TECHNOLOGY, INC. 2003-04 Catalogue, p. 390. The isolated phospho-specific antibody is used at dilution 1:1000. Phosphorylation-site specificity of the antibody will be shown by binding of only the phosphorylated form of the target protein. Isolated phospho-specific polyclonal antibody does not (substantially) recognize the target protein when not phosphorylated at the appropriate phosphorylation site in the non-stimulated cells (e.g. SCAMP3 is not bound when not phosphorylated at tyrosine 41).

In order to confirm the specificity of the isolated antibody, different cell lysates containing various phosphorylated signal transduction proteins other than the target protein are prepared. The Western blot assay is performed again using these cell lysates. The phospho-specific polyclonal antibody isolated as described above is used (1:1000 dilution) to test reactivity with the different phosphorylated non-target proteins on Western blot membrane. The phospho-specific antibody does not significantly cross-react with other phosphorylated signal transduction proteins, although occasionally slight binding with a highly homologous phosphorylation-site on another protein may be observed. In such case the antibody may be further purified using affinity chromatography, or the specific immunoreactivity cloned by rabbit hybridoma technology.

EXAMPLE 3

Production of Phospho-Specific Monoclonal Antibodies for the Detection of Leukemia-Related Signaling Protein Phosphorylation Monoclonal antibodies that specifically bind a Leukemia-related signal transduction protein only when phosphorylated at the respective phosphorylation site disclosed herein (see Table 1/FIG. 2) are produced according to standard methods by first constructing a synthetic peptide antigen comprising the phosphorylation site sequence and then immunizing an animal to raise antibodies against the antigen, and harvesting spleen cells from such animals to produce fusion hybridomas, as further described below. Production of exemplary monoclonal antibodies is provided below.

A. ADAMTS14 (Tyrosine 38)

A 15 amino acid phospho-peptide antigen, LSDy*GVTVPCSTDFR (where y*=phosphotyrosine) that corresponds to the sequence encompassing the tyrosine 38 phosphorylation site in human ADAMTS14 protease (see Row 368 of Table 1 (SEQ ID NO: 142)), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals and harvest spleen cells for generation (and subsequent screening) of phospho-specific monoclonal ADAMTS14 (tyr38) antibodies as described in Immunization/Fusion/Screening below.

B. AVO3 (Tyrosine 1269)

A 16 amino acid phospho-peptide antigen, TSHy*LTPQSNHLSLSK (where y*=phosphotyrosine) that corresponds to the sequence encompassing the tyrosine 1269 phosphorylation site in human LRRK1 kinase (see Row 147 of Table 1 (SEQ ID NO: 146)), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals and harvest spleen cells for generation (and subsequent screening) of phospho-specific monoclonal AVO3 (tyr1269) antibodies as described in Immunization/Fusion/Screening below.

C. RBM15 (Tyrosine 251)

An 8 amino acid phospho-peptide antigen, IEAVy*VSR (where y*=phosphotyrosine) that corresponds to the sequence encompassing the tyrosine 251 phosphorylation site in human RBM15 RNA binding protein (see Row 203 of Table 1 (SEQ ID NO: 202), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals and harvest spleen cells for generation (and subsequent screening) of phospho-specific monoclonal RBM15 (tyr251) antibodies as described in Immunization/Fusion/Screening below.

Immunization/Fusion/Screening

A synthetic phospho-peptide antigen as described in A-C above is coupled to KLH, and BALB/C mice are injected intradermally (ID) on the back with antigen in complete Freunds adjuvant (e.g. 50 μg antigen per mouse). The mice are boosted with same antigen in incomplete Freund adjuvant (e.g. 25 μg antigen per mouse) every three weeks. After the fifth boost, the animals are sacrificed and spleens are harvested.

Harvested spleen cells are fused to SP2/0 mouse myeloma fusion partner cells according to the standard protocol of Kohler and Milstein (1975). Colonies originating from the fusion are screened by ELISA for reactivity to the phospho-peptide and non-phospho-peptide forms of the antigen and by Western blot analysis (as described in Example 1 above). Colonies found to be positive by ELISA to the phospho-peptide while negative to the non-phospho-peptide are further characterized by Western blot analysis. Colonies found to be positive by Western blot analysis are subcloned by limited dilution. Mouse ascites are produced from a single clone obtained from subcloning, and tested for phospho-specificity (against the ADAMTS14, AVO3 or RBM15 phospho-peptide antigen, as the case may be) on ELISA. Clones identified as positive on Western blot analysis using cell culture supernatant as having phospho-specificity, as indicated by a strong band in the induced lane and a weak band in the uninduced lane of the blot, are isolated and subcloned as clones producing monoclonal antibodies with the desired specificity.

Ascites fluid from isolated clones may be further tested by Western blot analysis. The ascites fluid should produce similar results on Western blot analysis as observed previously with the cell culture supernatant, indicating phospho-specificity against the phosphorylated target (e.g. RBM phosphorylated at tyrosine 251).

EXAMPLE 4

Production and Use of AQUA Peptides for the Quantification of Leukemia-related Signaling Protein Phosphorylation Heavy-isotope labeled peptides (AQUA peptides (internal standards)) for the detection and quantification of a Leukemia-related signal transduction protein only when phosphorylated at the respective phosphorylation site disclosed herein (see Table 1/FIG. 2) are produced according to the standard AQUA methodology (see Gygi et al., Gerber et al., supra.) methods by first constructing a synthetic peptide standard corresponding to the phosphorylation site sequence and incorporating a heavy-isotope label. Subsequently, the $MS^n$ and LC-SRM signature of the peptide standard is validated, and the AQUA peptide is used to quantify native peptide in a biological sample, such as a digested cell extract. Production and use of exemplary AQUA peptides is provided below.

A. RICS (Tyrosine 1353)

An AQUA peptide comprising the sequence, SLy*SYAGLAPRPR (y*=phosphotyrosine; sequence incorporating $^{14}C/^{15}N$-labeled leucine (indicated by bold L), which corresponds to the tyrosine 1353 phosphorylation site in human RICS GTPase activating protein (see Row 100 in Table 1 (SEQ ID NO: 99)), is constructed according to standard synthesis techniques using, e.g., a Rainin/Protein Technologies, Inc., Symphony peptide synthesizer (see Merrifield, supra.) as further described below in Synthesis & MS/MS Signature. The RICS (tyr1353) AQUA peptide is then spiked into a biological sample to quantify the amount of phosphorylated RICS (tyr1353) in the sample, as further described below in Analysis & Quantification.

B. LAX1 (Tyrosine 373)

An AQUA peptide comprising the sequence HREEMSNEDSSDy*ENVLTAK (y*=phosphotyrosine; sequence incorporating $^{14}C/^{15}N$-labeled leucine (indicated by bold L), which corresponds to the tyrosine 373 phosphorylation site in human LAX1 adaptor/scaffold protein (see Row 15 in Table 1 (SEQ ID NO: 14)), is constructed according to standard synthesis techniques using, e.g., a Rainin/Protein Technologies, Inc., Symphony peptide synthesizer (see Merrifield, supra.) as further described below in Synthesis & MS/MS Signature. The LAX1 (tyr373) AQUA peptide is then spiked into a biological sample to quantify the amount of phosphorylated LAX1 (tyr373) in the sample, as further described below in Analysis & Quantification.

C. FAT (Tyrosine 400)

An AQUA peptide comprising the sequence, DVYRAEISEFAPPNTPVVMVKAIPAYSHLRy*VFK (y*=phosphotyrosine; sequence incorporating $^{14}C/^{15}N$-labeled phenylalanine (indicated by bold F), which corresponds to the tyrosine 400 phosphorylation site in human FAT adhesion protein (see Row 23 in Table 1 (SEQ ID NO: 22)), is constructed according to standard synthesis techniques using, e.g., a Rainin/Protein Technologies, Inc., Symphony peptide synthesizer (see Merrifield, supra.) as further described below in Synthesis & MS/MS Signature. The FAT (tyr400) AQUA peptide is then spiked into a biological sample to quantify the amount of phosphorylated FAT (tyr400) in the sample, as further described below in Analysis & Quantification.

D. SNAP23 (Tyrosine 139)

An AQUA peptide comprising the sequence, QPGPVTNGQLQQPTTGASGGy*IK (y*=phosphotyrosine; sequence incorporating $^{14}C/^{15}N$-labeled proline (indicated by bold P), which corresponds to the tyrosine 139 phosphorylation site in human SNAP23 vesicle protein (see Row 281 in Table 1 (SEQ ID NO: 280)), is constructed according to standard synthesis techniques using, e.g., a Rainin/Protein Technologies, Inc., Symphony peptide synthesizer (see Merrifield, supra.) as further described below in Synthesis & MS/MS Signature. The SNAP23 (tyr139) AQUA peptide is then spiked into a biological sample to quantify the amount of phosphorylated SNAP23 (tyr139) in the sample, as further described below in Analysis & Quantification.

Synthesis & MS/MS Spectra

Fluorenylmethoxycarbonyl (Fmoc)-derivatized amino acid monomers may be obtained from AnaSpec (San Jose, Calif.). Fmoc-derivatized stable-isotope monomers containing one $^{15}N$ and five to nine $^{13}C$ atoms may be obtained from Cambridge Isotope Laboratories (Andover, Mass.). Pre-loaded Wang resins may be obtained from Applied Biosystems. Synthesis scales may vary from 5 to 25 µmol. Amino acids are activated in situ with 1-H-benzotriazolium, 1-bis (dimethylamino) methylene]-hexafluorophosphate (1-),3-oxide:1-hydroxybenzotriazole hydrate and coupled at a 5-fold molar excess over peptide. Each coupling cycle is followed by capping with acetic anhydride to avoid accumulation of one-residue deletion peptide by-products. After synthesis peptide-resins are treated with a standard scavenger-containing trifluoroacetic acid (TFA)-water cleavage solution, and the peptides are precipitated by addition to cold ether. Peptides (i.e. a desired AQUA peptide described in A-D above) are purified by reversed-phase C18 HPLC using standard TFA/acetonitrile gradients and characterized by matrix-assisted laser desorption ionization-time of flight (Biflex III, Bruker Daltonics, Billerica, Mass.) and ion-trap (ThermoFinnigan, LCQ DecaXP) MS.

MS/MS spectra for each AQUA peptide should exhibit a strong y-type ion peak as the most intense fragment ion that is suitable for use in an SRM monitoring/analysis. Reverse-phase microcapillary columns (0.1 Å~150-220 mm) are prepared according to standard methods. An Agilent 1100 liquid chromatograph may be used to develop and deliver a solvent gradient [0.4% acetic acid/0.005% heptafluorobutyric acid (HFBA)/7% methanol and 0.4% acetic acid/0.005% HFBA/65% methanol/35% acetonitrile] to the microcapillary column by means of a flow splitter. Samples are then directly loaded onto the microcapillary column by using a FAMOS inert capillary autosampler (LC Packings, San Francisco) after the flow split. Peptides are reconstituted in 6% acetic acid/0.01% TFA before injection.

Analysis & Quantification

Target protein (e.g. a phosphorylated protein of A-D above) in a biological sample is quantified using a validated AQUA peptide (as described above). The IAP method is then applied to the complex mixture of peptides derived from proteolytic cleavage of crude cell extracts to which the AQUA peptides have been spiked in.

LC-SRM of the entire sample is then carried out. MS/MS may be performed by using a ThermoFinnigan (San Jose, Calif.) mass spectrometer (LTQ ion trap or TSQ Quantum triple quadrupole). On the LTQ, parent ions are isolated at 1.6 m/z width, the ion injection time being limited to 100 ms per microscan, with one microscans per peptide, and with an AGC setting of $1\times10^5$; on the Quantum, Q1 is kept at 0.4 and Q3 at 0.8 m/z with a scan time of 200 ms per peptide. On both instruments, analyte and internal standard are analyzed in alternation within a previously known reverse-phase retention window; well-resolved pairs of internal standard and analyte are analyzed in separate retention segments to improve duty cycle. Data are processed by integrating the appropriate peaks in an extracted ion chromatogram (60.15 m/z from the fragment monitored) for the native and internal standard, followed by calculation of the ratio of peak areas multiplied by the absolute amount of internal standard (e.g., 500 fmol).

What is claimed is:

1. An isolated phosphorylation site-specific antibody that specifically binds a human CASC3 protein only when phosphorylated at the tyrosine at position 181, comprised within the phosphorylatable peptide sequence listed in SEQ ID NO: 171, wherein said antibody does not bind said protein when not phosphorylated at said tyrosine.

2. An isolated phosphorylation site-specific antibody that specifically binds a human SLC29A4 protein only when phosphorylated at the tyrosine at position 198, comprised within the phosphorylatable peptide sequence listed in SEQ ID NO: 254, wherein said antibody does not bind said protein when not phosphorylated at said tyrosine.

3. An isolated phosphorylation site-specific antibody that specifically binds a human CASC3 protein only when not phosphorylated at the tyrosine at position 181, comprised within the phosphorylatable peptide sequence listed in SEQ ID NO: 171, wherein said antibody does not bind said protein when phosphorylated at said tyrosine.

4. An isolated phosphorylation site-specific antibody that specifically binds a human SLC29A4 protein only when not phosphorylated at the tyrosine at position 198, comprised within the phosphorylatable peptide sequence listed in SEQ ID NO: 254, wherein said antibody does not bind said protein when phosphorylated at said tyrosine.

* * * * *